United States Patent
Livermore et al.

(10) Patent No.: US 9,593,106 B2
(45) Date of Patent: Mar. 14, 2017

(54) PIPERIDIN-1-YL AND AZEPIN-1-YL CARBOXYLATES AS MUSCARINIC M4 RECEPTOR AGONISTS

(71) Applicant: Heptares Therapeutics Limited, Welwyn Garden (GB)

(72) Inventors: David Livermore, Cambridge (GB); Kathryn White, Cambridge (GB); Miles Congreve, Welwyn Garden (GB); Giles Brown, Welwyn Garden (GB); Michael O'Brien, Welwyn Garden (GB)

(73) Assignee: Heptares Therapeutics Limited, Welwyn Garden (GB)

(*) Notice: Subject to any disclaimer, the term of this patent is extended or adjusted under 35 U.S.C. 154(b) by 0 days.

(21) Appl. No.: 14/766,520

(22) PCT Filed: Feb. 7, 2014

(86) PCT No.: PCT/GB2014/050371
§ 371 (c)(1),
(2) Date: Aug. 7, 2015

(87) PCT Pub. No.: WO2014/122474
PCT Pub. Date: Aug. 14, 2014

(65) Prior Publication Data
US 2015/0376179 A1 Dec. 31, 2015

Related U.S. Application Data

(60) Provisional application No. 61/868,678, filed on Aug. 22, 2013, provisional application No. 61/762,174, filed on Feb. 7, 2013.

(51) Int. Cl.

| | | |
|---|---|---|
| *A61K 31/4523* | (2006.01) | |
| *C07D 401/14* | (2006.01) | |
| *C07D 417/14* | (2006.01) | |
| *C07D 413/14* | (2006.01) | |
| *C07D 409/14* | (2006.01) | |
| *A61K 31/454* | (2006.01) | |
| *A61K 31/4545* | (2006.01) | |
| *A61K 31/506* | (2006.01) | |
| *A61K 31/55* | (2006.01) | |
| *A61K 45/06* | (2006.01) | |

(52) U.S. Cl.
CPC .......... *C07D 417/14* (2013.01); *A61K 31/454* (2013.01); *A61K 31/4545* (2013.01); *A61K 31/506* (2013.01); *A61K 31/55* (2013.01); *A61K 45/06* (2013.01); *C07D 401/14* (2013.01); *C07D 409/14* (2013.01); *C07D 413/14* (2013.01)

(58) Field of Classification Search
CPC .................................................. C07D 401/14
See application file for complete search history.

(56) References Cited

U.S. PATENT DOCUMENTS

| | | |
|---|---|---|
| 5,889,006 A | 3/1999 | Lowe et al. |
| 6,294,554 B1 | 9/2001 | Clader et al. |
| 6,387,930 B1 | 5/2002 | Baroudy et al. |
| 2002/0156081 A1 | 10/2002 | Hirst et al. |
| 2004/0171614 A1 | 9/2004 | Pissarnitski et al. |
| 2005/0085506 A1 | 4/2005 | Pissarnitski et al. |
| 2006/0276506 A1 | 12/2006 | Yu et al. |
| 2007/0219218 A1 | 9/2007 | Yu et al. |

FOREIGN PATENT DOCUMENTS

| | | |
|---|---|---|
| DE | 4302051 A1 | 7/1994 |
| EP | 1221443 A1 | 7/2002 |
| WO | 9613262 A1 | 5/1996 |
| WO | 9805292 A2 | 2/1998 |
| WO | 9846599 A1 | 10/1998 |
| WO | 99/32481 A1 | 7/1999 |
| WO | 0066559 A1 | 11/2000 |
| WO | 0119829 A2 | 3/2001 |

(Continued)

OTHER PUBLICATIONS

Chapman et al., "The muscarinic M4 receptor is the functionally predominant subtype in rat and mouse striatum as demonstrated using [35S] GTPgammaS binding," European Journal of Pharmacology, 652: 1-6 (2011).

International Search Report and Written Opinion of International Searching Authority for PCT/GB2014/050371, mailed Mar. 19, 2014 (12 pages).

Boyle et al., Benzylidene Ketal Derivatives as M2Muscarinic Receptor Antagonists, Bioorg. & Med. Chem Letters 10 (2000) 2727-2730.

(Continued)

*Primary Examiner* — Brian McDowell
(74) *Attorney, Agent, or Firm* — McCarter & English, LLP; Steven G. Davis; Mei Bai

(57) ABSTRACT

The present invention provides muscarinic M4 receptor agonists of formula (I) and pharmaceutically acceptable salts thereof, wherein m, n, p, q, R, $R^2$ and $R^3$ are as defined in the specification, processes for their preparation, pharmaceutical compositions containing them and their use in the treatment of diseases such as schizophrenia, Alzheimer's disease and various cognitive disorders as well as in the treatment or alleviation of pain.

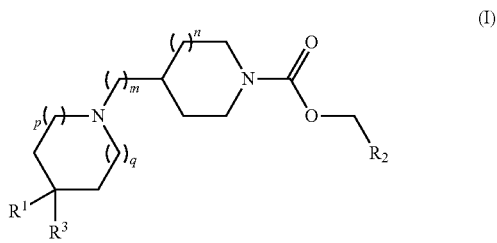

12 Claims, No Drawings

(56) References Cited

FOREIGN PATENT DOCUMENTS

| WO | 0121590 A1 | 3/2001 |
|---|---|---|
| WO | 0127104 A1 | 4/2001 |
| WO | 0132649 A1 | 5/2001 |
| WO | 02076986 A1 | 10/2002 |
| WO | 02080926 A1 | 10/2002 |
| WO | 03066592 A1 | 8/2003 |
| WO | 2004/069828 A1 | 8/2004 |
| WO | 2005030188 A2 | 4/2005 |
| WO | 2005117883 A1 | 12/2005 |
| WO | 2006019768 A1 | 2/2006 |
| WO | 2006/058294 A2 | 6/2006 |
| WO | 2006071958 A1 | 7/2006 |
| WO | 2007142583 A1 | 12/2007 |
| WO | 2008070758 A1 | 6/2008 |
| WO | 2009013171 A2 | 1/2009 |
| WO | 2009/034380 A1 | 3/2009 |
| WO | 2009108117 A1 | 9/2009 |
| WO | 2009131246 A1 | 10/2009 |
| WO | 2011133750 A1 | 10/2011 |
| WO | 2011137012 A1 | 11/2011 |

OTHER PUBLICATIONS

Palani et al., Isopropyl amide derivatives of potent and selective muscarinic M2 receptor antagonists, Bioorg. & Med Chem Letters 14 (2004) 1791-1794.

Palani et al., Synthesis, SAR, and Biological Evaluation of Oximino-Piperidino-Piperidine Amides, J. Med. Chem. (2002) 45: 3143-3160.

Palani et al., Discovery of 4-[(Z)-(4-Bromophenyl)-(ethoxylmino)methyl]-1'[2,4-dimethyl-3-pyridinyl)carbonyl]-4'—methyl-1,4'-bipiperidine N-Oxide (SCH 351125), J. Med. Chem. (2001) 44(21)3339-3342.

Rotstein et al., Synthesis, SAR and evaluation of [1,4']-bipiperidinyl-4-yl-imidazolidin-2-one derivatives as novel CCR5 antagonists, Bioorg. & Med Chem Letters (2010) 20:3219-3222.

Semetey et al., Synthesis and Conformational Study of Water-Soluble, Rigid, Rodlike Oligopiperidines, Angewandte Chemie Int'l Ed (2006) 45:588-591.

PIPERIDIN-1-YL AND AZEPIN-1-YL CARBOXYLATES AS MUSCARINIC M4 RECEPTOR AGONISTS

CROSS-REFERENCE TO RELATED APPLICATIONS

This application is a 35 U.S.C. §371 national stage filing of International Application No. PCT/GB2014/050371, filed on Feb. 7, 2014, which claims the benefit of U.S. Provisional Application No. 61/762,174, filed on Feb. 7, 2013, and U.S. Provisional Application No. 61/868,678, on Aug. 22, 2013. Each of the foregoing applications is incorporated herein by reference in its entirety.

This invention relates to novel piperidine compounds that are agonists of the muscarinic M4 receptor and which are useful in the treatment of muscarinic M4 receptor mediated diseases such as schizophrenia, Alzheimer's disease and various cognitive disorders as well as in the treatment or alleviation of pain. Also provided are pharmaceutical compositions containing the compounds and the therapeutic uses of the compounds.

BACKGROUND OF THE INVENTION

Muscarinic acetylcholine receptors (mAChRs) are members of the G protein-coupled receptor superfamily which mediate the actions of the neurotransmitter acetylcholine in both the central and peripheral nervous system. Five mAChR subtypes have been cloned, $M_1$ to $M_5$. The $M_4$ mAChR is predominantly expressed in the striatum, but also in the hippocampus and cortex; $M_2$ mAChRs are located predominantly in the brainstem and thalamus, though also in the cortex, hippocampus and striatum where they reside on cholinergic synaptic terminals (Langmead et al., 2008 *Br J Pharmacol*). However, $M_2$ mAChRs are also expressed peripherally on cardiac tissue (where they mediate the vagal innervation of the heart) and in smooth muscle and exocrine glands. $M_3$ mAChRs are expressed at relatively low level in the CNS but are widely expressed in smooth muscle and glandular tissues such as sweat and salivary glands (Langmead et al., 2008 *Br J Pharmacol*).

Muscarinic receptors in the central nervous system play a critical role in mediating higher cognitive processing and control of dopamine release. Schizophrenia is a neuropsychiatric disease consisting of multiple symptom domains (positive, negative, cognitive and mood). One of the hypotheses of the disease is that various symptom domains are due to alterations in dopamine signalling, including hyperactivity of the mesolimbic dopamine pathway and hypoactivity of the mesocortical pathway. Muscarinic $M_4$ receptors are expressed pre-synaptically on cholinergic pathways originating in the laterodorsal, subpenduncular and pendunculopontine tegmental nuclei which innervate the substantia nigra and ventral tegmental area (and control dopamine release in the striatum and nucleus accumbens). The absence of the $M_4$ receptor in the KO mouse causes an increase in dopamine efflux in the nucleus accumbens. $M_4$ receptors are also thought to regulate dopamine transmission in the mesocortical pathway.

Furthermore, preclinical studies have suggested that mAChR agonists display an atypical antipsychotic-like profile in a range of pre-clinical paradigms. The mAChR agonist, xanomeline, reverses a number of dopamine driven behaviours, including amphetamine induced locomotion in rats, apomorphine induced climbing in mice, dopamine agonist driven turning in unilateral 6-OH-DA lesioned rats and amphetamine induced motor unrest in monkeys (without EPS liability). It also has been shown to inhibit A10, but not A9, dopamine cell firing and conditioned avoidance and induces c-fos expression in prefrontal cortex and nucleus accumbens, but not in striatum in rats. These data are all suggestive of an atypical antipsychotic-like profile (Mirza et al., 1999 *CNS Drug Rev*).

Xanomeline, sabcomeline, milameline and cevimeline have all progressed into various stages of clinical development for the treatment of Alzheimer's disease and/or schizophrenia. Phase II clinical studies with xanomeline demonstrated its efficacy versus various cognitive symptom domains, including behavioural disturbances and hallucinations associated with Alzheimer's disease (Bodick et al., 1997 *Arch Neurol*). This compound was also assessed in a small Phase II study of schizophrenics and gave a significant reduction in positive and negative symptoms when compared to placebo control (Shekhar et al., 2008 *Am J Psych*). However, in all clinical studies xanomeline and other related mAChR agonists have displayed an unacceptable safety margin with respect to cholinergic side effects, including nausea, gastrointestinal pain, diarrhea, diaphoresis (excessive sweating), hypersalivation (excessive salivation), syncope and bradycardia.

Diseases associated with cognitive impairments, such as Alzheimer's disease, are accompanied by loss of cholinergic neurons in the basal forebrain (Whitehouse et al., 1982 *Science*). In schizophrenia, which is also characterised by cognitive impairments, mAChR density is reduced in the pre-frontal cortex, hippocampus and caudate putamen of schizophrenic subjects (Dean et al., 2002 *Mol Psychiatry*). Furthermore, in animal models, blockade or lesion of central cholinergic pathways results in profound cognitive deficits and non-selective mAChR antagonists have been shown to induce psychotomimetic effects in psychiatric patients. Cholinergic replacement therapy has largely been based on the use of acetylcholinesterase inhibitors to prevent the breakdown of endogenous acetylcholine. These compounds have shown efficacy versus symptomatic cognitive decline in the clinic, but give rise to dose-limiting side effects resulting from stimulation of peripheral $M_2$ and $M_3$ mAChRs including disturbed gastrointestinal motility, bradycardia, nausea and vomiting (http://www.drugs.com/pro/donepezil.html; http://www.drugs.com/pro/rivastigmine.html).

Alzheimer's disease (AD) is the most common neurodegenerative disorder (26.6 million people worldwide in 2006) that affects the elderly, resulting in profound memory loss and cognitive dysfunction. The aetiology of the disease is complex, but is characterised by two hallmark brain sequelae: aggregates of amyloid plaques, largely composed of amyloid-β peptide (Aβ), and neurofibrillary tangles, formed by hyperphosphorylated tau proteins. The accumulation of Aβ is thought to be the central feature in the progression of AD and, as such, many putative therapies for the treatment of AD are currently targeting inhibition of Aβ production. Aβ is derived from proteolytic cleavage of the membrane bound amyloid precursor protein (APP). APP is processed by two routes, nonamyloidgenic and amyloidgenic. Cleavage of APP by γ-secretase is common to both pathways, but in the former APP is cleaved by an α-secretase to yield soluble APPα. The cleavage site is within the Aβ sequence, thereby precluding its formation. However, in the amyloidgenic route, APP is cleaved by β-secretase to yield soluble APPβ and also Aβ. In vitro studies have shown that mAChR agonists can promote the processing of APP toward the soluble, non-amyloidogenic pathway. In vivo studies showed that the mAChR agonist, AF267B, altered diseaselike pathology in the 3×TgAD transgenic mouse, a model of the different components of Alzheimer's disease (Caccamo et al., 2006 *Neuron*). Finally, the mAChR agonist cevimeline has been shown to give a small, but significant, reduction in cerebrospinal fluid levels of Aβ in Alzheimer's patients, thus demonstrating potential disease modifying efficacy (Nitsch et al., 2000 *Neurol*).

Muscarinic agonists have also been disclosed as being useful in the treatment or management of pain, see for example WO2005/030188. The mAChR agonist, xanomeline, has shown to be active in preclinical models of both inflammatory and neuropathic pain (Martino et al., 2012, Pain).

WO2009/108117 and WO2009/034380 (both AstraZeneca) disclose 4-substituted-piperidinylpiperidine carboxylates as muscarinic receptor agonists. The data presented in the two documents indicate that the compounds are selective for the muscarinic M1 receptor and, in most cases, have little or no activity at the M4 receptor.

WO96/13262 (Merck), WO01/21590 (Schering), U.S. Pat. No. 6,294,554 (Schering) and U.S. Pat. No. 5,889,006 (Schering) each disclose 4-substituted-piperidinylpiperidines having muscarinic receptor antagonist activity.

WO98/05292 (Schering) discloses 4-substituted-piperidinylpiperidine carboxylates wherein the 4-substituent can be a phenyl-substituted saturated heterocyclic ring. The compounds are described as having muscarinic antagonist activity.

WO98/46599 (Uriach) discloses piperidinylpiperidinylthiazole carboxamides as platelet aggregation inhibitors.

WO99/32481 (Alcon) discloses piperidinylpiperidinyl carboxylates as muscarinic agents for use in treating glaucoma, myopia and other conditions.

WO2005/117883 (Vertex) discloses muscarinic receptor modulator compounds containing a bridged bicyclic group.

SUMMARY OF THE INVENTION

The present invention provides compounds having activity as muscarinic M4 receptor agonists. More particularly, the invention provides compounds that exhibit selectivity for the M4 receptor relative to the M2 receptor subtype which, as previously mentioned, is expressed peripherally on cardiac tissue. Accordingly, the muscarinic M4 receptor agonists of the invention are advantageous in that they possess a lower cardiovascular risk profile.

In accordance with the present invention, there is therefore provided a compound of formula (I) or a pharmaceutically acceptable salt thereof

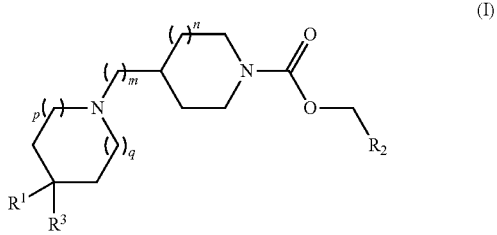

(I)

wherein
m, p and q each independently represent 0 or 1;
n represents an integer 1 or 2;
$R^1$ is selected from hydrogen, fluorine, cyano, hydroxyl, amino (—$NH_2$), and a $C_1$-$C_9$ non-aromatic hydrocarbon group which is optionally substituted with from one to six fluorine atoms and wherein one, two or three carbon atoms of the hydrocarbon group may optionally be replaced by one, two or three heteroatoms independently selected from nitrogen, oxygen and sulphur;
$R^2$ is hydrogen or a $C_1$-$C_6$ non-aromatic hydrocarbon group which is optionally substituted with from one to six fluorine atoms and wherein one, two or three carbon atoms of the hydrocarbon group may optionally be replaced by one, two or three heteroatoms independently selected from nitrogen, oxygen and sulphur;
$R^3$ represents a 5- or 6-membered monocyclic aromatic heterocyclic group containing 1, 2, 3 or 4 ring heteroatoms independently selected from nitrogen, oxygen and sulphur, which heterocyclic group may be optionally substituted by at least one substituent selected from halogen, cyano, oxo, —$NR^4R^5$, —$C(O)NR^6R^7$, $C_1$-$C_6$ haloalkyl, $C_1$-$C_6$ haloalkoxy, —$R^8$, —$OCH_2R^8$, $C_1$-$C_6$ alkoxy, $C_3$-$C_8$ cycloalkyl and $C_1$-$C_6$ alkyl, the alkyl substituent itself being optionally substituted by at least one substituent selected from cyano, —$C(O)NR^9R^{10}$, $C_1$-$C_6$ alkoxy and —$NHC(O)R^{11}$, or
$R^3$ represents a group of formula (II)

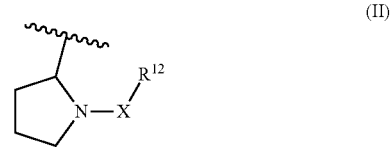

(II)

in which X represents a bond, C(O), C(O)O, C(O)$NR^{13}$ or $SO_2$, and $R^{12}$ represents a $C_1$-$C_6$ alkyl group or a 3- to 10-membered saturated or unsaturated carbocyclic or heterocyclic ring system, each of which may be optionally substituted by at least one substituent selected from halogen, hydroxyl, cyano, oxo, $C_1$-$C_6$ alkyl, $C_2$-$C_6$ alkenyl, $C_1$-$C_6$ haloalkyl, $C_1$-$C_6$ hydroxyalkyl, $C_1$-$C_6$ alkoxy, $C_1$-$C_6$ haloalkoxy, $C_1$-$C_6$ alkylthio, $C_1$-$C_6$ alkylsulphinyl, $C_1$-$C_6$ alkylsulphonyl, $C_1$-$C_6$ alkylcarbonyl, $C_1$-$C_6$ alkylcarbonyloxy, $C_1$-$C_6$ alkoxycarbonyl, —$N(R^{14})_2$, —$CON(R^{15})_2$, $C_3$-$C_6$ cycloalkyl, $C_3$-$C_6$ cycloalkyloxy and $C_3$-$C_6$ cycloalkylmethyl;
$R^4$, $R^5$, $R^6$ and $R^7$ each independently represent a hydrogen atom, $C_1$-$C_6$ alkyl, $C_3$-$C_6$ cycloalkyl or $C_3$-$C_6$ cycloalkylmethyl;
$R^8$ represents a 5- or 6-membered monocyclic aromatic group optionally containing 1, 2, 3 or 4 ring heteroatoms independently selected from nitrogen, oxygen and sulphur, the aromatic group being optionally substituted by at least one substituent selected from halogen and $C_1$-$C_6$ alkyl;
$R^9$, $R^{10}$ and $R^{11}$ each independently represent a hydrogen atom, $C_1$-$C_6$ alkyl or $C_3$-$C_6$ cycloalkyl; and
each $R^{13}$, $R^{14}$ and $R^{15}$ independently represents a hydrogen atom or $C_1$-$C_6$ alkyl group;
but not including the following compounds:
(1) 4-(4-isobutyl-[1,2,3]triazol-1-yl)-[1,4']bipiperidinyl-1'-carboxylic acid ethyl ester,
(2) 4-(4-phenyl-1H-pyrazol-3-yl)-[1,4']bipiperidinyl-1'-carboxylic acid ethyl ester, and
(3) methyl 4-(3-aminopyridin-2-yl)-[1,4'-bipiperidine]-1'-carboxylate.

In the context of the present specification, unless otherwise stated, an "alkyl", "alkenyl" or "alkynyl" substituent group or an alkyl, alkenyl or alkynyl moiety in a substituent group may be linear or branched. Examples of $C_1$-$C_6$ alkyl groups/moieties include methyl, ethyl, propyl, 2-methyl-1-propyl, 2-methyl-2-propyl, 2-methyl-1-butyl, 3-methyl-1-butyl, 2-methyl-3-butyl, 2,2-dimethyl-1-propyl, 2-methyl-pentyl, 3-methyl-1-pentyl, 4-methyl-1-pentyl, 2-methyl-2-pentyl, 3-methyl-2-pentyl, 4-methyl-2-pentyl, 2,2-dimethyl-1-butyl, 3,3-dimethyl-1-butyl, 2-ethyl-1-butyl, n-butyl, isobutyl, tert-butyl, n-pentyl, isopentyl, neopentyl and n-hexyl. Examples of $C_2$-$C_6$ alkenyl groups/moieties include ethenyl, propenyl, 1-butenyl, 2-butenyl, 1-pentenyl, 1-hexenyl, 1,3-butadienyl, 1,3-pentadienyl, 1,4-pentadienyl and 1-hexadienyl. Examples of $C_2$-$C_6$ alkynyl groups/moieties include ethynyl, propynyl, 1-butynyl, 2-butynyl, 1-pentynyl and 1-hexynyl.

The term "non-aromatic hydrocarbon group" refers to a group consisting of carbon and hydrogen atoms and which contains no aromatic rings. The hydrocarbon group may be fully saturated or may contain one or more carbon-carbon double bonds or carbon-carbon triple bonds, or mixtures of double and triple bonds. The hydrocarbon group may be a straight chain or branched chain group or may consist of or contain a cyclic group.

In the definitions of $R^1$ and $R^2$ above, one, two or three, but not all, carbon atoms of the hydrocarbon group may optionally be replaced by a heteroatom selected from nitrogen, oxygen and sulphur. It will be appreciated that when a carbon atom is replaced by a heteroatom, the lower valencies of the heteroatoms compared to carbon means that fewer atoms will be bonded to the heteroatoms than would have been bonded to the carbon atom that has been replaced. Thus, for example, replacement of a carbon atom (valency of four) in a $CH_2$ group by oxygen (valency of two) will mean that the resulting molecule will contain two less hydrogen atoms and replacement of a carbon atom (valency of four) in a $CH_2$ group by nitrogen (valency of three) will mean that the resulting molecule will contain one less hydrogen atom.

Examples of heteroatom replacements for carbon atoms include replacement of a carbon atom in a —$CH_2$—$CH_2$—$CH_2$— chain with oxygen or sulphur to give an ether —$CH_2$—O—$CH_2$— or thioether —$CH_2$—S—$CH_2$—, replacement of a carbon atom in a group $CH_2$—C≡C—H with nitrogen to give a nitrile (cyano) group $CH_2$—C≡N, and replacement of a carbon atom in a —$CH_2$—$CH_2$—$CH_2$— chain with nitrogen to give an amine —$CH_2$—NH—$CH_2$—. In each such replacement, at least one carbon atom of the hydrocarbon group must remain.

If $R^1$ or $R^2$ are heterocyclic, it should be understood that the invention does not encompass any unstable ring structures or any O—O, O—S or S—S bonds and that a substituent, if present, may be attached to any suitable ring atom. Similar comments apply to the optionally substituted 5- or 6-membered monocyclic aromatic heterocyclic group of $R^3$, the optionally substituted 5- or 6-membered monocyclic aromatic group of $R^8$ and the optionally substituted 3- to 10-membered saturated or unsaturated carbocyclic or heterocyclic ring system of $R^{12}$.

A "cycloalkyl" substituent group/moiety is a saturated hydrocarbyl ring containing, for example, from 3 to 8 carbon atoms, examples of which include cyclopropyl, cyclobutyl, cyclopentyl and cyclohexyl.

A "$C_1$-$C_6$ haloalkyl" or "$C_1$-$C_6$ haloalkoxy" substituent group/moiety will comprise at least one halogen atom, e.g. one, two, three, four or five halogen atoms, examples of which include fluoromethyl, difluoromethyl, trifluoromethyl, fluoromethoxy, difluoromethoxy, trifluoromethoxy or pentafluoroethyl.

A "$C_1$-$C_6$ hydroxyalkyl" substituent group/moiety will comprise at least one hydroxyl group, e.g. one, two, three or four hydroxyl groups, examples of which include —$CH_2OH$, —$CH_2CH_2OH$, —$CH_2CH_2CH_2OH$, —$CH(OH)CH_2OH$, —$CH(CH_3)OH$ and —$CH(CH_2OH)_2$.

When any chemical moiety or group in formula (I) is described as being optionally substituted, it will be appreciated that the moiety or group may be either unsubstituted or substituted by one or more of the specified substituents. It will be appreciated that the number and nature of substituents will be selected so as to avoid sterically undesirable combinations.

In an embodiment of the invention, p is 1.
In an embodiment of the invention, q is 1.
In an embodiment of the invention, m is 0.
In an embodiment of the invention, n is 2.
Preferred values for p, q, m and n are shown in the following table:

| p | q | m | n |
|---|---|---|---|
| 1 | 1 | 0 | 1 |
| 1 | 1 | 0 | 2 |
| 0 | 0 | 1 | 1 |
| 0 | 1 | 1 | 1 |

$R^1$ is selected from hydrogen, fluorine, cyano, hydroxyl, amino, and a $C_1$-$C_9$, or $C_1$-$C_6$, or $C_1$-$C_4$, non-aromatic, preferably acyclic, hydrocarbon group which is optionally substituted with from one to six fluorine atoms and wherein one, two or three carbon atoms of the hydrocarbon group may optionally be replaced by one, two or three heteroatoms independently selected from nitrogen, oxygen and sulphur. Preferred such hydrocarbon groups include alkyl and alkoxy groups optionally substituted with from 1 to 6, or 1 to 4, or 1 to 3, fluorine atoms.

In an embodiment of the invention, $R^1$ is selected from hydrogen, fluorine, hydroxyl, $C_1$-$C_4$ alkyl and $C_1$-$C_3$ alkoxy.

In another embodiment, $R^1$ is selected from hydrogen and methoxy.

$R^2$ is hydrogen or a $C_1$-$C_6$, or $C_1$-$C_4$, or $C_1$-$C_2$, non-aromatic, preferably acyclic, hydrocarbon group which is optionally substituted with from one to six fluorine atoms and wherein one, two or three carbon atoms of the hydrocarbon group may optionally be replaced by one, two or three heteroatoms independently selected from nitrogen, oxygen and sulphur. Preferred such hydrocarbon groups include alkyl and alkynyl groups optionally substituted with from 1 to 6, or 1 to 4, or 1 to 3, fluorine atoms.

In an embodiment of the invention, $R^2$ is selected from hydrogen, a $C_1$-$C_3$ alkyl group and a $C_2$-$C_3$ alkynyl group.

In another embodiment of the invention, $R^2$ is selected from hydrogen, methyl, ethyl, ethynyl and 1-propynyl.

In a further embodiment, $R^2$ is methyl.

In one aspect of the invention, $R^3$ may represent a 5- or 6-membered monocyclic aromatic heterocyclic group containing 1, 2, 3 or 4 ring heteroatoms independently selected from nitrogen, oxygen and sulphur, which heterocyclic group may be optionally substituted by at least one substituent (e.g. one, two, three or four substituents independently) selected from halogen (e.g. fluorine, chlorine, bromine or iodine), cyano, oxo, —$NR^4R^5$, —$C(O)NR^6R^7$, $C_1$-$C_6$, or $C_1$-$C_4$, or $C_1$-$C_2$ haloalkyl, $C_1$-$C_6$, or $C_1$-$C_4$, or $C_1$-$C_2$ haloalkoxy, —R⁸, —OCH₂R⁸, $C_1$-$C_6$, or $C_1$-$C_4$, or $C_1$-$C_2$ alkoxy, $C_3$-$C_8$, or $C_3$-$C_6$, cycloalkyl and $C_1$-$C_6$, or $C_1$-$C_4$, or $C_1$-$C_2$ alkyl, the alkyl substituent itself being optionally substituted by at least one substituent (e.g. one, two or three substituents independently) selected from cyano, —C(O)NR⁹R¹⁰, $C_1$-$C_6$, or $C_1$-$C_4$, or $C_1$-$C_2$ alkoxy and —NHC(O)R¹¹.

In particular, R³ may represent a 5- or 6-membered monocyclic aromatic heterocyclic group containing 1, 2, 3 or 4 ring heteroatoms independently selected from nitrogen, oxygen and sulphur, which heterocyclic group may be optionally substituted by one, two, three or four substituents independently selected from fluorine, chlorine, cyano, oxo, —NR⁴R⁵ (e.g. dimethylamino), —C(O)NR⁶R⁷ (e.g. dimethylaminocarbonyl), $C_1$-$C_2$ haloalkyl (e.g. trifluoromethyl), $C_1$-$C_2$ haloalkoxy (e.g. difluoromethoxy or trifluoromethoxy), —R⁸, —OCH₂R⁸, $C_1$-$C_2$ alkoxy, $C_3$-$C_6$ cycloalkyl (e.g. cyclopropyl) and $C_1$-$C_4$ alkyl (e.g. methyl, ethyl, n-propyl and isopropyl), the alkyl substituent itself being optionally substituted by one, two or three substituents independently selected from cyano, —C(O)NR⁹R¹⁰, $C_1$-$C_2$ alkoxy and —NHC(O)R¹¹.

In an embodiment of the invention, R³ represents a 5- or 6-membered monocyclic aromatic heterocyclic group containing 1 or 2 nitrogen ring atoms and optionally one further ring heteroatom selected from oxygen and sulphur, the heterocyclic group being optionally substituted as hereinbefore described.

In one embodiment, R³ represents pyrrolyl, imidazolyl, pyrazolyl, oxazolyl, isoxazolyl, thiazolyl, isothiazolyl, oxadiazolyl, thiadiazolyl, triazolyl, tetrazolyl, pyridinyl, pyrimidinyl or pyrazinyl, each of which is optionally substituted as hereinbefore described.

In another embodiment, R³ represents pyrrolyl, imidazolyl, pyrazolyl, oxadiazolyl, thiazolyl, oxazolyl, pyridinyl, pyrimidinyl or pyrazinyl, each of which is optionally substituted as hereinbefore described.

In another embodiment, R³ represents pyrrolyl, imidazolyl, pyrazolyl, oxadiazolyl, thiazolyl, pyridazinyl, pyridinyl, pyrimidinyl or pyrazinyl, each of which is optionally substituted as hereinbefore described.

Specific examples of R³ substituents include one or more of the following substituents in any combination, in which "a" denotes the point of attachment of R³ to the saturated nitrogen-containing heterocyclic ring:

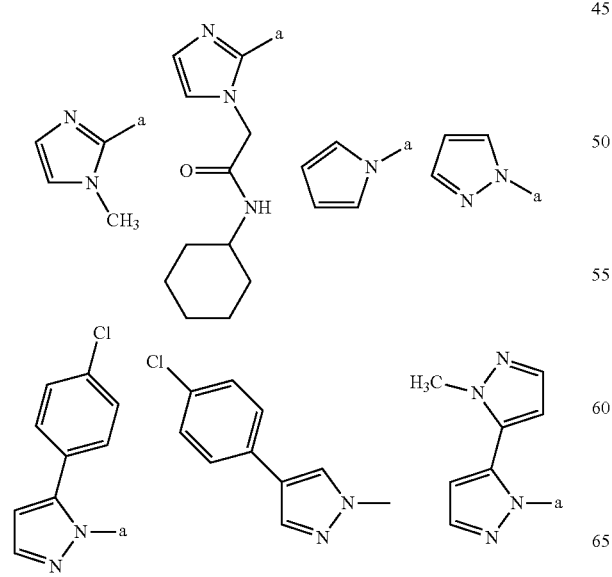

-continued

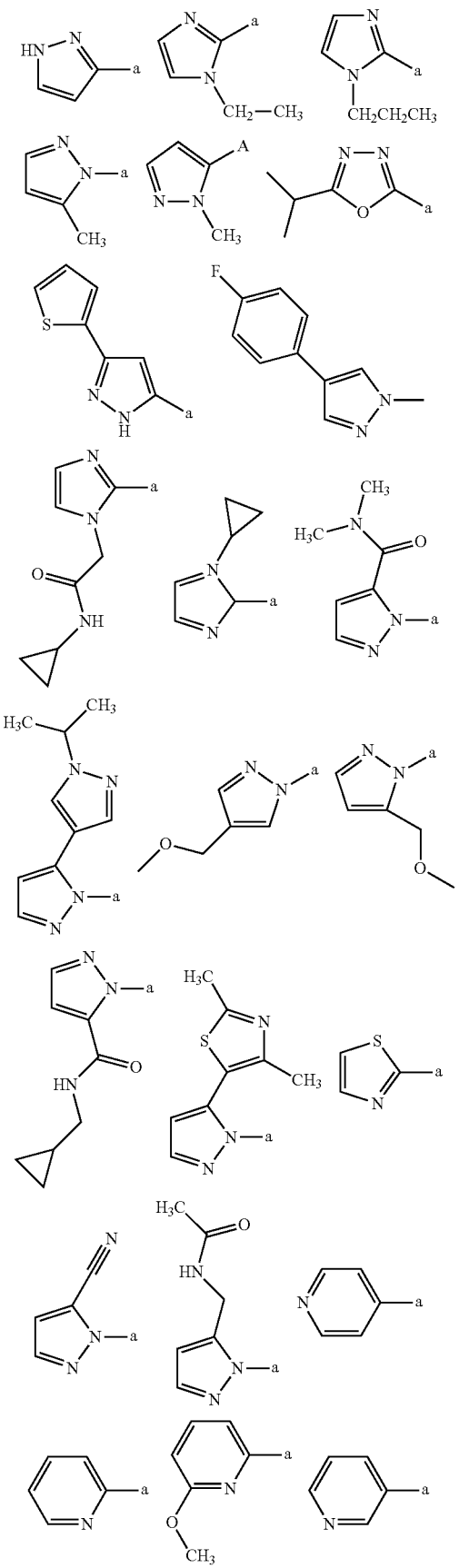

-continued

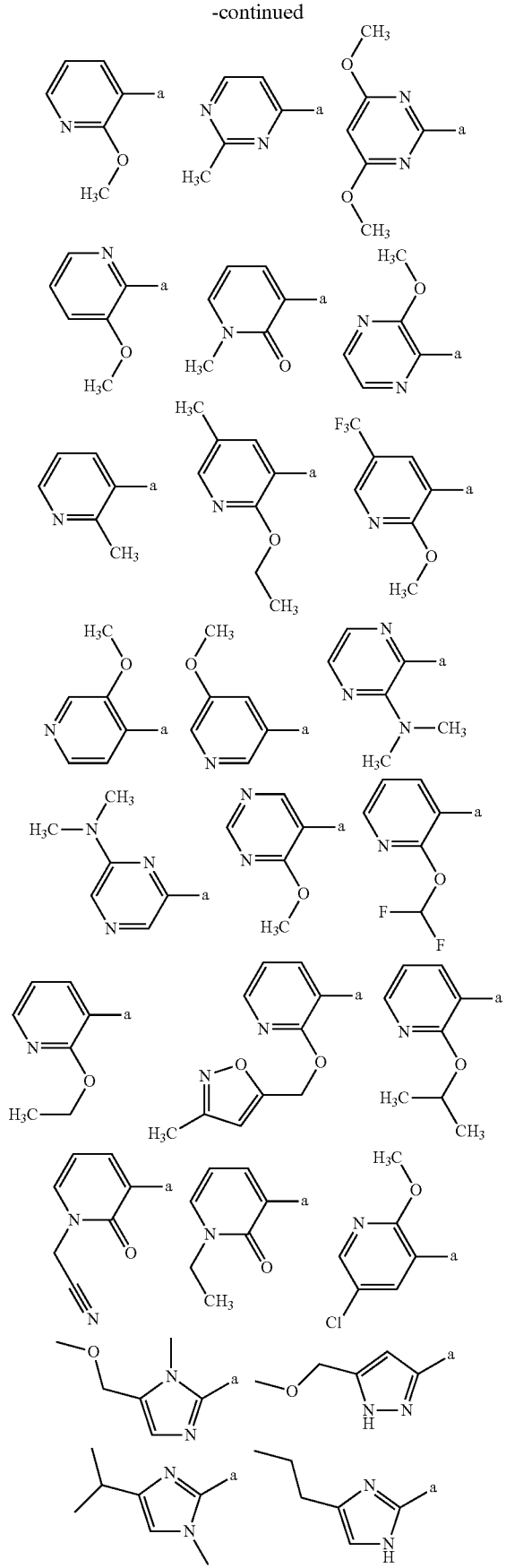

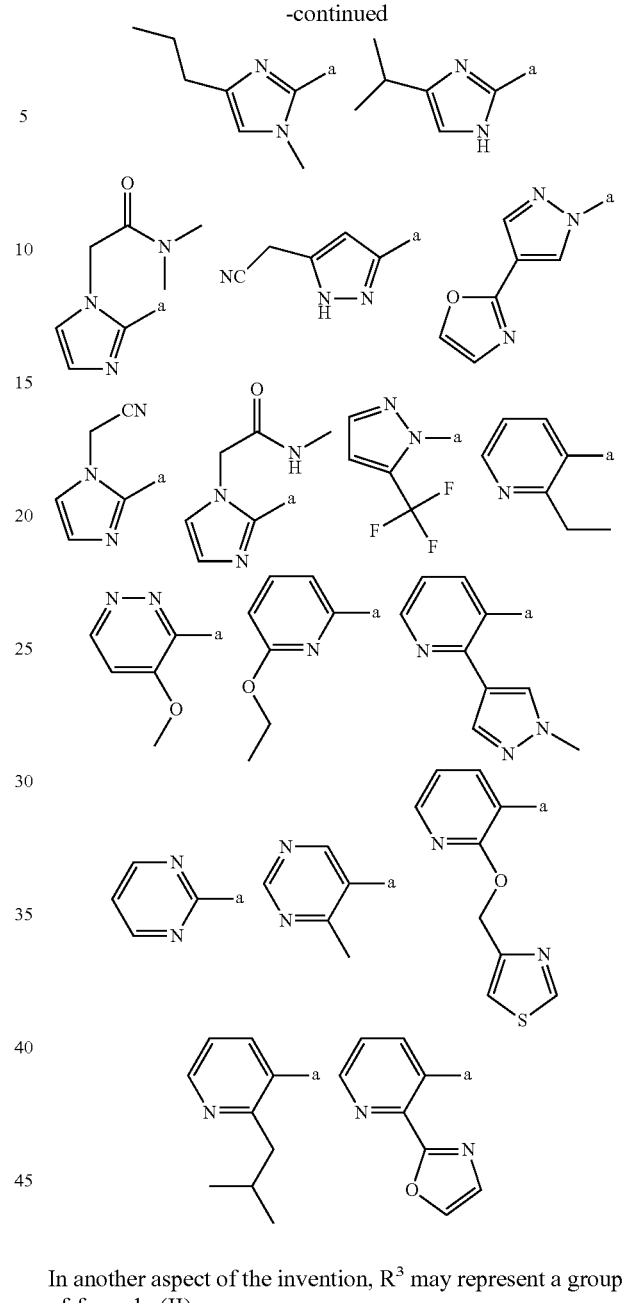

In another aspect of the invention, $R^3$ may represent a group of formula (II)

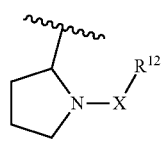

(II)

in which X represents a bond, C(O), C(O)O, C(O)NR$^{13}$ or SO$_2$ and R$^{12}$ represents a C$_1$-C$_6$ alkyl group or a 3- to 10-membered (e.g. 3-, 4-, 5- or 6- to 7-, 8-, 9- or 10-membered) saturated or unsaturated carbocyclic or heterocyclic ring system, each of which may be optionally substituted by at least one substituent (e.g. one, two, three or four substituents independently) selected from halogen (e.g. fluorine, chlorine, bromine or iodine), hydroxyl, cyano, oxo, C$_1$-C$_6$, or $C_1$-$C_4$, or $C_1$-$C_2$ alkyl, $C_2$-$C_6$ or $C_2$-$C_4$ alkenyl, $C_1$-$C_6$, or $C_1$-$C_4$, or $C_1$-$C_2$ haloalkyl, $C_1$-$C_6$, or $C_1$-$C_4$, or $C_1$-$C_2$ hydroxyalkyl, $C_1$-$C_6$, or $C_1$-$C_4$, or $C_1$-$C_2$ alkoxy, $C_1$-$C_6$, or $C_1$-$C_4$, or $C_1$-$C_2$ haloalkoxy, $C_1$-$C_6$, or $C_1$-$C_4$, or $C_1$-$C_2$ alkylthio, $C_1$-$C_6$, or $C_1$-$C_4$, or $C_1$-$C_2$ alkylsulphinyl, $C_1$-$C_6$, or $C_1$-$C_4$, or $C_1$-$C_2$ alkylsulphonyl, $C_1$-$C_6$, or $C_1$-$C_4$, or $C_1$-$C_2$ alkylcarbonyl, $C_1$-$C_6$, or $C_1$-$C_4$, or $C_1$-$C_2$ alkylcarbonyloxy, $C_1$-$C_6$, or $C_1$-$C_4$, or $C_1$-$C_2$ alkoxycarbonyl, —N($R^{14}$)$_2$, —CON($R^{15}$)$_2$, $C_3$-$C_6$ or $C_3$-$C_5$ cycloalkyl, $C_3$-$C_6$ or $C_3$-$C_5$ cycloalkyloxy and $C_3$-$C_6$ or $C_3$-$C_5$ cycloalkylmethyl.

The heterocyclic ring system will comprise at least one ring heteroatom (e.g. one, two, three or four ring heteroatoms independently) selected from nitrogen, sulphur and oxygen.

Examples of saturated or unsaturated 3- to 10-membered carbocyclic or heterocyclic ring systems that may be used, which may be monocyclic or polycyclic (e.g. bicyclic) in which the two or more rings may be fused, bridged or spiro include one or more (in any combination) of cyclopropyl, cyclobutyl, cyclopentyl, cyclohexyl, bicyclo[2.2.1]heptyl, cyclopentenyl, cyclohexenyl, phenyl, pyrrolidinyl, piperidinyl, piperazinyl, morpholinyl, thiomorpholinyl, oxadiazolyl (e.g. 1,2,4-oxadiazolyl), tetrahydrofuranyl, diazabicyclo [2.2.1]hept-2-yl, naphthyl, benzofuranyl, benzothienyl, benzodioxolyl, benzoxazolyl, quinolinyl, oxazolyl, thiadiazolyl (e.g. 1,2,3-thiadiazolyl), 2,3-dihydrobenzofuranyl, tetrahydropyranyl, pyrazolyl, imidazo[1,2-a]pyridinyl, pyrazinyl, thiazolidinyl, indanyl, thienyl, isoxazolyl, pyridazinyl, pyrrolyl, furanyl, thiazolyl, isothiazolyl, indolyl, isoindolyl, imidazolyl, pyrimidinyl, benzimidazolyl, triazolyl, tetrazolyl and pyridinyl.

Preferred ring systems include phenyl, pyridinyl, oxazolyl, pyrazinyl, cyclopropyl, cyclobutyl, cyclopentyl, cyclohexyl, thienyl, tetrahydropyranyl, 2,3-dihydrobenzofuranyl, pyrimidinyl, imidazo[1,2-a]pyridinyl, pyrazolyl, thiazolyl and piperidinyl.

In one embodiment of the invention, $R^{12}$ represents a $C_1$-$C_6$ or $C_1$-$C_4$ alkyl group or a 5- to 6-, 7-, 8- or 9-membered saturated or unsaturated carbocyclic or heterocyclic ring system, each of which may be optionally substituted by at least one substituent (e.g. one, two, three or four substituents independently) selected from halogen (e.g. fluorine, chlorine or bromine), hydroxyl, cyano, oxo, $C_1$-$C_4$ alkyl (e.g. methyl or ethyl), $C_2$-$C_4$ alkenyl (e.g. ethenyl), $C_1$-$C_2$ haloalkyl (e.g. difluoromethyl or trifluoromethyl), $C_1$-$C_2$ hydroxyalkyl (e.g. hydroxymethyl), $C_1$-$C_4$ alkoxy (e.g. methoxy or ethoxy), $C_1$-$C_2$ haloalkoxy (e.g. difluoromethoxy or trifluoromethoxy), $C_1$-$C_4$ alkylthio (e.g. methylthio or ethylthio), $C_1$-$C_4$ alkylsulphinyl (e.g. methylsulphinyl or ethylsulphinyl), $C_1$-$C_4$ alkylsulphonyl (e.g. methylsulphonyl or ethylsulphonyl), $C_1$-$C_4$ alkylcarbonyl (e.g. methylcarbonyl or ethylcarbonyl), $C_1$-$C_4$ alkylcarbonyloxy (e.g. methylcarbonyloxy), $C_1$-$C_4$ alkoxycarbonyl (e.g. methoxycarbonyl), N($R^{14}$)$_2$, —CON($R^{15}$)$_2$, $C_3$-$C_6$ cycloalkyl, $C_3$-$C_6$ cycloalkyloxy and $C_3$-$C_6$ cycloalkylmethyl.

$R^4$, $R^5$, $R^6$ and $R^7$ each independently represent a hydrogen atom, $C_1$-$C_6$, or $C_1$-$C_4$, or $C_1$-$C_2$ alkyl (preferably methyl), $C_3$-$C_6$ or $C_3$-$C_5$ cycloalkyl (e.g. cyclopropyl) or $C_3$-$C_6$ or $C_3$-$C_5$ cycloalkylmethyl (e.g. cyclopropylmethyl).

In an embodiment of the invention, $R^4$, $R^5$, $R^6$ and $R^7$ each independently represent a hydrogen atom, $C_1$-$C_2$ alkyl, $C_3$-$C_5$ cycloalkyl or $C_3$-$C_5$ cycloalkylmethyl.

In another embodiment, $R^4$, $R^5$, $R^6$ and $R^7$ each independently represent a hydrogen atom, or a methyl or cyclopropylmethyl group.

$R^8$ represents a 5- or 6-membered monocyclic aromatic group optionally containing 1, 2, 3 or 4 ring heteroatoms independently selected from nitrogen, oxygen and sulphur, the aromatic group being optionally substituted by at least one substituent (e.g. one, two, three or four substituents independently) selected from halogen (e.g. fluorine, chlorine, bromine or iodine) and $C_1$-$C_6$, or $C_1$-$C_4$, or $C_1$-$C_2$ alkyl.

In one embodiment, $R^8$ represents a 5- or 6-membered monocyclic aromatic group optionally containing 1, 2, 3 or 4 ring heteroatoms independently selected from nitrogen, oxygen and sulphur, the aromatic group being optionally substituted by at least one substituent (e.g. one, two, three or four substituents independently) selected from fluorine, chlorine and $C_1$-$C_4$ alkyl (e.g. methyl, ethyl, n-propyl and isopropyl, preferably methyl).

In a further embodiment, $R^8$ represents pyrrolyl, imidazolyl, pyrazolyl, oxazolyl, thienyl, isoxazolyl, thiazolyl, isothiazolyl, oxadiazolyl, thiadiazolyl, triazolyl, tetrazolyl, phenyl, pyridinyl, pyrimidinyl or pyrazinyl, each of which is optionally substituted as hereinbefore described.

In a still further embodiment, $R^8$ represents a 5- or 6-membered monocyclic aromatic group optionally containing 1 or 2 ring heteroatoms independently selected from nitrogen, oxygen and sulphur (such as phenyl, pyrazolyl, thienyl, thiazolyl or oxazolyl), the aromatic group being optionally substituted as hereinbefore described.

$R^9$, $R^{10}$ and $R^{11}$ each independently represent a hydrogen atom, $C_1$-$C_6$, or $C_1$-$C_4$, or $C_1$-$C_2$ alkyl (preferably methyl) or $C_3$-$C_6$ cycloalkyl (e.g. cyclopropyl or cyclohexyl).

In one embodiment, $R^9$, $R^{10}$ and $R^{11}$ each independently represent a hydrogen atom, or a methyl, cyclopropyl or cyclohexyl group.

Each $R^{13}$, $R^{14}$ and $R^{15}$ independently represents a hydrogen atom or a $C_1$-$C_6$, or $C_1$-$C_4$, or $C_1$-$C_2$ alkyl (preferably methyl) group.

In a preferred embodiment of the invention, subject to the above provisos:
  m, p and q each independently represent 0 or 1;
  n represents an integer 1 or 2;
  $R^1$ is selected from hydrogen and methoxy;
  $R^2$ is hydrogen or methyl;
  $R^3$ represents a 5- or 6-membered monocyclic aromatic heterocyclic group containing 1, 2 or 3 ring heteroatoms independently selected from nitrogen, oxygen and sulphur, which heterocyclic group may be optionally substituted by at least one substituent (e.g. one, two, three or four substituents independently) selected from fluorine, chlorine, cyano, oxo, —NR$^4$R$^5$, —C(O)NR$^6$R$^7$, trifluoromethyl, difluoromethoxy, trifluoromethoxy, —R$^8$, —OCH$_2$R$^8$, $C_1$-$C_2$ alkoxy, cyclopropyl and $C_1$-$C_4$ alkyl, the alkyl substituent itself being optionally substituted by one, two or three substituents independently selected from cyano, —C(O)NR$^9$R$^{10}$, $C_1$-$C_2$ alkoxy and —NHC(O)R$^{11}$;
  $R^4$, $R^5$, $R^6$ and $R^7$ each independently represent a hydrogen atom, or a methyl or cyclopropylmethyl group;
  $R^8$ represents a 5- or 6-membered monocyclic aromatic group optionally containing 1 or 2 ring heteroatoms independently selected from nitrogen, oxygen and sulphur, the aromatic group being optionally substituted by at least one substituent (e.g. one or two substituents independently) selected from fluorine, chlorine and $C_1$-$C_3$ alkyl; and
  $R^9$, $R^{10}$ and $R^{11}$ each independently represent a hydrogen atom, or a methyl, cyclopropyl or cyclohexyl group.

Examples of compounds of the invention include:
Ethyl 4-[4-(1-methyl-1H-imidazol-2-yl)piperidin-1-yl]piperidine-1-carboxylate,
Ethyl 4-(4-{1-[(cyclohexylcarbamoyl)methyl]-1H-imidazol-2-yl}piperidin-1-yl)azepane-1-carboxylate,
Ethyl 4-[4-(1H-pyrrol-1-yl)piperidin-1-yl]azepane-1-carboxylate,
Ethyl 4-[4-(1H-pyrazol-1-yl)piperidin-1-yl]azepane-1-carboxylate,
Ethyl 4-{4-[5-(4-chlorophenyl)-1H-pyrazol-1-yl]piperidin-1-yl}azepane-1-carboxylate,
Ethyl 4-[4-(1H-pyrazol-3-yl)piperidin-1 yl]azepane-1-carboxylate,
Ethyl 4-{4-[5-(1-methyl-1H-pyrazol-5-yl)-1H-pyrazol-1-yl]piperidin-1-yl}azepane-1-carboxylate,
Ethyl 4-{4-[4-(4-chlorophenyl)-1H-pyrazol-1-yl]piperidin-1-yl}azepane-1-carboxylate,
Ethyl 4-[4-(1-methyl-1H-imidazol-2-yl)piperidin-1-yl]azepane-1-carboxylate,
Ethyl 4-[4-(1-ethyl-1H-imidazol-2-yl)piperidin-1-yl]azepane-1-carboxylate,
Ethyl 4-[4-(1-propyl-1H-imidazol-2-yl)piperidin-1-yl]azepane-1-carboxylate,
Ethyl 4-[4-(5-methyl-1H-pyrazol-1-yl)piperidin-1-yl]azepane-1-carboxylate,
Ethyl 4-[4-methoxy-4-(1-methyl-1H-imidazol-2-yl)piperidin-1-yl]azepane-1-carboxylate,
Ethyl 4-[4-(1-methyl-1H-pyrazol-5-yl)piperidin-1-yl]azepane-1-carboxylate,
Ethyl 4-(4-(5-isopropyl-1,3,4-oxadiazol-2-yl)piperidin-1-yl)azepane-1-carboxylate,
Ethyl 4-[4-(3-methyl-1H-pyrazol-1-yl)piperidin-1-yl]azepane-1-carboxylate,
Ethyl 4-{4-[3-(thiophen-2-yl)-1H-pyrazol-5-yl]piperidin-1-yl}azepane-1-carboxylate,
Ethyl 4-{4-[4-(4-fluorophenyl)-1H-pyrazol-1-yl]piperidin-1-yl}azepane-1-carboxylate,
Ethyl 4-(4-{1-[(cyclopropylcarbamoyl)methyl]-1H-imidazol-2-yl}piperidin-1-yl)azepane-1-carboxylate,
Ethyl 4-[4-(5-cyclopropyl-1H-pyrazol-1-yl)piperidin-1-yl]azepane-1-carboxylate,
Ethyl 4-{4-[5-(dimethylcarbamoyl)-1H-pyrazol-1-yl]piperidin-1-yl}azepane-1-carboxylate,
Ethyl 4-(4-{5-[1-(propan-2-yl)-1H-pyrazol-4-yl]-1H-pyrazol-1-yl}piperidin-1-yl)azepane-1-carboxylate,
Ethyl 4-{4-[5-(methoxymethyl)-1H-pyrazol-1-yl]piperidin-1-yl}azepane-1-carboxylate,
Ethyl 4-(4-{5-[(cyclopropylmethyl)carbamoyl]-1H-pyrazol-1-yl}piperidin-1-yl)azepane-1-carboxylate,
Ethyl 4-{4-[5-(dimethyl-1,3-thiazol-5-yl)-1H-pyrazol-1-yl]piperidin-1-yl}azepane-1-carboxylate,
Ethyl 4-[4-(1,3-thiazol-2-yl)piperidin-1-yl]azepane-1-carboxylate,
Ethyl 4-[4-(5-cyano-1H-pyrazol-1-yl)piperidin-1-yl]azepane-1-carboxylate,
Ethyl 4-{4-[5-(acetamidomethyl)-1H-pyrazol-1-yl]piperidin-1-yl}azepane-1-carboxylate,
Ethyl 4-{[3-(1H-pyrazol-1-yl)azetidin-1-yl]methyl}piperidine-1-carboxylate,
Ethyl 4-[4-(pyridin-4-yl)piperidin-1-yl]azepane-1-carboxylate,
Ethyl 4-[4-(pyridin-4-yl)piperidin-1-yl]piperidine-1-carboxylate,
Ethyl 4-[4-(6-methoxypyridin-2-yl)piperidin-1-yl]piperidine-1-carboxylate,
Ethyl 4-[4-(6-methoxypyridin-2-yl)piperidin-1-yl]azepane-1-carboxylate,
Ethyl 4-[4-(2-methoxypyridin-3-yl)piperidin-1-yl]piperidine-1-carboxylate,
Ethyl 4-[4-(2-methoxypyridin-3-yl)piperidin-1-yl]azepane-1-carboxylate,
Ethyl 4-[4-(2-methylpyrimidin-4-yl)piperidin-1-yl]piperidine-1-carboxylate,
Ethyl 4-[4-(4,6-dimethoxypyrimidin-2-yl)piperidin-1-yl]piperidine-1-carboxylate,
Ethyl 4-[4-(3-methoxypyridin-2-yl)piperidin-1-yl]azepane-1-carboxylate,
Ethyl 4-[4-(1-methyl-2-oxo-1,2-dihydropyridin-3-yl)piperidin-1-yl]azepane-1-carboxylate,
Ethyl 4-[4-(3-methoxypyrazin-2-yl)piperidin-1-yl]azepane-1-carboxylate,
Ethyl 4-[4-(2-methylpyridin-3-yl)piperidin-1-yl]azepane-1-carboxylate,
Ethyl 4-[4-(2-ethoxy-5-methylpyridin-3-yl)piperidin-1-yl]azepane-1-carboxylate,
Ethyl 4-{4-[2-methoxy-5-(trifluoromethyl)pyridin-3-yl]piperidin-1-yl}azepane-1-carboxylate,
Ethyl 4-[4-(3-methoxypyridin-4-yl)piperidin-1-yl]azepane-1-carboxylate,
Ethyl 4-[4-(5-methoxypyridin-3-yl)piperidin-1-yl]azepane-1-carboxylate,
Ethyl 4-[4-(2-methylpyridin-3-yl)piperidin-1-yl]piperidine-1-carboxylate,
Ethyl 4-[4-(2-ethoxy-5-methylpyridin-3-yl)piperidin-1-yl]piperidine-1-carboxylate,
Ethyl 4-[4-(4-methoxypyridin-3-yl)piperidin-1-yl]azepane-1-carboxylate,
Ethyl 4-{4-[3-(dimethylamino)pyrazin-2-yl]piperidin-1-yl}azepane-1-carboxylate,
Ethyl 4-{4-[6-(dimethylamino)pyrazin-2-yl]piperidin-1-yl}azepane-1-carboxylate,
Ethyl 4-[4-(4-methoxypyrimidin-5-yl)piperidin-1-yl]azepane-1-carboxylate,
Ethyl 4-{4-[2-(difluoromethoxy)pyridin-3-yl]piperidin-1-yl}azepane-1-carboxylate,
Ethyl 4-[4-(2-ethoxypyridin-3-yl)piperidin-1-yl]azepane-1-carboxylate,
Ethyl 4-(4-{2-[(3-methyl-1,2-oxazol-5-yl)methoxy]pyridin-3-yl}piperidin-1-yl)azepane-1-carboxylate,
Ethyl 4-{4-[2-(propan-2-yloxy)pyridin-3-yl]piperidin-1-yl}azepane-1-carboxylate,
Ethyl 4-{4-[1-(cyanomethyl)-2-oxo-1,2-dihydropyridin-3-yl]piperidin-1-yl}azepane-1-carboxylate,
Ethyl 4-[4-(1-ethyl-2-oxo-1,2-dihydropyridin-3-yl)piperidin-1-yl]azepane-1-carboxylate,
Ethyl 4-[4-(5-chloro-2-methoxypyridin-3-yl)piperidin-1-yl]azepane-1-carboxylate,
Ethyl 4-[4-(3,6-dimethylpyrazin-2-yl)piperidin-1-yl]azepane-1-carboxylate,
Ethyl 4-{4-[5-methoxy-2-(trifluoromethyl)pyrimidin-4-yl]piperidin-1-yl}azepane-1-carboxylate,
Ethyl 4-(4-{2-[1-(propan-2-yl)-1H-pyrazol-4-yl]pyridin-3-yl}piperidin-1-yl)azepane-1-carboxylate,
Ethyl 4-{4-[2-(methylamino)pyridin-3-yl]piperidin-1-yl}azepane-1-carboxylate,
Ethyl 4-[4-(5-methoxy-2-methylpyrimidin-4-yl)piperidin-1-yl]azepane-1-carboxylate,
Ethyl 4-{4-[2-(1-methyl-1H-pyrazol-5-yl)pyridin-3-yl]piperidin-1-yl}azepane-1-carboxylate,
Ethyl 4-{4-[2-(dimethylamino)pyridin-3-yl]piperidin-1-yl}azepane-1-carboxylate,
Ethyl 4-[4-(2-cyclopropylpyridin-3-yl)piperidin-1-yl]azepane-1-carboxylate, Ethyl 4-(4-{2-[(cyclopropylmethyl)amino]pyridin-3-yl}piperidin-1-yl)azepane-1-carboxylate,
Ethyl 4-[4-(1,3-thiazol-2-yl)piperidin-1-yl]piperidine-1-carboxylate,
Ethyl 4-{4-[5-(trifluoromethyl)-1H-pyrazol-1-yl]piperidin-1-yl}azepane-1-carboxylate,
Ethyl 4-[4-(2-ethylpyridin-3-yl)piperidin-1-yl]azepane-1-carboxylate,
Ethyl 4-[4-(4-methoxypyridazin-3-yl)piperidin-1-yl]azepane-1-carboxylate,
Ethyl 4-[4-(6-ethoxypyridin-2-yl)piperidin-1-yl]piperidine-1-carboxylate,
Ethyl 4-{4-[2-(1-methyl-1H-pyrazol-4-yl)pyridin-3-yl]piperidin-1-yl}azepane-1-carboxylate,
Ethyl 4-[4-(pyrimidin-2-yl)piperidin-1-yl]azepane-1-carboxylate,
Ethyl 4-[4-(4-methylpyrimidin-5-yl)piperidin-1-yl]azepane-1-carboxylate,
Ethyl 4-{4-[2-(1,3-thiazol-4-ylmethoxy)pyridin-3-yl]piperidin-1-yl}azepane-1-carboxylate,
Ethyl 4-{4-[2-(2-methylpropyl)pyridin-3-yl]piperidin-1-yl}azepane-1-carboxylate,
Methyl 4-{[3-(3,5-dimethyl-1H-pyrazol-1-yl)pyrrolidin-1-yl]methyl}piperidine-1-carboxylate,
Ethyl 4-{[3-(3,5-dimethyl-1H-pyrazol-1-yl)pyrrolidin-1-yl]methyl}piperidine-1-carboxylate,
Ethyl 4-{4-[2-(1,3-oxazol-2-yl)pyridin-3-yl]piperidin-1-yl}azepane-1-carboxylate,
Ethyl (4S)-4-[4-(1H-pyrazol-1-yl)piperidin-1-yl]azepane-1-carboxylate,
Ethyl (4R)-4-[4-(1H-pyrazol-1-yl)piperidin-1-yl]azepane-1-carboxylate,
Ethyl (4S)-4-[4-(1-methyl-1H-imidazol-2-yl)piperidin-1-yl]azepane-1-carboxylate,
Ethyl (4R)-4-[4-(1-methyl-1H-imidazol-2-yl)piperidin-1-yl]azepane-1-carboxylate,
Ethyl (4S)-4-[4-(2-methoxypyridin-3-yl)piperidin-1-yl]azepane-1-carboxylate,
Ethyl (4R)-4-[4-(2-methoxypyridin-3-yl)piperidin-1-yl]azepane-1-carboxylate,
and pharmaceutically acceptable salts of any one thereof.

It should be noted that each of the chemical compounds listed above represents a particular and independent aspect of the invention.

The present invention further provides a process for the preparation of a compound of formula (I) or a pharmaceutically acceptable salt thereof as defined above which comprises
(i) reacting a compound of formula (X),

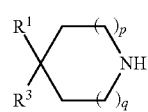
(X)

wherein p, q, $R^1$ and $R^3$ are as defined in formula (I), with a compound of formula (XIa) or (XIb),

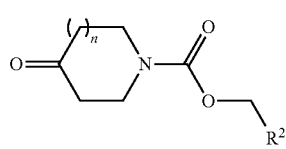
(XIa)

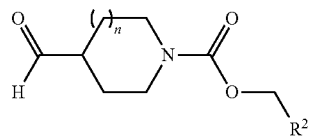
(XIb)

wherein n and $R^2$ are as defined in formula (I), under reductive amination conditions; or
(ii) when $R^3$ represents a 1,3,4-oxadiazolyl-2-yl group, reacting a compound of formula (XII),

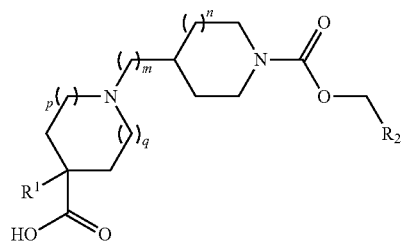
(XII)

wherein m, n, p, q, $R^1$ and $R^2$ are as defined in formula (I), with a compound of formula (XIII), R—C(O)—NH—NH$_2$, wherein R represents hydrogen or an $R^3$ substituent as hereinbefore defined, in the presence of a base followed by reaction with a dehydrating agent such as Burgess's reagent;
and optionally thereafter carrying out one or more of the following procedures:
converting a compound of formula (I) into another compound of formula (I)
removing any protecting groups
forming a pharmaceutically acceptable salt.

In process variant (i), the reductive amination reaction is typically carried out at ambient temperature using a borohydride reducing agent such as sodium triacetoxy-borohydride in a solvent such as dichloromethane or dichloroethane containing acetic acid.

Intermediate compounds of formula (X) can be prepared by the series of reactions shown in Scheme 1 below.

Scheme 1

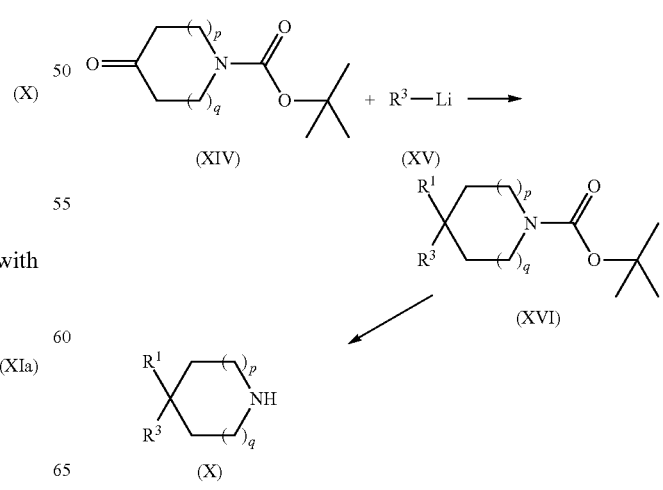

In Scheme 1, a heterocycle $R^3$—H (e.g. 1-methyl imidazole) is metallated using a reagent such as lithium diisopropylamide (LDA) or n-butyl lithium (n-BuLi) in an inert solvent such as hexane or tetrahydrofuran (THF), and the resulting intermediate of formula (XV), $R^3$—Li, is then reacted with a compound of formula (XIV) in which p and q are as defined in formula (I), e.g. N-Boc piperidin-4-one, to give a hydroxyl compound (formula (XVI), $R^1$=hydroxy). The hydroxyl compound (formula (XVI), $R^1$=hydroxy) can then be modified further by: (a) reacting it with a base such as sodium hydride and then an alkyl halide such as iodomethane in a solvent such as DMF to give the corresponding methoxy compound (formula (XVI), $R^1$=OCH$_3$); or (b) reacting it with a fluorinating agent such as diethylaminosulphur trifluoride (DAST) in a solvent such as dichloromethane to give the fluoro compound (formula (XVI), $R^1$=F). The compound of formula (XVI) ($R^1$=OH, OCH$_3$ or F) is then deprotected by removal of the Boc group using an organic acid such as trifluoroacetic acid in dichloromethane or an inorganic acid such as HCl in dioxane to give the compound, e.g. substituted piperidine, of formula (X).

Intermediate compounds of the formula (XVI) wherein $R^3$ contains an N—H ring member can be alkylated to give the corresponding compound wherein the hydrogen atom has been replaced by an alkyl group. The alkylation step is typically accomplished using a base such as sodium hydride or potassium carbonate in an inert solvent such as DMF or acetonitrile and then reacting it with an alkyl halide. Thereafter, the alkylated compound of formula (XVI) can be deprotected using an inorganic acid such as hydrochloric acid in dioxane or an organic acid such as trifluoroacetic acid in dichloromethane to give the compound of formula (X).

Intermediate compounds of formula (X) may also be prepared by the series of reactions shown in Scheme 2 below.

Scheme 2

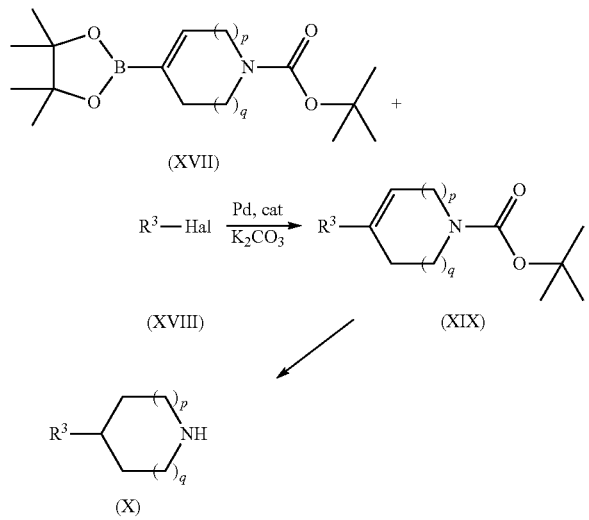

In Scheme 2, the boronate ester (XVII) is reacted under Suzuki reaction conditions with the heteroaryl halide of formula (XVIII) (e.g. bromide or iodide) to give the Boc-protected intermediate of formula (XIX). The reaction is typically conducted in the presence of a palladium catalyst such as PdCl$_2$(DPPF) (1,1'-bis(diphenylphosphino)ferrocene]-dichloropalladium(II)) or Pd(Amphos)$_2$ (bis(di-tert-butyl(4-dimethylaminophenyl)-phosphine)dichloropalladium(II)) and a base such as potassium carbonate in a polar solvent such as aqueous dioxane. The intermediate compound of formula (XIX) can be hydrogenated using hydrogen and a catalyst such as palladium on carbon prior to deprotection by treatment with an acid such as hydrochloric acid to give the compound of formula (X).

Compounds of formula (XII) can be prepared by the reaction of a compound of formula (XIa) or (XIb) with a compound of formula (XX):

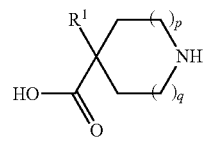

under reductive amination conditions as described above in relation to process variant (i).

In an alternative sequence of reactions, an ester (e.g. the ethyl ester) of the carboxylic acid of formula (XX) is reacted with the compound of formula (XIa) or (XIb) in the presence of either sodium cyanoborohydride in combination with zinc chloride or sodium triacetoxyborohydride in combination with titanium isopropoxide to give an intermediate ester compound (not shown) which is then selectively hydrolysed under mild conditions using lithium hydroxide or sodium hydroxide to give the compound of formula (XII).

In process variant (ii), in an initial step, an intermediate compound of formula (XII) is reacted with a compound of the formula (XIII), R—C(O)—NH—NH$_2$, in the presence of a reagent suitable for promoting the formation of an amide bond to give an intermediate product which undergoes a cyclodehydration in the presence of a dehydrating agent such as Burgess's reagent (methyl N-(triethylammonium-sulphonyl)carbamate) to give the oxadiazole.

Examples of reagents suitable for promoting the formation of an amide bond include 1,3-dicyclohexylcarbodiimide (DCC) (Sheehan et al, *J. Amer. Chem Soc.* 1955, 77, 1067), 1-ethyl-3-(3'-dimethylaminopropyl)-carbodiimide (referred to herein either as EDC or EDAC) (Sheehan et al, *J. Org. Chem.*, 1961, 26, 2525), uronium-based coupling agents such as O-(7-azabenzotriazol-1-yl)-N,N,N',N'-tetramethyluronium hexafluorophosphate (HATU) and phosphonium-based coupling agents such as 1-benzo-triazolyloxytris-(pyrrolidino)phosphonium hexafluorophosphate (PyBOP) (Castro et al, *Tetrahedron Letters,* 1990, 31, 205). Carbodiimide-based coupling agents are advantageously used in combination with 1-hydroxy-7-azabenzotriazole (HOAt) (L. A. Carpino, *J. Amer. Chem. Soc.,* 1993, 115, 4397) or 1-hydroxybenzotriazole (HOBt) (Konig et al, *Chem. Ber.,* 103, 708, 2024-2034). A preferred amide coupling agent is HATU.

The amide coupling reaction is typically carried out in a non-aqueous, non-protic solvent such as acetonitrile, dioxane, dimethylsulphoxide, dichloromethane, dimethylformamide or N-methylpyrrolidinone, or in an aqueous solvent optionally together with one or more miscible co-solvents. The reaction can be carried out at room temperature or, where the reactants are less reactive at an appropriately elevated temperature, for example a temperature up to about 100° C., e.g. from 50° C. to 80° C. The reaction may optionally be carried out in the presence of a non-interfering base, for example a tertiary amine such as triethylamine or N,N-diisopropylethylamine.

As an alternative, a reactive derivative of the carboxylic acid of formula (XII), e.g. an anhydride or acid chloride, may be used. The acid chloride is typically reacted with the compound of formula (XIII), R—C(O)NHNH$_2$, in the presence of a base such as sodium bicarbonate. The acid chloride can be prepared using standard methods, for example by treatment of the acid with oxalyl chloride in the presence of a catalytic amount of dimethylformamide.

Compounds of formulae (XIa), (XIb), (XIII), (XIV), (XV), (XVII), (XVIII) and (XX) are either commercially available, are well known in the literature or may be prepared using known techniques.

It will be appreciated by those skilled in the art that in the processes of the present invention certain functional groups such as phenol, hydroxyl or amino groups in the reagents may need to be protected by protecting groups. Thus, the preparation of the compounds of formula (I) may involve, at an appropriate stage, the removal of one or more protecting groups.

The protection and deprotection of functional groups is described in 'Protective Groups in Organic Chemistry', edited by J. W. F. McOmie, Plenum Press (1973) and 'Protective Groups in Organic Synthesis', 3$^{rd}$ edition, T. W. Greene and P. G. M. Wuts, Wiley-Interscience (1999).

The compounds of formula (I) above may be converted to a pharmaceutically acceptable salt thereof, preferably an acid addition salt such as a hydrochloride, hydrobromide, benzenesulphonate (besylate), saccharin (e.g. monosaccharin), trifluoroacetate, sulphate, nitrate, phosphate, acetate, fumarate, maleate, tartrate, lactate, citrate, pyruvate, succinate, valerate, propanoate, butanoate, malonate, oxalate, 1-hydroxy-2-napthoate (xinafoate), methanesulphonate or p-toluenesulphonate salt.

In one aspect of the invention, compounds of formula (I) may bear one or more radiolabels. Such radiolabels may be introduced by using radiolabel-containing reagents in the synthesis of the compounds of formula (I), or may be introduced by coupling the compounds of formula (I) to chelating moieties capable of binding to a radioactive metal atom. Such radiolabeled versions of the compounds may be used, for example, in diagnostic imaging studies.

Compounds of formula (I) and their salts may be in the form of hydrates or solvates which form an aspect of the present invention. Such solvates may be formed with common organic solvents, including but not limited to, alcoholic solvents e.g. methanol, ethanol or isopropanol.

Where compounds of formula (I) are capable of existing in stereoisomeric forms, it will be understood that the invention encompasses the use of all geometric and optical isomers (including atropisomers) of the compounds of formula (I) and mixtures thereof including racemates. The use of tautomers and mixtures thereof also form an aspect of the present invention. Enantiomerically pure forms are particularly desired.

The compounds of formula (I) and their pharmaceutically acceptable salts have activity as pharmaceuticals, in particular as M4 receptor agonists, and thus may be used in the treatment of schizophrenia, schizophreniform disorder, schizoaffective disorder, bipolar disorders including bipolar I and II, bipolar mania and bipolar depression, cognitive disorders (such as dementia and impaired learning), disorders usually first diagnosed in infancy, childhood, or adolescence (e.g., attention-deficit disorder and disruptive behaviour disorders), pain (e.g. neuropathic pain), neurodegenerative disorders (e.g. Alzheimer's disease), drug abuse (such as cocaine abuse) and autism.

Thus, the present invention provides a compound of formula (I) or a pharmaceutically acceptable salt thereof as hereinbefore defined for use in therapy, in particular for the treatment of conditions whose development or symptoms are linked to M4 receptor activity.

The present invention also provides the use of a compound of formula (I) or a pharmaceutically acceptable salt thereof as hereinbefore defined for the preparation of a medicament for the treatment of conditions whose development or symptoms are linked to M4 receptor activity.

In the context of the present specification, the term "therapy" also includes "prophylaxis" unless there are specific indications to the contrary. The terms "therapeutic" and "therapeutically" should be construed accordingly.

Prophylaxis is expected to be particularly relevant to the treatment of persons who have suffered a previous episode of, or are otherwise considered to be at increased risk of, the disorder or condition in question. Persons at risk of developing a particular disorder or condition generally include those having a family history of the disorder or condition, or those who have been identified by genetic testing or screening to be particularly susceptible to developing the disorder or condition or those in the prodromal phase of a disorder.

In particular, the compounds of the invention (including pharmaceutically acceptable salts) may be used in the treatment of the positive symptoms of schizophrenia, schizophreniform disorder or schizoaffective disorder (e.g. voices or hallucinations), cognitive disorders (such as dementia and impaired learning), pain (such as neuropathic pain), drug abuse (such as cocaine abuse) and bipolar disorders.

The invention also provides a method of treating at least one symptom or condition associated with schizophrenia, schizophreniform disorder, schizoaffective disorder, bipolar disorders including bipolar I and II, bipolar mania and bipolar depression, cognitive disorders (such as dementia and impaired learning), disorders usually first diagnosed in infancy, childhood, or adolescence (e.g., attention-deficit disorder and disruptive behaviour disorders), pain (e.g. neuropathic pain), neurodegenerative disorders (e.g. Alzheimer's disease), drug abuse (such as cocaine abuse) and autism which comprises administering to a patient in need thereof a therapeutically effective amount of a compound of formula (I) or a pharmaceutically acceptable salt thereof as hereinbefore defined.

Such symptoms and conditions include, but are not limited to, anxiety, agitation, hostility, panic, an eating disorder, an affective symptom, a mood symptom, a negative and positive psychotic symptom commonly associated with psychosis and neurodegenerative disorder.

For the above-mentioned therapeutic uses the dosage administered will, of course, vary with the compound employed, the mode of administration, the treatment desired and the disorder indicated. For example, the daily dosage of the compound of the invention, if inhaled, may be in the range from 0.05 micrograms per kilogram body weight (μg/kg) to 100 micrograms per kilogram body weight (μg/kg). Alternatively, if the compound is administered orally, then the daily dosage of the compound of the invention may be in the range from 0.01 micrograms per kilogram body weight (μg/kg) to 100 milligrams per kilogram body weight (mg/kg).

The compounds of formula (I) and pharmaceutically acceptable salts thereof may be used on their own but will generally be administered in the form of a pharmaceutical composition in which the formula (I) compound/salt (active ingredient) is in association with a pharmaceutically acceptable adjuvant, diluent or carrier.

Therefore the present invention further provides a pharmaceutical composition comprising a compound of formula (I) or a pharmaceutically acceptable salt thereof as hereinbefore defined, in association with a pharmaceutically acceptable adjuvant, diluent or carrier.

The invention still further provides a process for the preparation of a pharmaceutical composition of the invention which comprises mixing a compound of formula (I) or a pharmaceutically acceptable salt thereof as hereinbefore defined with a pharmaceutically acceptable adjuvant, diluent or carrier.

Conventional procedures for the selection and preparation of suitable pharmaceutical formulations are described in, for example, "Pharmaceutics—The Science of Dosage Form Design", M. E. Aulton, Churchill Livingstone, 1988.

Pharmaceutically acceptable adjuvants, diluents or carriers that may be used in the pharmaceutical compositions of the invention are those conventionally employed in the field of pharmaceutical formulation, and include, but are not limited to, sugars, sugar alcohols, starches, ion exchangers, alumina, aluminium stearate, lecithin, serum proteins, such as human serum albumin, buffer substances such as phosphates, glycerine, sorbic acid, potassium sorbate, partial glyceride mixtures of saturated vegetable fatty acids, water, salts or electrolytes, such as protamine sulphate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

The pharmaceutical compositions of the present invention may be administered orally, parenterally, by inhalation spray, rectally, nasally, buccally, vaginally or via an implanted reservoir. Oral administration is preferred. The pharmaceutical compositions of the invention may contain any conventional non-toxic pharmaceutically acceptable adjuvants, diluents or carriers. The term parenteral as used herein includes subcutaneous, intracutaneous, intravenous, intramuscular, intra-articular, intrasynovial, intrasternal, intrathecal, intralesional and intracranial injection or infusion techniques.

The pharmaceutical compositions may be in the form of a sterile injectable preparation, for example, as a sterile injectable aqueous or oleaginous suspension. The suspension may be formulated according to techniques known in the art using suitable dispersing or wetting agents (such as, for example, Tween 80) and suspending agents. The sterile injectable preparation may also be a sterile injectable solution or suspension in a non-toxic parenterally acceptable diluent or solvent, for example, as a solution in 1,3-butanediol. Among the acceptable diluents and solvents that may be employed are mannitol, water, Ringer's solution and isotonic sodium chloride solution. In addition, sterile, fixed oils are conventionally employed as a solvent or suspending medium. For this purpose, any bland fixed oil may be employed including synthetic mono- or diglycerides. Fatty acids, such as oleic acid and its glyceride derivatives are useful in the preparation of injectables, as are natural pharmaceutically acceptable oils, such as olive oil or castor oil, especially in their polyoxyethylated versions. These oil solutions or suspensions may also contain a long-chain alcohol diluent or dispersant such as that described in Pharmacopoeia Helvetica or a similar alcohol.

The pharmaceutical compositions of this invention may be orally administered in any orally acceptable dosage form including, but not limited to, capsules, tablets, powders, granules, and aqueous suspensions and solutions. These dosage forms are prepared according to techniques well-known in the art of pharmaceutical formulation. In the case of tablets for oral use, carriers which are commonly used include lactose and corn starch. Lubricating agents, such as magnesium stearate, are also typically added. For oral administration in a capsule form, useful diluents include lactose and dried corn starch. When aqueous suspensions are administered orally, the active ingredient is combined with emulsifying and suspending agents. If desired, certain sweetening and/or flavouring and/or colouring agents may be added.

The pharmaceutical compositions of the invention may also be administered in the form of suppositories for rectal administration. These compositions can be prepared by mixing the active ingredient with a suitable non-irritating excipient which is solid at room temperature but liquid at the rectal temperature and therefore will melt in the rectum to release the active ingredient. Such materials include, but are not limited to, cocoa butter, beeswax and polyethylene glycols.

The pharmaceutical compositions of this invention may be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other solubilising or dispersing agents known in the art.

Depending on the mode of administration, the pharmaceutical composition will preferably comprise from 0.05 to 99% w (percent by weight), more preferably from 0.05 to 80% w, still more preferably from 0.10 to 70% w, and even more preferably from 0.10 to 50% w, of active ingredient, all percentages by weight being based on total composition.

The compounds of the invention (that is, compounds of formula (I) and pharmaceutically acceptable salts thereof) may also be administered in conjunction with other compounds used for the treatment of the above conditions.

The invention therefore further relates to combination therapies wherein a compound of the invention or a pharmaceutical composition or formulation comprising a compound of the invention is administered with another therapeutic agent or agents, for the treatment of one or more of the conditions previously indicated. Such therapeutic agents may be selected from the following:

(i) antidepressants such as, for example, amitriptyline, amoxapine, bupropion, citalopram, clomipramine, desipramine, doxepin duloxetine, elzasonan, escitalopram, fluvoxamine, fluoxetine, gepirone, imipramine, ipsapirone, maprotiline, nortriptyline, nefazodone, paroxetine, phenelzine, protriptyline, reboxetine, robaizotan, sertraline, sibutramine, thionisoxetine, tranylcypromaine, trazodone, trimipramine, venlafaxine, and equivalents and pharmaceutically active isomer(s) and/or metabolite(s) thereof;

(ii) antipsychotics including, for example, quetiapine, amisulpride, aripiprazole, asenapine, benzisoxidil, bifeprunox, carbamazepine, clozapine, chlorpromazine, debenzapine, divalproex, duloxetine, eszopiclone, haloperidol, iloperidone, lamotrigine, loxapine, mesoridazine, olanzapine, paliperidone, perlapine, perphenazine, phenothiazine, phenylbutlypiperidine, pimozide, prochlorperazine, risperidone, sertindole, sulpiride, suproclone, suriclone, thioridazine, trifluoperazine, trimetozine, valproate, valproic acid, zopiclone, zotepine, ziprasidone, and equivalents and pharmaceutically active isomer(s) and/or metabolite(s) thereof;

(iii) anxiolytics including, for example, alnespirone, azapirones, benzodiazepines, barbiturates, and equivalents and pharmaceutically active isomer(s) and/or metabolite(s) thereof. Example anxiolytics include adinazolam, alprazolam, balezepam, bentazepam, bromazepam, brotizolam, buspirone, clonazepam, clorazepate, chlordiazepoxide, cyprazepam, diazepam, diphenhydramine, estazolam, fenobam, flunitrazepam, flurazepam, fosazepam, lorazepam, lormetazepam, meprobamate, midazolam, nitrazepam, oxazepam, prazepam, quazepam, reclazepam, tracazolate, trepipam, temazepam, triazolam, uldazepam, and zolazepam; and equivalents and pharmaceutically active isomer(s) and/or metabolite(s) thereof;

(iv) anticonvulsants including, for example, carbamazepine, oxcarbazepine, valproate, lamotrigine, and gabapentin, and equivalents and pharmaceutically active isomer(s) and/or metabolite(s) thereof;

(v) Alzheimer's therapies including, for example, donepezil, memantine, tacrine, and equivalents and pharmaceutically active isomer(s) and/or metabolite(s) thereof;

(vi) neuropathic pain therapies including, for example, gabapentin, lidoderm, and pregablin, and equivalents and pharmaceutically active isomer(s) and/or metabolite(s) thereof;

(vii) nociceptive pain therapies such as, for example, celecoxib, etoricoxib, lumiracoxib, rofecoxib, valdecoxib, diclofenac, loxoprofen, naproxen, and paracetamol, and equivalents and pharmaceutically active isomer(s) and/or metabolite(s) thereof;

(viii) mood stabilizers including, for example, carbamazepine, oxcarbazepine, divalproex, gabapentin, lamotrigine, lithium, olanzapine, quetiapine, valproate, valproic acid, and verapamil, and equivalents and pharmaceutically active isomer(s) and/or metabolite(s) thereof; and (ix) alpha 7 nicotinic agonists such as, for example, compounds disclosed in WO 96/006098, WO 97/030998, WO 99/003859, WO 00/042044, WO 01/029034, WO 01/60821, WO 01/36417, WO 02/096912, WO 03/087102, WO 03/087103, WO 03/087104, WO 2004/016617, WO 2004/016616, and WO 2004/019947;

Such combination products employ the compounds of this invention within the dosage range described herein and the other pharmaceutically active agent within approved dosage ranges and/or the dosage such as described in the publication reference.

In a further aspect the present invention provides a combination (for example for the treatment of schizophrenia, cognitive disorders or pain) of a compound of formula (I) or a pharmaceutically acceptable salt thereof as hereinbefore defined and one or more agents selected from carbamazepine, olanzapine, quetiapine, verapamil, lamotrigine, oxcarbazepine, risperidone, aripiprazole, ziprasidone and lithium.

The invention also provides a pharmaceutical product comprising, in combination, a preparation of a first active ingredient which is a compound of formula (I) or a pharmaceutically acceptable salt thereof as hereinbefore defined, and a preparation of a second active ingredient which is carbamazepine, olanzapine, quetiapine, verapamil, lamotrigine, oxcarbazepine, risperidone, aripiprazole, ziprasidone or lithium, for simultaneous, sequential or separate use in therapy.

In another aspect, the invention provides a kit comprising a preparation of a first active ingredient which is a compound of formula (I) or a pharmaceutically acceptable salt thereof as hereinbefore defined, and a preparation of a second active ingredient which is carbamazepine, olanzapine, quetiapine, verapamil, lamotrigine, oxcarbazepine, risperidone, aripiprazole, ziprasidone or lithium, and instructions for the simultaneous, sequential or separate administration of the preparations to a patient in need thereof.

The invention will now be illustrated, but not limited, by reference to the specific embodiments described in the following examples.

EXAMPLES 1 TO 86

The compounds of Examples 1 to 86 shown in Table 1 below have been prepared. Their NMR and LCMS properties and the methods used to prepare them are set out in Table 2.

TABLE 1

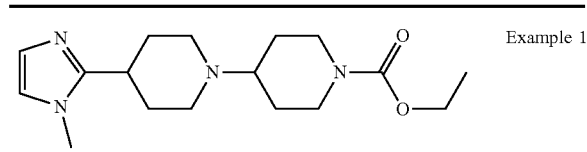

Example 1

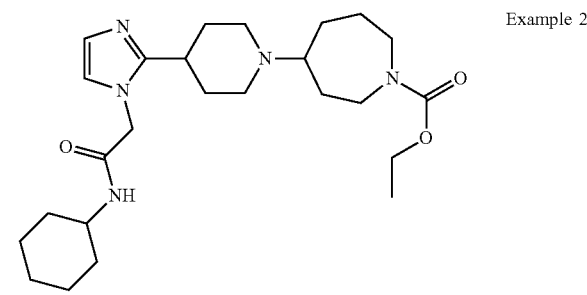

Example 2

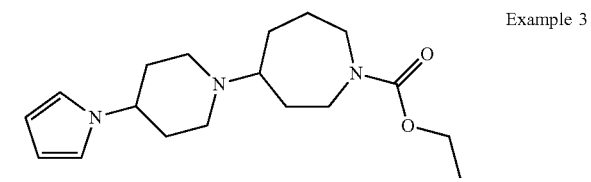

Example 3

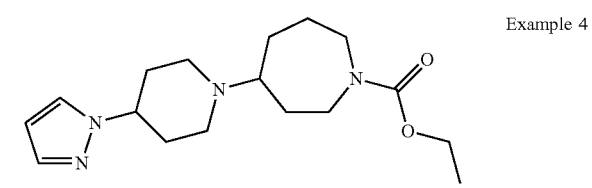

Example 4

TABLE 1-continued
Example 5
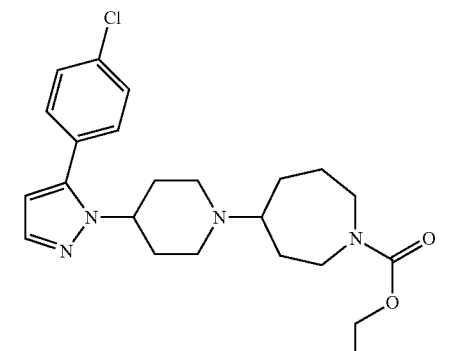
Example 6
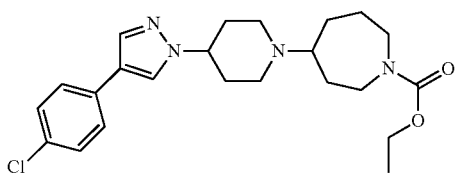 [SMILES: CCOC(=O)N1CCCC(N2CCC(n3cc(-c4ccc(Cl)cc4)cn3)CC2)CC1]
Example 7
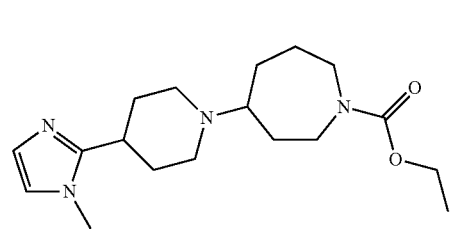
Example 8
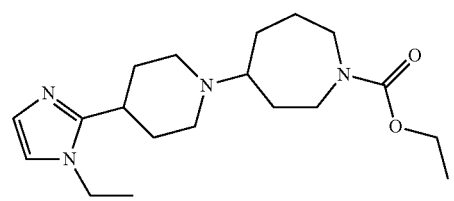 [SMILES: CCOC(=O)N1CCCC(N2CCC(c3nccn3CC)CC2)CC1]
Example 9
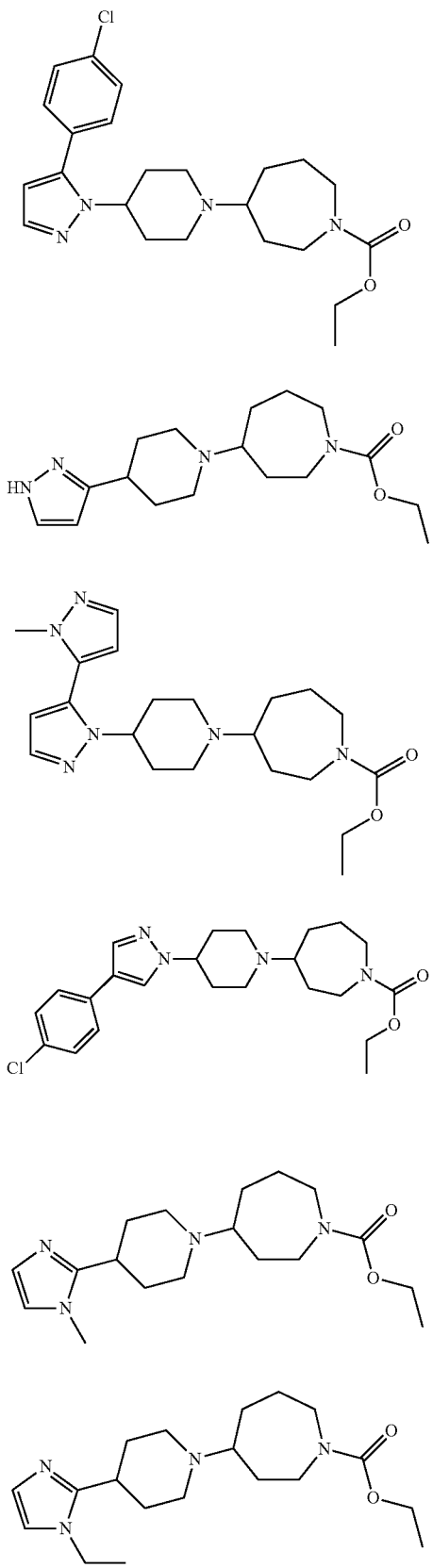
Example 10
TABLE 1-continued
Example 11
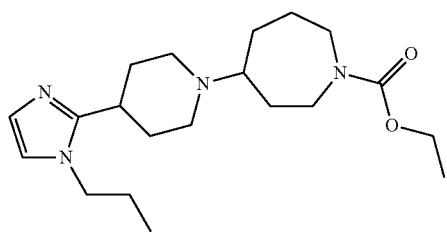 [SMILES: CCCn1ccnc1C1CCN(C2CCCN(C(=O)OCC)CC2)CC1]
Example 12
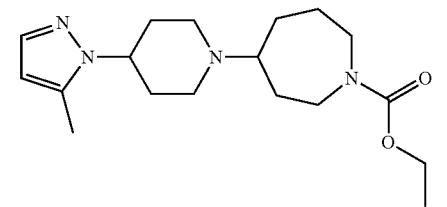 [SMILES: CCOC(=O)N1CCCC(N2CCC(n3nccc3C)CC2)CC1]
Example 13
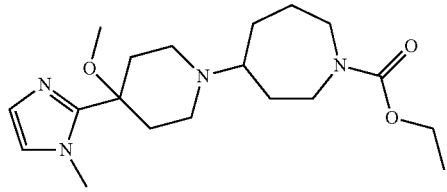
Example 14
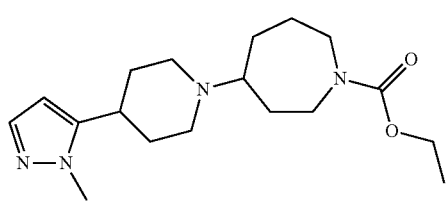
Example 15
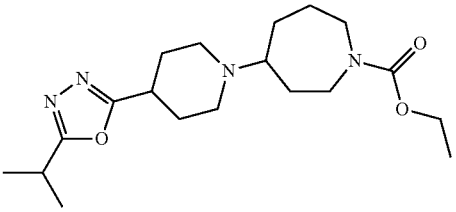 [SMILES: CCOC(=O)N1CCCC(N2CCC(c3nnc(C(C)C)o3)CC2)CC1]
Example 16
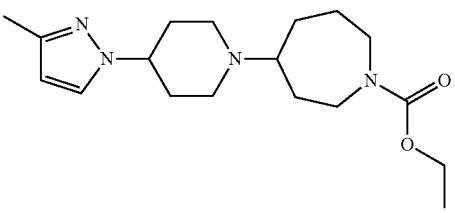 [SMILES: CCOC(=O)N1CCCC(N2CCC(n3ccc(C)n3)CC2)CC1]
Example 17
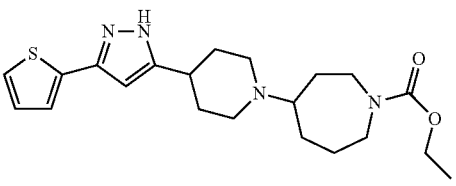 [SMILES: CCOC(=O)N1CCCC(N2CCC(c3cc(-c4cccs4)n[nH]3)CC2)CC1]

TABLE 1-continued
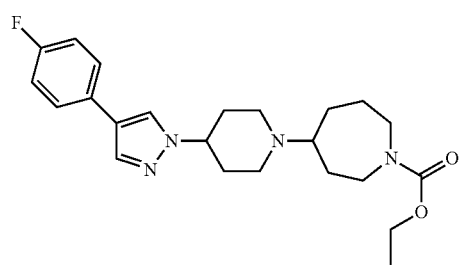 [SMILES: CCOC(=O)N1CCCC(N2CCC(n3cc(-c4ccc(F)cc4)cn3)CC2)CC1] Example 18
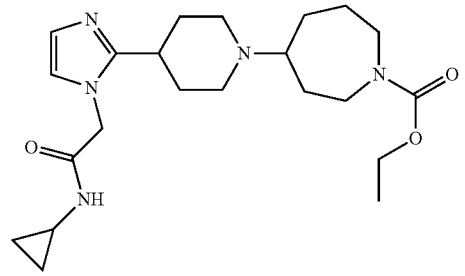 [SMILES: CCOC(=O)N1CCCC(N2CCC(c3nccn3CC(=O)NC3CC3)CC2)CC1] Example 19
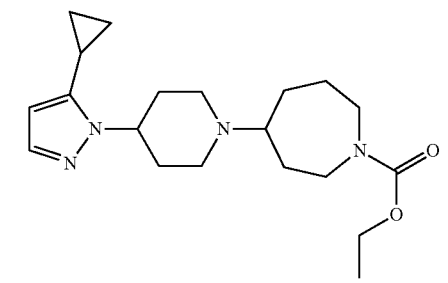 [SMILES: CCOC(=O)N1CCCC(N2CCC(n3nccc3C3CC3)CC2)CC1] Example 20
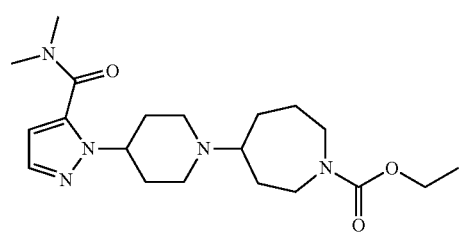 [SMILES: CCOC(=O)N1CCCC(N2CCC(n3nccc3C(=O)N(C)C)CC2)CC1] Example 21
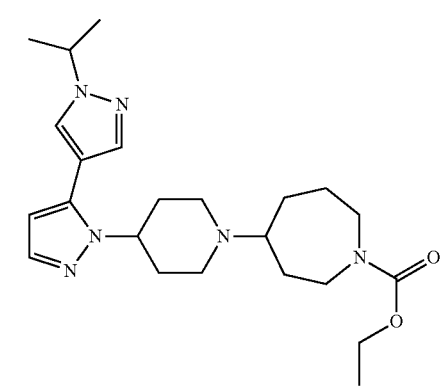 [SMILES: CCOC(=O)N1CCCC(N2CCC(n3nccc3-c3cnn(C(C)C)c3)CC2)CC1] Example 22
TABLE 1-continued
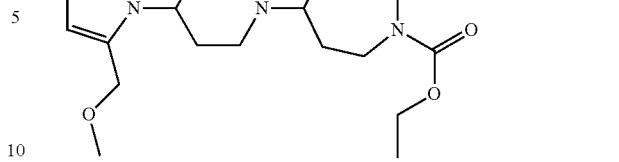 Example 23
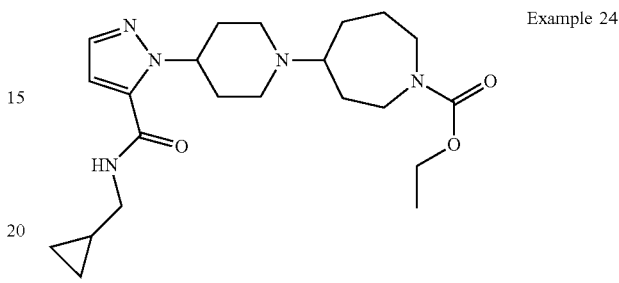 Example 24
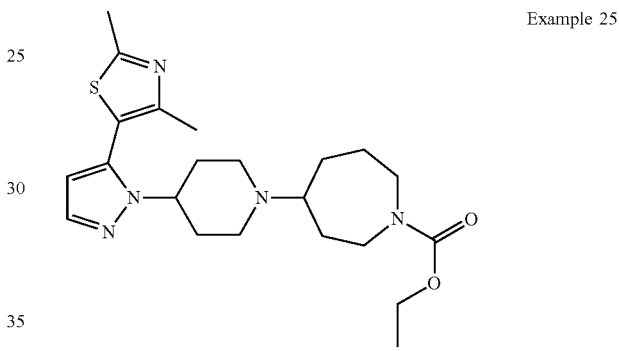 Example 25
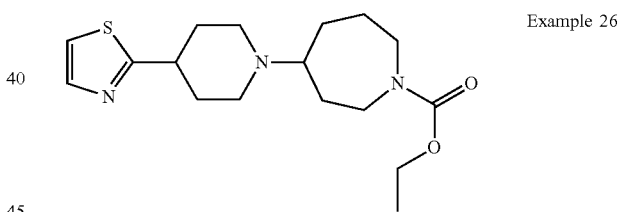 Example 26
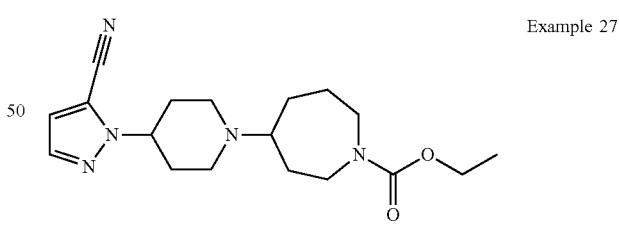 Example 27
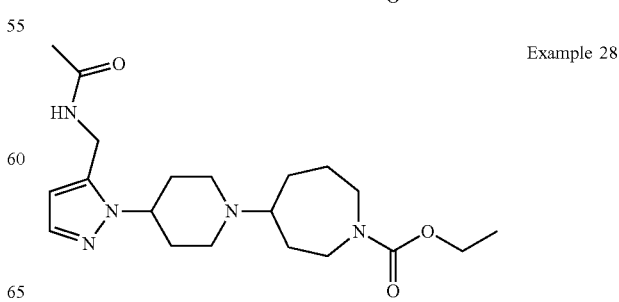 Example 28

TABLE 1-continued
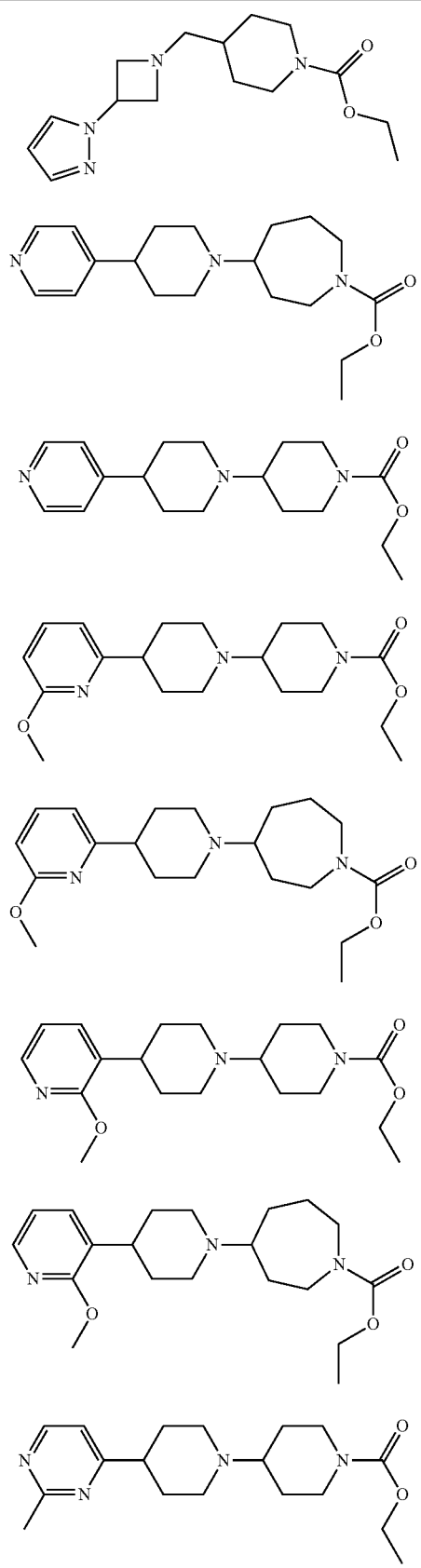
Example 29
Example 30
Example 31
Example 32
Example 33
Example 34
Example 35
Example 36
TABLE 1-continued
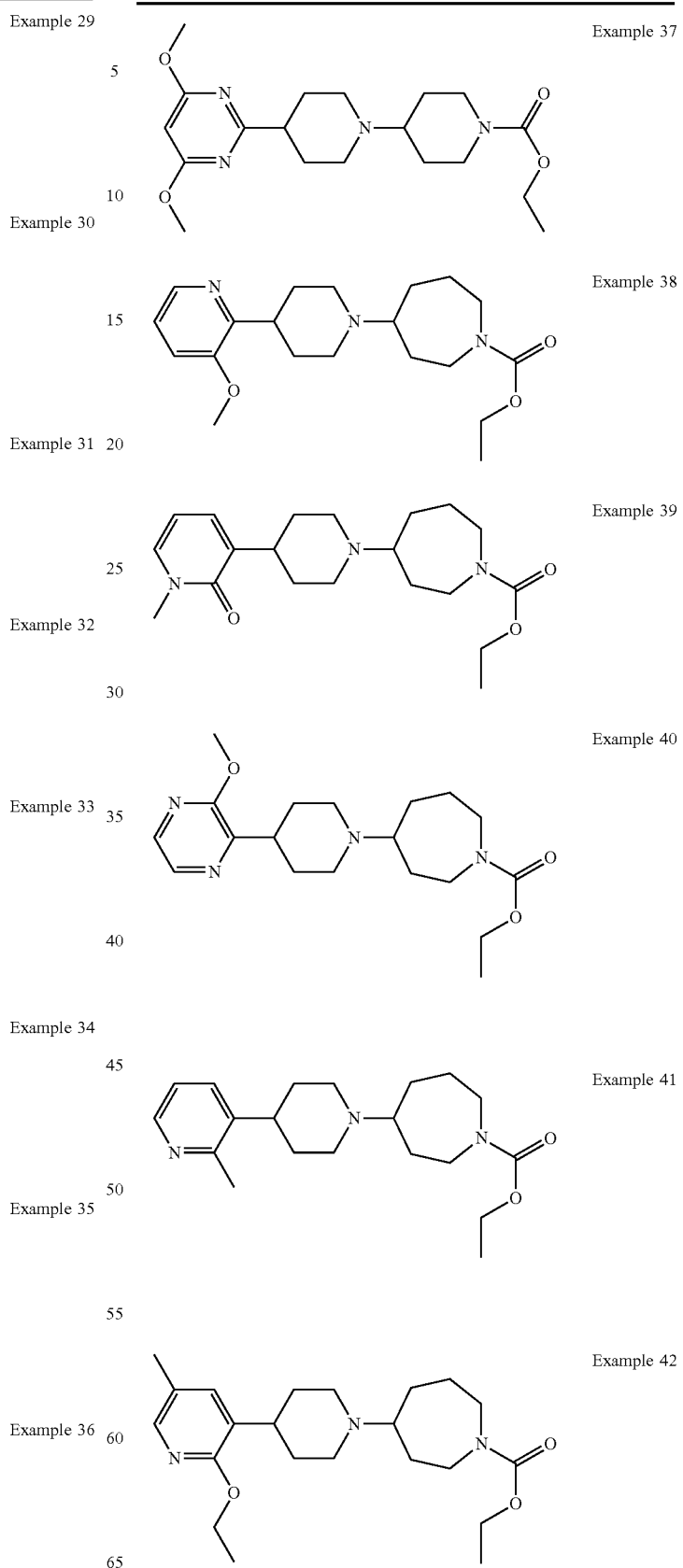
Example 37
Example 38
Example 39
Example 40
Example 41
Example 42

TABLE 1-continued

| | |
|---|---|
| Example 43 | |
| Example 44 | Example 49 |
| Example 45 | Example 50 |
| Example 46 | Example 51 |
| Example 47 | Example 52 |
| Example 48 | Example 53 |
| | Example 54 |
| | Example 55 |

TABLE 1-continued
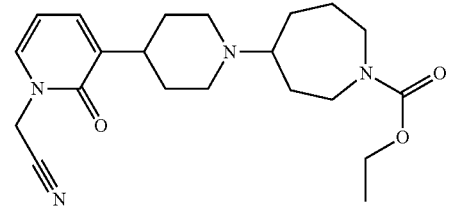 [SMILES: CCOC(=O)N1CCCC(N2CCC(c3cccn(CC#N)c3=O)CC2)CC1]
Example 56
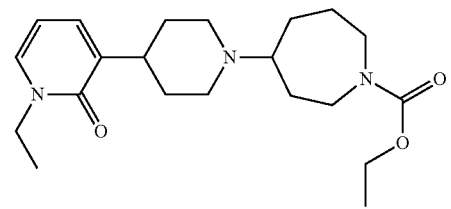 [SMILES: CCOC(=O)N1CCCC(N2CCC(c3cccn(CC)c3=O)CC2)CC1]
Example 57
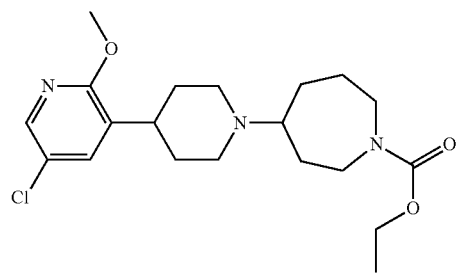 [SMILES: CCOC(=O)N1CCCC(N2CCC(c3cc(Cl)cnc3OC)CC2)CC1]
Example 58
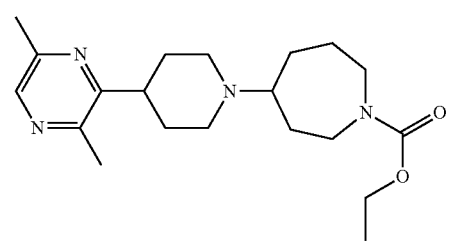 [SMILES: CCOC(=O)N1CCCC(N2CCC(c3nc(C)cnc3C)CC2)CC1]
Example 59
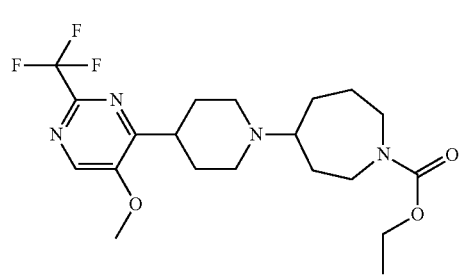 [SMILES: CCOC(=O)N1CCCC(N2CCC(c3nc(C(F)(F)F)ncc3OC)CC2)CC1]
Example 60
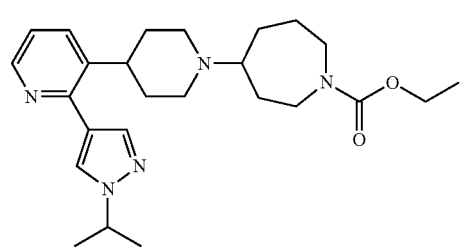 [SMILES: CCOC(=O)N1CCCC(N2CCC(c3cccnc3-c3cnn(C(C)C)c3)CC2)CC1]
Example 61
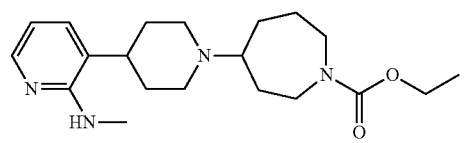 [SMILES: CCOC(=O)N1CCCC(N2CCC(c3cccnc3NC)CC2)CC1]
Example 62
TABLE 1-continued
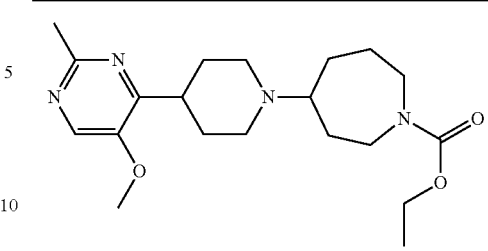
Example 63
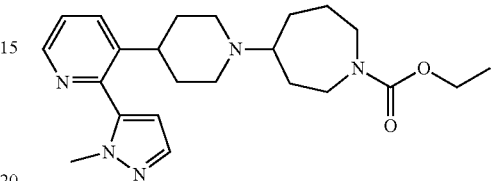
Example 64
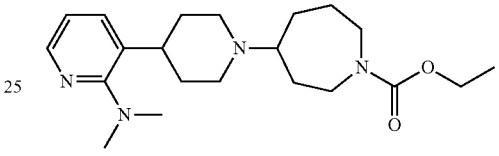
Example 65
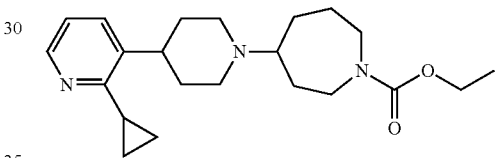
Example 66
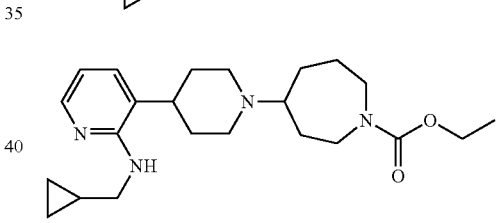
Example 67
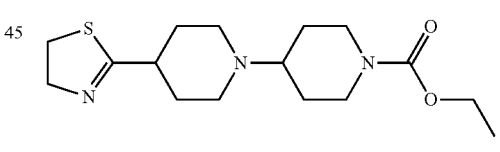
Example 68
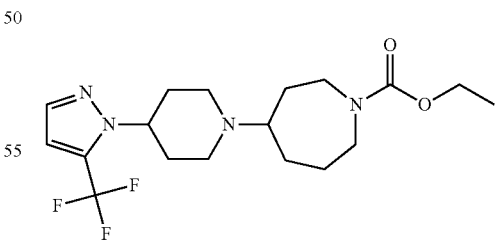
Example 69
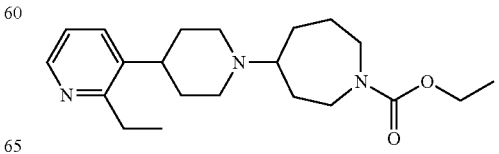
Example 70

TABLE 1-continued
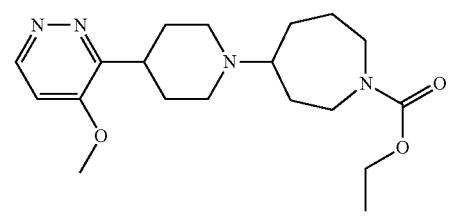 [SMILES: CCOC(=O)N1CCCC(N2CCC(c3nnccc3OC)CC2)CC1] Example 71
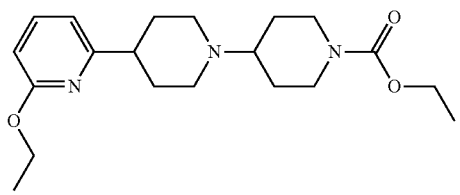 [SMILES: CCOC(=O)N1CCC(N2CCC(c3cccc(OCC)n3)CC2)CC1] Example 72
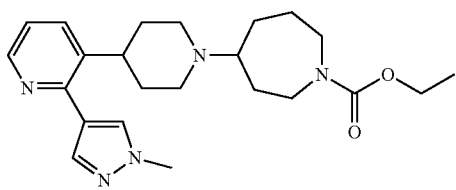 [SMILES: CCOC(=O)N1CCCC(N2CCC(c3cccnc3-c3cnn(C)c3)CC2)CC1] Example 73
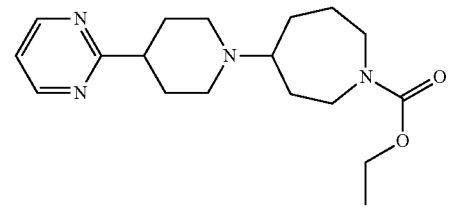 [SMILES: CCOC(=O)N1CCCC(N2CCC(c3ncccn3)CC2)CC1] Example 74
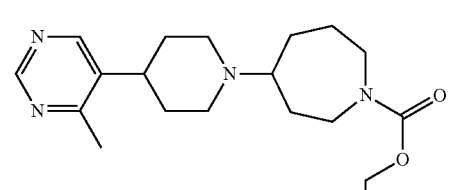 Example 75
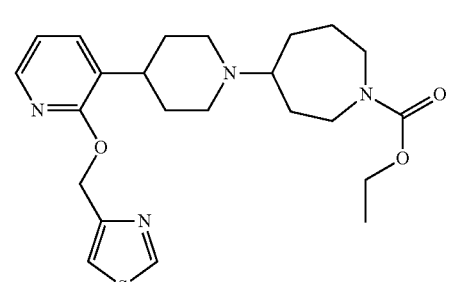 Example 76
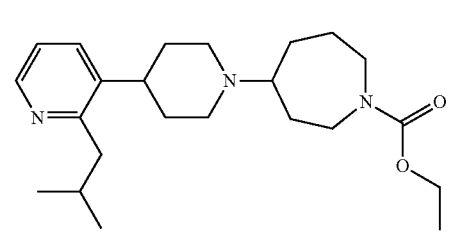 Example 77
TABLE 1-continued
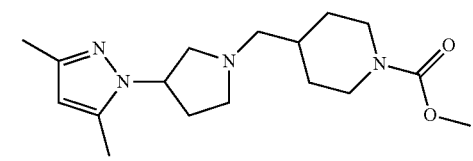 Example 78
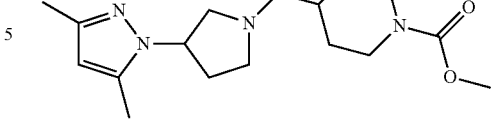 Example 79
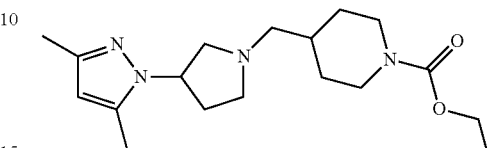 Example 80
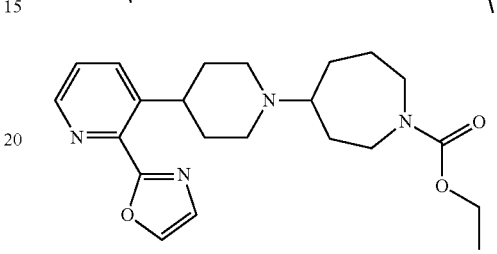 Example 81
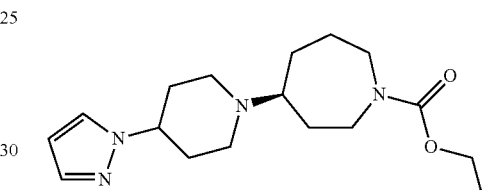 Example 82
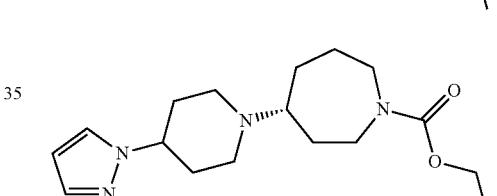 Example 83
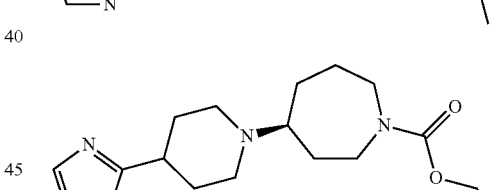 Example 84
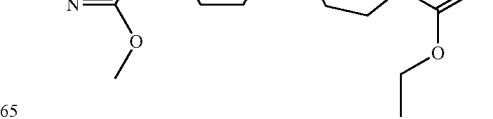 Example 85

General Procedures

Where no preparative routes are included, the relevant intermediate is commercially available. Commercial reagents were utilized without further purification.

Room temperature (rt) refers to approximately 20-27° C.

Microwave-mediated reactions were performed in Biotage Initiator or CEM Discover microwave reactors.

$^1$H NMR spectra were recorded at 400 MHz on either a Bruker or Jeol instrument. Chemical shift values are expressed in parts per million (ppm), i.e. (δ)-values. The following abbreviations are used for the multiplicity of the NMR signals: s=singlet, br=broad, d=doublet, t=triplet, q=quartet, quint=quintet, td=triplet of doublets, tt=triplet of triplets, qd=quartet of doublets, ddd=doublet of doublet of doublets, ddt=doublet of doublet of triplets, m=multiplet. Coupling constants are listed as J values, measured in Hz.

Mass spectroscopy was carried out on Shimadzu LC-2010 EV, Waters ZQ-2000, UPLC-Mass SQD-3100 or Applied Biosystem API-2000 spectrometers or Waters SQD single quadrupole mass spectrometer using atmospheric pressure isonisation.

Compounds were purified using normal phase chromatography on silica or alumina, or by reverse phase chromatographic methods, using Biotage or Isolute KPNH Cartridge, SCX cartridge and SCX-2 solid phase extraction cartridges.

Preparative HPLC was typically carried out under the following conditions, (Waters HPLC): Column: XSelect CSH Prep C-18, 19×50 mm, 5 μm; Mobile phase: Gradients of water and MeCN (each containing 0.1% Formic Acid); gradient 5% MeCN in 0.1 HCOOH in water (30 sec), 5% to 40% (over 7 min) then 95% MeCN in 0.1 HCOOH in water (1 min) then 5% MeCN in 0.1 HCOOH in water (1.5 min) at 28 mL/min; or performed using either an Agilent Technologies 1100 Series system or a Waters FractionLynx system typically using Waters 19 mm id×200 mm long C18 columns such as XBridge or SunFire 5 μm materials at room temperature. Mobile phases typically consisted of acetonitrile or methanol mixed with water containing either 0.1% formic acid or 0.1% ammonia.

ABBREVIATIONS acac=acetylacetonate
BINAP=2,2'-bis(diphenylphosphino)-1,1'-binaphthyl
BOC=N-tert-butoxycarbonyl
Burgess=methyl N-(triethylammoniumsulphonyl)carbamate reagent
t-BuX-Phos=2-Di-tert-butylphosphino-3,4,5,6-tetramethyl-2',4',6'-triisopropyl-1,1'-biphenyl
d=day(s)
dba=dibenzylideneacetone
dppf=1,1'-Bis(diphenylphosphino)ferrocene
dppp=1,3-Bis(diphenylphosphino)propane
DBU=1,8-Diazabicyclo[5.4.0]undec-7-ene
DCE=dichloroethane
DCM=dichloromethane
DIPEA=diisopropylethylamine
DMF=dimethylformamide
DMSO=dimethylsulphoxide
EDAC=N-(3-dimethylaminopropyl)-N'-ethylcarbodiimide hydrochloride
ES=electro spray ionisation
Et=ethyl
EtOAc=ethyl acetate
h=hour(s)
Hermann's Catalyst=trans-Di-(μ-acetate)bis[o-(di-o-tolylphosphine)benzyl]dipalladium(II)
HATU=2-(7-Aza-1H-benzotriazole-1-yl)-1,1,3,3-tetramethyluronium hexafluorophosphate
HOBt=1-hydroxybenzotriazole hydrate
HPLC=high performance liquid chromatography
LC=liquid chromatography
Me=methyl
MeCN=acetonitrile
min=minute(s)
mm=millimetre
MsCl=Methanesulphonyl chloride
MS=mass spectrometry
NMP=N-methyl-2-pyrrolidone
NMR=nuclear magnetic resonance
Ph=Phenyl
rt=room temperature
sat.=saturated
sec=second
sol.=solution
STAB=sodium triacetoxyborohydride
TBAB=tetra-n-butyl ammonium bromide
TBAI=tetra-n-butyl ammonium iodide
TEA=triethylamine
TFA=trifluoroacetic acid
THF=tetrahydrofuran
TLC=thin layer chromatography Prefixes n-, s-, i-, t- and tert-have their usual meanings: normal, secondary, iso, and tertiary.

SYNTHESIS OF INTERMEDIATES

Intermediate 1

Preparation of 1-(1-(ethoxycarbonyl)azepan-4-yl)piperidine-4-carboxylic acid

39

-continued

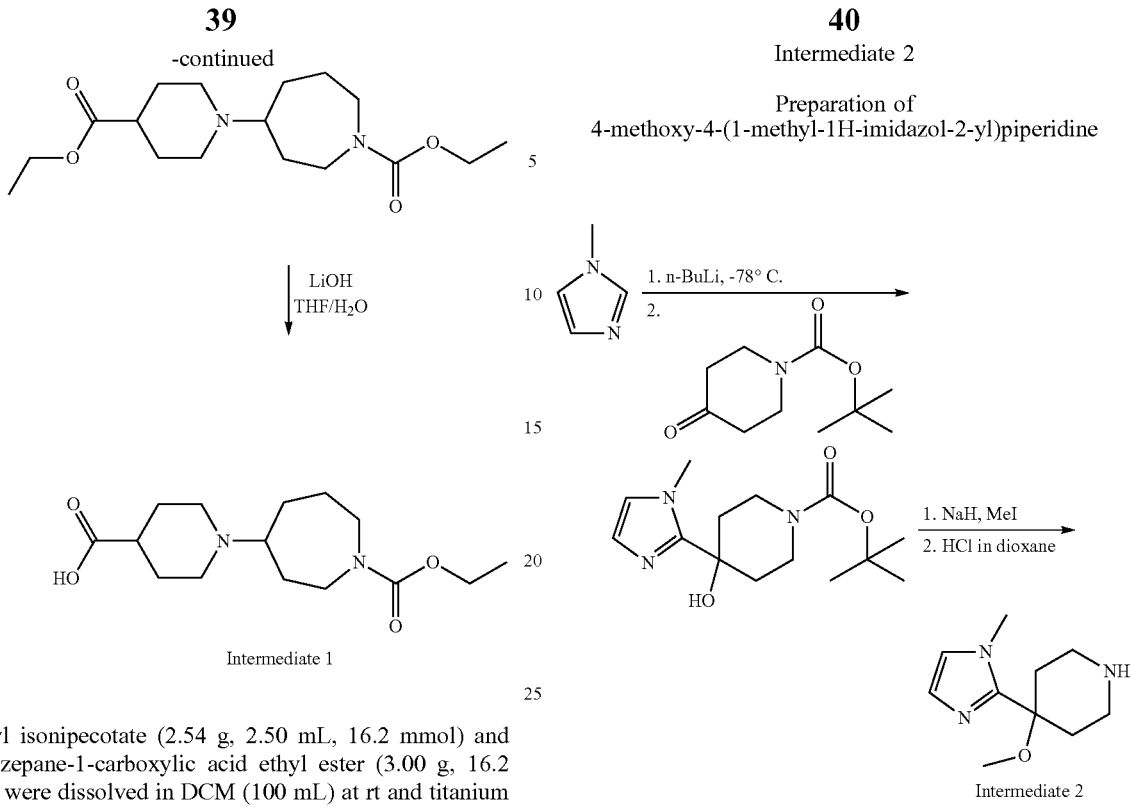

Intermediate 1

Ethyl isonipecotate (2.54 g, 2.50 mL, 16.2 mmol) and 4-oxoazepane-1-carboxylic acid ethyl ester (3.00 g, 16.2 mmol) were dissolved in DCM (100 mL) at rt and titanium isopropoxide (5.07 g, 5.40 mL, 17.8 mmol) was added. The reaction mixture was stirred at rt for 1 h. STAB (13.7 g, 32.4 mmol) and acetic acid (0.5 mL) were added and the reaction mixture was stirred at rt overnight under nitrogen. The reaction mixture was quenched with the addition of water (5 mL) and stirred for 5 minutes. The reaction mixture was diluted with DCM and filtered through a pad of diatomaceous earth (commercially sold under the trade mark "Celite"). The filtrate was washed with sat. $NaHCO_3$ sol., sat. NaCl sol. and dried over $MgSO_4$. The solvents were removed in vacuo, and the residue was purified by column chromatography (normal phase, [Biotage SNAP cartridge KP-sil 50 g, 40-63 μm, 60 Å, 50 mL per min, gradient 2% to 4% MeOH in DCM]) to give ethyl 4-[4-(ethoxycarbonyl) piperidin-1-yl]azepane-1-carboxylate (2.56 g, 48%) as a pale yellow oil.

MS: m/z 327 (M+H)$^+$ (ES$^+$)

$^1$H NMR: (400 MHz, DMSO-$d_6$) δ 1.17 (t, J=7.07 Hz, 6 H) 1.27-1.61 (m, 3 H) 1.76 (m, J=11.10 Hz, 5 H) 2.10-2.45 (m, 4 H) 2.58-2.76 (m, 2 H) 3.08-3.25 (m, 2 H) 3.30-3.35 (m, 2 H) 3.38-3.51 (m, 2 H) 3.91-4.10 (m, 4 H)

Ethyl 4-[4-(ethoxycarbonyl)piperidin-1-yl]azepane-1-carboxylate (1.10 g, 3.4 mmol) was dissolved in THF (60 mL) at rt and 1M LiOH sol. (10 mL) was added. The reaction mixture was stirred at rt for 5d. The pH was carefully adjusted to pH 6 by addition of concentrated hydrochloric acid, the solvents were removed in vacuo, to give 1-(1-(ethoxycarbonyl)azepan-4-yl)piperidine-4-carboxylic acid (1.5 g) as a viscous pale yellow oil, Intermediate 1, which was used crude in subsequent reactions.

MS: m/z 299 (M+H)$^+$ (ES$^+$)

$^1$H NMR: (400 MHz, CD$_3$OD) δ 1.22-1.32 (m, 3H), 1.60-2.38 (m, 11H), 2.08-2.22 (m, 1H), 3.13-3.26 (m, 2H), 3.33-3.51 (m, 2H), 3.52-3.76 (m, 2H), 4.08-4.18 (m, 2H), OH proton not observed

40

Intermediate 2

Preparation of 4-methoxy-4-(1-methyl-1H-imidazol-2-yl)piperidine

Intermediate 2

1-Methyl imidazole (6.0 g, 73.0 mmol) was dissolved in THF (100 mL) at rt and the reaction mixture was cooled to −78° C. under nitrogen, n-BuLi in hexane (45.4 mL, 73.0 mmol) was slowly added. The reaction mixture was gradually warmed to 40° C. and stirred for 4 h, then cooled to −78° C. tert-Butyl 4-oxopiperidine-1-carboxylate (14.56 g, 73.0 mmol) in THF (100 mL) was added. The reaction mixture was gradually warmed to 40° C. and stirred for 10 h, then quenched with water (50 mL). The reaction mixture was partitioned between EtOAc (200 mL) and water (150 mL), the aqueous layer was extracted with EtOAc (2×200 mL) and the organic layers were combined and dried (Na$_2$SO$_4$). The solvents were removed in vacuo, and the residue was washed with methanol to give tert-butyl 4-hydroxy-4-(1-methyl-1H-imidazol-2-yl)piperidine-1-carboxylate (14.0 g, 68.1%) as a solid which was used crude in the subsequent reaction.

MS: m/z 282 (M+H)$^+$ (ES$^+$)

A portion of tert-butyl 4-hydroxy-4-(1-methyl-1H-imidazol-2-yl)piperidine-1-carboxylate (3.0 g, 10.6 mmol) was dissolved in DMF (50 mL) at rt and the reaction mixture was cooled to 0° C. under nitrogen, NaH (0.64 g, 16.0 mmol) was added. The reaction mixture was stirred at 0° C. for 1 h and then iodomethane (1.8 g, 128 mmol) was slowly added. The reaction mixture was gradually warmed to 30° C. and stirred for 10 h, then quenched with water (50 mL). The reaction mixture was extracted with EtOAc (3×200 mL), and the organic layers were combined and dried (Na$_2$SO$_4$). The solvents were removed in vacuo, and the residue was purified by column chromatography (normal phase, silica, 60-120 mesh, gradient 0% to 50% EtOAc in Hexane) to give tert-butyl 4-methoxy-4-(1-methyl-1H-imidazol-2-yl)piperidine-1-carboxylate (1.3 g, 41.3%) as a solid.

MS: m/z 296 (M+H)$^+$ (ES$^+$).

$^1$H NMR (400 MHz, DMSO-$d_6$) δ: 1.40 (s, 9H), 1.87-1.94 (m, 2H), 1.97-2.06 (m, 2H), 2.91 (s, 3H), 3.12-3.19 (m, 2H), 3.60-3.66 (m, 2H), 3.73 (s, 3H), 6.79 (s, 1H), 7.13 (s, 1H).

tert-Butyl 4-methoxy-4-(1-methyl-1H-imidazol-2-yl)piperidine-1-carboxylate (1.3 g, 3.3 mmol) was dissolved in 1,4 dioxane (30 mL) at rt and the reaction mixture was cooled to 0° C. under nitrogen, HCl in dioxane (15 mL, 3M sol.) was slowly added. The reaction mixture was stirred at rt for 6 h, the solvents were removed in vacuo, and the residue purified by trituration from pentane (10 mL) and diethyl ether (10 mL) to afford 4-methoxy-4-(1-methyl-1H-imidazol-2-yl)piperidine, Intermediate 2, (0.80 g, 94.1%) as a solid.

MS: 196 [M+H]+.

Intermediate 3

4-Oxoazepane-1-carboxylic acid ethyl ester commercially available, CAS: 56515-89-0.

Intermediate 4

Preparation of ethyl 4-(4-(5-bromo-1H-pyrazol-1-yl)piperidin-1-yl)azepane-1-carboxylate

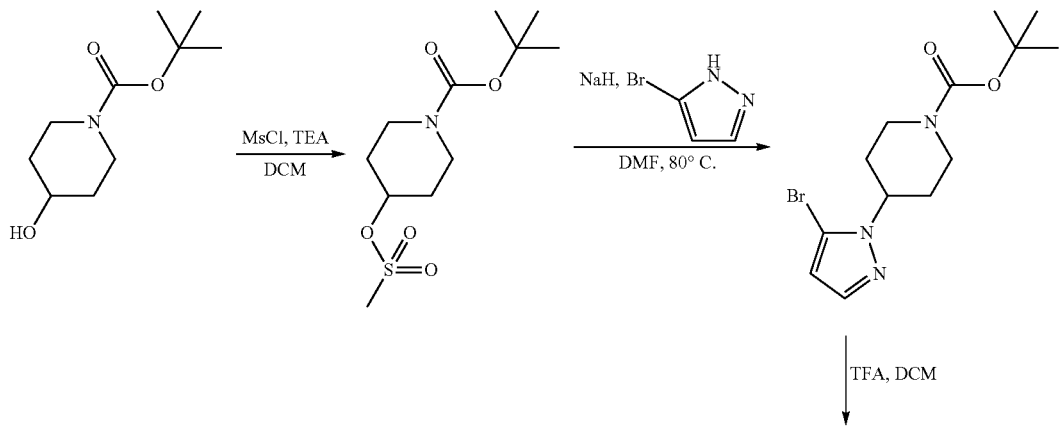

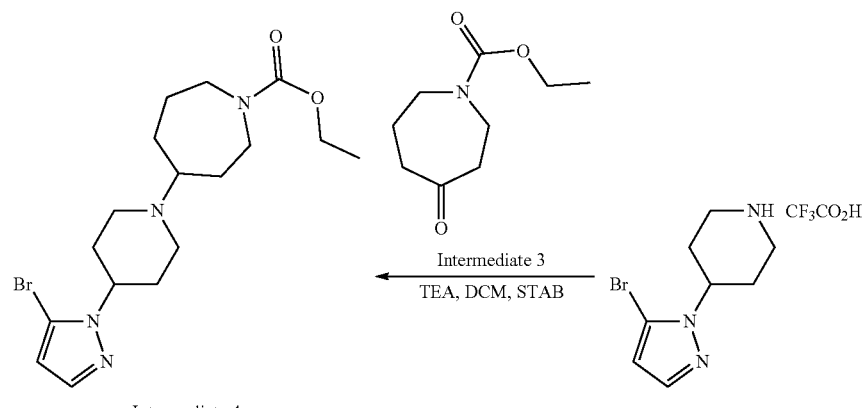

As described hereinafter in general synthetic procedure, route q.

Intermediate 5

Preparation of 3-bromo-1-methylpyridin-2(1H)-one

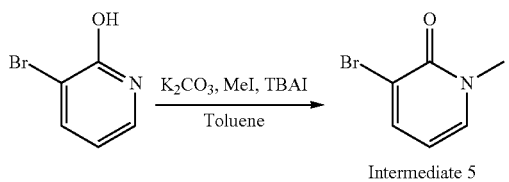

Intermediate 5

Methyl iodide (1.5 mL, 24.14 mmol) was added to a suspension of potassium carbonate (1668 mg, 12.07 mmol), TBAI (89 mg, 0.24 mmol) and 3-bromopyridin-2-ol (420 mg, 2.414 mmol) in toluene (15 mL). The reaction mixture was heated to 40° C. for 17 hours. The mixture was partitioned between DCM and water and the combined extracts dried (hydrophobic frit) and concentrated in vacuo. The crude product was purified by column chromatography on silica, eluted with 0-70% petrol/ethyl acetate to afford 3-bromo-1-methylpyridin-2(1H)-one, Intermediate 5 (390 mg, 86%).

$^1$H NMR (400 MHz, DMSO-d$_6$) δ: 3.50 (s, 3 H) 6.17 (t, J=7.07 Hz, 1 H) 7.78 (dd, J=6.82, 1.77 Hz, 1 H) 7.90 (dd, J=7.33, 1.77 Hz, 1 H)

Intermediate 6

Preparation of 2-chloro-N-cyclohexylacetamide

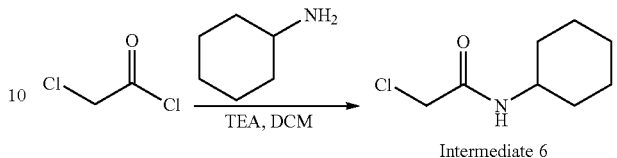

Intermediate 6

To an ice cold solution of chloroacetyl chloride (0.7 mL, 8.85 mmol) in DCM (10 mL) was added cyclohexanamine (878 mg, 8.85 mmol) and TEA (1.36 mL, 9.74 mmol) in DCM (10 mL) in a drop-wise fashion. The reaction mixture was stirred at room temperature for 1 h. The mixture was diluted with DCM, washed with water, dried (hydrophobic frit) and concentrated in vacuo yielding 2-chloro-N-cyclohexylacetamide, Intermediate 6 (1.73 g, quantitative yield)

$^1$H NMR (CDCl$_3$) δ: 6.35 (br. s., 1H), 3.96 (s, 2H), 3.64-3.83 (m, 1H), 1.81-1.94 (m, 2H), 1.49-1.70 (m, 3H), 1.24-1.40 (m, 2H), 1.04-1.22 (m, 3H)

Intermediate 7

Preparation of 4-(5-(methoxymethyl)-1H-pyrazol-1-yl)piperidine

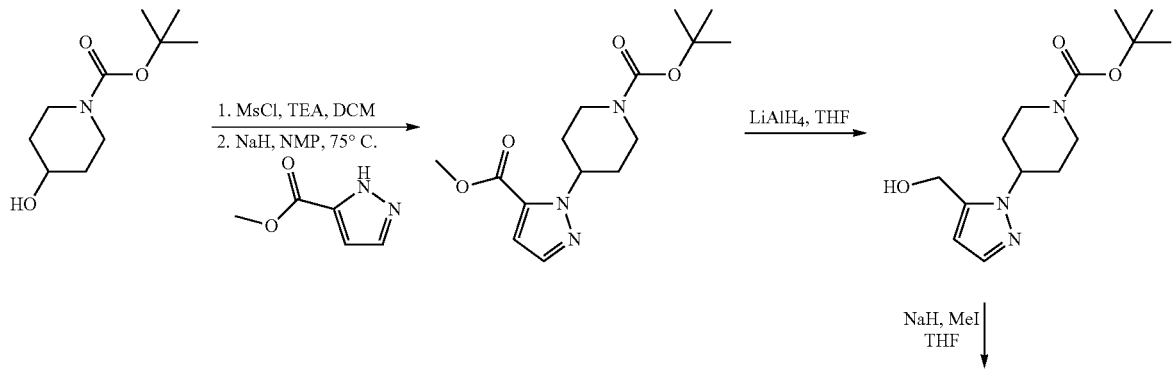

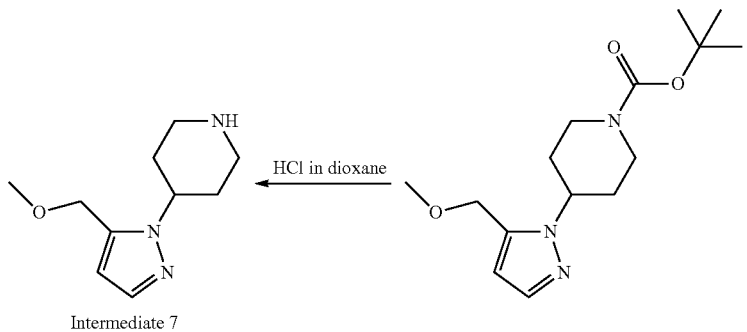

Intermediate 7

Methanesulphonyl chloride (1.123 g, 9.8 mmol) was added dropwise to a solution of tert-butyl 4-hydroxypiperidine-1-carboxylate (1.409 g, 7 mmol) and TEA (0.992 g, 9.8 mmol) in DCM (35 mL) under nitrogen. The reaction was stirred at room temperature for 3 hours. The reaction mixture was then washed with water, dried (hydrophobic frit) and concentrated in vacuo to yield tert-butyl 4-((methylsulphonyl)oxy)piperidine-1-carboxylate (1955 mg, 7 mmol). The crude product was used without further purification in the next step.

Sodium hydride (252 mg, 10.5 mmol) was added to a solution of methyl 1H-pyrazole-3-carboxylate (883 mg, 7.00 mmol) in NMP (17.5 mL) in a microwave vial. The reaction was stirred at room temperature for 0.5 hours. tert-Butyl 4-((methylsulphonyl)oxy)-piperidine-1-carboxylate (1955 mg, 7 mmol) was added and the vial sealed. The reaction was heated to 75° C. overnight. The reaction mixture was partitioned between DCM and water, dried (hydrophobic frit) and the organic phase concentrated in vacuo. The crude product was purified by reverse phase chromatography on C18 silica eluted with 5-95% water (with 0.05% ammonia)/acetonitrile to afford tert-butyl 4-(5-(methoxycarbonyl)-1H-pyrazol-1-yl)piperidine-1-carboxylate (337 mg, 1.089 mmol, 15.6%)

$^1$H NMR (400 MHz, DMSO-d$_6$) δ: 1.41 (s, 9 H) 1.71-1.96 (m, 4 H) 3.19-3.37 (m, 2 H) 3.84 (s, 3 H) 4.07 (m, J=12.60 Hz, 2 H) 5.11-5.30 (m, 1 H) 6.89 (d, J=2.02 Hz, 1 H) 7.61 (d, J=1.77 Hz, 1 H)

Lithium aluminium hydride (28.3 mg, 0.75 mmol) was added to a solution of tert-butyl 4-(5-(methoxycarbonyl)-1H-pyrazol-1-yl)piperidine-1-carboxylate (330 mg, 1.07 mmol) in THF (5 mL) under nitrogen, with ice bath cooling. The reaction was stirred, with warming to room temperature over 1 hour. The reaction was quenched with water and 2M NaOH, stirred for 15 minutes and then extracted with DCM, dried (hydrophobic frit) and the solvent removed in vacuo to afford tert-butyl 4-(5-(hydroxymethyl)-1H-pyrazol-1-yl)piperidine-1-carboxylate (300 mg, 1.07 mmol, quantitative yield) as product. This was used without further purification in the next step.

$^1$H NMR (400 MHz, DMSO-d$_6$) δ: 1.42 (s, 9 H) 1.84 (d, J=3.03 Hz, 4 H) 2.74-3.01 (m, 2H) 4.05 (d, J=12.13 Hz, 2 H) 4.33-4.57 (m, 3 H) 5.25 (m, J=5.60, 5.60 Hz, 1 H) 6.13 (d, J=1.00 Hz, 1 H) 7.35 (d, J=1.00 Hz, 1 H)

Sodium hydride (51.2 mg, 1.28 mmol) was added to a solution of tert-butyl 4-(5-(hydroxymethyl)-1H-pyrazol-1-yl)piperidine-1-carboxylate (300 mg, 1.07 mmol) in THF (2 mL) under nitrogen. The reaction was stirred at room temperature for 0.5 hours. Methyl iodide (0.067 mL, 1.07 mmol) was added and stirring continued for 17 hours. More methyl iodide (0.067 mL, 1.07 mmol) was added and stirring continued for 5 hours. The reaction mixture was partitioned between DCM and water and the organic phase dried (hydrophobic frit). The solvent was removed in vacuo and the resulting residue purified by column chromatography on silica (10 g), eluted with 0-100% petrol/ethyl acetate to afford tert-butyl 4-(5-(methoxymethyl)-1H-pyrazol-1-yl)piperidine-1-carboxylate (174 mg, 55.2%) as a colourless liquid.

$^1$H NMR (400 MHz, DMSO-d$_6$) δ 1.42 (s, 9 H) 1.81 (d, J=3.54 Hz, 4 H) 2.73-3.01 (m, 1 H) 3.24 (s, 3 H) 3.91-4.12 (m, 2 H) 4.28-4.52 (m, 3 H) 6.23 (d, J=1.26 Hz, 1 H) 7.40 (d, J=1.26 Hz, 1 H)

4M Hydrochloric acid in dioxane (0.719 mL, 2.88 mmol) was added to a solution of tert-butyl 4-(5-(methoxymethyl)-1H-pyrazol-1-yl)piperidine-1-carboxylate (170 mg, 0.576 mmol) in dioxane (2 mL). The reaction was stirred at room temperature for 20 hours after which the solvent removed in vacuo to afford 4-(5-(methoxymethyl)-1H-pyrazol-1-yl)piperidine hydrochloride, Intermediate 7 (133 mg, quantitative yield)

$^1$H NMR (400 MHz, DMSO-d$_6$) δ: 1.98 (m, J=12.10 Hz, 2 H) 2.14-2.29 (m, 2 H) 2.93-3.17 (m, 2 H) 3.25 (s, 3 H) 3.40 (m, J=12.60 Hz, 2 H) 4.40-4.62 (m, 3 H) 6.27 (d, J=1.52 Hz, 1 H) 7.45 (d, J=1.26 Hz, 1 H)

Intermediate 8

Preparation of ethyl 4-(4-(2-hydroxypyridin-3-yl)piperidin-1-yl)azepane-1-carboxylate Example 35

HCl in dioxane →

Intermediate 8

A suspension of ethyl 4-(4-(2-methoxypyridin-3-yl)piperidin-1-yl)azepane-1-carboxylate (Example 35, 50 mg, 0.138 mmol) and 4M HCl in dioxane (0.173 mL, 0.692 mmol) in Dioxane (1 mL) was heated under microwave irradiation at 100° C. for 0.5 hours. Solvent removed in vacuo and residue purified by reverse phase preparative HPLC eluted with acetonitrile/water (with 0.1% ammonia) to afford ethyl 4-(4-(2-hydroxypyridin-3-yl)piperidin-1-yl)azepane-1-carboxylate (21 mg, 44%), Intermediate 8, as a white solid.

$^1$H NMR (400 MHz, acetonitrile-d3) δ 1.24 (t, J=6.82 Hz, 3 H) 1.39-1.94 (m, 8 H) 2.08-2.23 (m, 2 H) 2.35 (m, J=11.00, 11.00, 11.00 Hz, 2 H) 2.46-2.56 (m, 1 H) 2.61-2.74 (m, 1 H) 2.79-2.94 (m, 2 H) 3.20-3.32 (m, 2 H) 3.43-3.59 (m, 2 H)

4.09 (q, J=6.82 Hz, 2 H) 6.16 (t, J=6.69 Hz, 1 H) 7.15 (dd, J=6.57, 1.52 Hz, 1 H) 7.26 (d, J=6.57 Hz, 1 H) ES+=348.4

Intermediates 9 and 10

Preparation of tert-butyl 4-(2-chloropyridin-3-yl)piperidine-1-carboxylate and ethyl 4-(4-(2-chloropyridin-3-yl)piperidin-1-yl)azepane-1-carboxylate

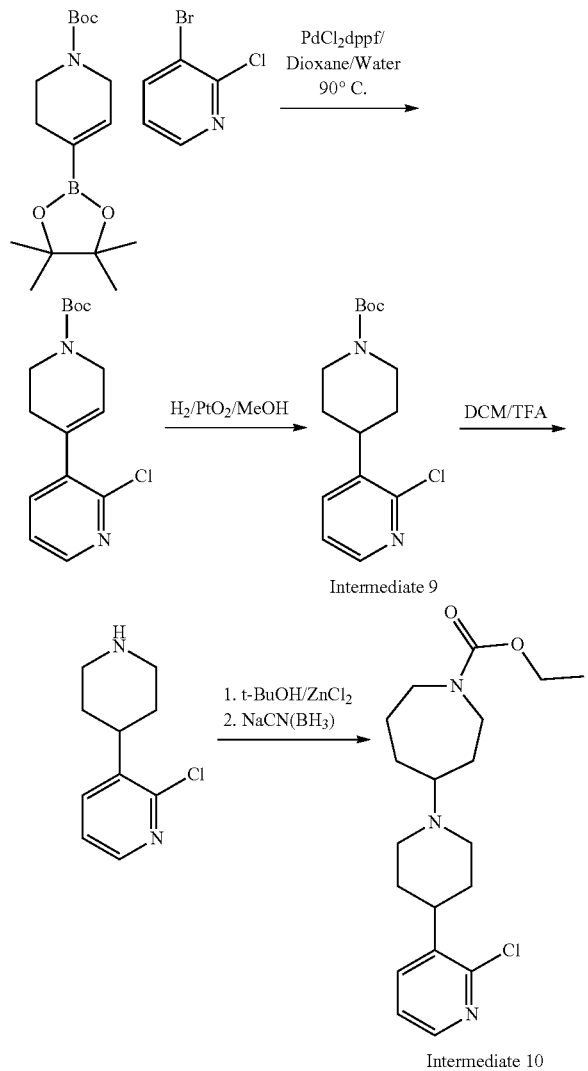

Intermediate 9

Intermediate 10

3-Bromo-2-chloropyridine (3.11 g, 16.17 mmol), tert-butyl 4-(4,4,5,5-tetramethyl-1,3,2-dioxaborolan-2-yl)-5,6-dihydropyridine-1(2H)-carboxylate (5 g, 16.17 mmol) and K₃PO₄ (10.284 g, 48.51 mmol, 3 eq.) were added to Dioxane:Water (60 mL:15 mL). Reaction mixture was degassed by purging with N₂ gas for 10 min. PdCl₂(dppf) (0.591 g, 0.80 mmol, 0.05 Eq.) was added to above reaction mixture at room temperature under N₂ and stirred for 3 h at 100° C. The reaction mixture was poured onto water (150 mL) and extracted with ethyl acetate (3×50 mL), combined organic layers were washed with brine, dried over sodium sulfate and concentrated in vacuo. The crude product was purified by column chromatography using neutral silica gel of 60-120 mesh size. 5-10% EtOAc in Hexane was used as gradient for elution of tert-butyl 2-chloro-5',6'-dihydro-[3,4'-bipyridine]-1'(2'H)-carboxylate (4.35 g, 91%).

tert-Butyl 2-chloro-5',6'-dihydro-[3,4'-bipyridine]-1'(2'H)-carboxylate (4.35 g, 14.7 mmol) was dissolved in MeOH (50 mL) and Platinum oxide (20%) was added at RT. The reaction was stirred at room temperature for 2 h under 50-70 psi hydrogen pressure. The crude product was purified by column chromatography using neutral silica gel of 100-200 mesh size. 0-25% EtOAc in Hexane was used as gradient for elution of tert-butyl 4-(2-chloropyridin-3-yl)piperidine-1-carboxylate, Intermediate 9 (3.7 g, 75%). Trifluoroacetic acid (30 mL) was added to a solution of tert-butyl 4-(2-chloropyridin-3-yl)piperidine-1-carboxylate (3.7 g, 12.47 mmol) in DCM (35 mL) at 0-5° C. Reaction mixture was stirred at RT for 1 h. The reaction mixture was poured into cold water (100 mL) and neutralized with solid K₂CO₃. Aq. phase was extracted with DCM (3×50 mL), combined organic layer was washed with brine, dried over sodium sulfate and concentrated in vacuo to obtain 2-chloro-3-(piperidin-4-yl)pyridine (2.0 g, 82%). 2-chloro-3-(piperidin-4-yl)pyridine was directly used in next step without any further purification. 2-Chloro-3-(piperidin-4-yl)pyridine (1.8 g, 9.15 mmol), ethyl 4-oxoazepane-1-carboxylate (2.03 g, 10.98 mmol) and Zinc Chloride (0.5 M solution in THF, 18.3 mL) were added to dry t-Butanol (50 mL). The reaction was flushed with N₂ gas and heated at vigorous reflux (external temp 120° C.) for 5 h. Reaction mixture was cooled down to 0° C. and Sodium cyanoborohydride (1.15 g, 18.3 mmol) was added portion wise. The reaction was stirred overnight at room temperature. The reaction mixture was poured onto water (100 mL) and extracted with ethyl acetate (3×30 mL), combined organic layer was washed with brine, dried over sodium sulfate and concentrated in vacuo.

The crude product was purified by column chromatography using neutral silica gel of 100-200 mesh size. 0-40% Acetone in DCM was used as gradient for elution of ethyl 4-(4-(2-chloropyridin-3-yl)piperidin-1-yl)azepane-1-carboxylate, Intermediate 10 (1.5 g, 45%).

Intermediate 11

Preparation of 5-methoxy-2-methyl-4-(piperidin-4-yl)pyrimidine

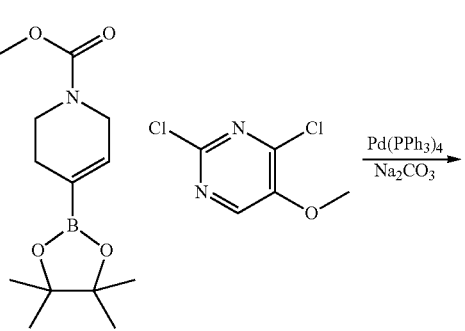

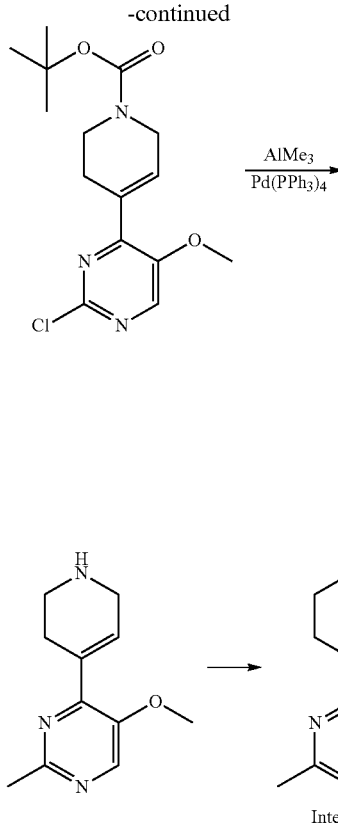

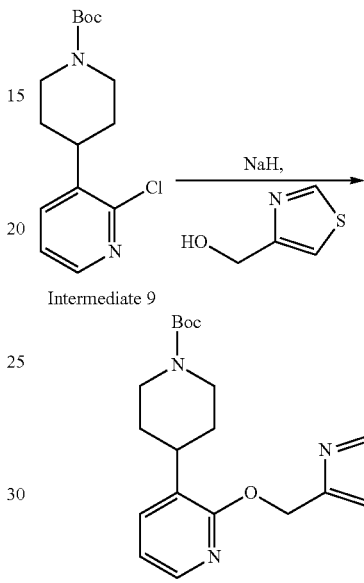

Intermediate 11 (207 mg, 62%).

ES+=208.2

Intermediate 12

Preparation of 4-(((3-(piperidin-4-yl)pyridin-2-yl)oxy)methyl)thiazole

A solution of 2,4-dichloro-5-methoxypyrimidine (0.579 g, 3.23 mmol), tert-butyl 4-(4,4,5,5-tetramethyl-1,3,2-dioxaborolan-2-yl)-5,6-dihydropyridine-1(2H)-carboxylate (1 g, 3.23 mmol), Pd(Ph$_3$P)$_4$ (0.037 g, 0.032 mmol) and Na$_2$CO$_3$ solution (4 mL) in Dioxane (8 mL) was heated under microwave irradiation at 100° C. for 0.5 hours. Reaction mixture was partitioned between DCM and water and organic phase dried (hydrophobic frit) and concentrated in vacuo. Synthesis was continued without further purification.

ES+=270.2/272.2 (−tBu)

Trimethylaluminium (1.615 ml, 3.23 mmol) was added to a suspension of tert-butyl 4-(2-chloro-5-methoxypyrimidin-4-yl)-5,6-dihydropyridine-1(2H)-carboxylate (0.526 g, 1.615 mmol) and Pd(Ph$_3$P)$_4$ (0.093 g, 0.081 mmol) in THF (3 mL) under nitrogen. The reaction was heated to 70° C. for 17 hours. Reaction mixture was added dropwise to ice water which was then acidified to pH-6 with 2M HCl and the solution loaded onto a cation exchange cartridge, washed with methanol and eluted with 2M ammonia/methanol solution then concentrated in vacuo.

ES+=206.2

A solution of 5-methoxy-2-methyl-4-(1,2,3,6-tetrahydropyridin-4-yl)pyrimidine (331 mg, 1.615 mmol) in Methanol (32 mL) was passed through a 10% Pd/C catcart in the H-cube (1 ml/min, full H$_2$, room temperature). The solution was cycled through with temperature at 40° C., for 3 hours. The solution was passed through a fresh 10% Pd/C catcart (1 ml/min, 20 bar hydrogen, 40° C.), then cycled through under these conditions for ~3 hours. Solvent removed in vacuo yielding 5-methoxy-2-methyl-4-(piperidin-4-yl)pyrimidine, Sodium hydride (29.6 mg, 0.741 mmol) was added to a solution of thiazol-4-ylmethanol (78 mg, 0.674 mmol) in dioxane (1.5 mL) under nitrogen. The reaction was warmed to 65° C. A solution of tert-butyl 4-(2-chloropyridin-3-yl)piperidine-1-carboxylate (Intermediate 9, 100 mg, 0.337 mmol) in dioxane (1.5 mL) was added and the reaction mixture was heated to reflux for 19 hours. The reaction mixture was allowed to cool, diluted with water (10 mL) and extracted with DCM (3×10 mL), then EtOAc (2×10 mL). The combined organics were concentrated in vacuo. The crude product was purified by column chromatography on silica, eluted with 0-50% ethyl acetate/petrol to afford tert-butyl 4-(2-(thiazol-4-ylmethoxy)pyridin-3-yl)piperidine-1-carboxylate (84 mg, 66.4%).

ES+=376.3

TFA (172 μl, 2.233 mmol) was added to an ice bath-cooled solution of tert-butyl 4-(2-(thiazol-4-ylmethoxy)pyridin-3-yl)piperidine-1-carboxylate (84 mg, 0.224 mmol) in DCM (1 mL). The reaction was stirred in the ice bath for 30 minutes, then allowed to warm to room temperature and stirred for a further hour. The mixture was diluted with water (25 mL), basified by addition of solid K$_2$CO$_3$ and extracted with ethyl acetate (2×25 ml). The combined organics were concentrated under a stream of dry nitrogen to afford 4-(((3-(piperidin-4-yl)pyridin-2-yl)oxy)methyl)thiazole, Intermediate 12 (28 mg, 45.5%)

ES+=276.3

Intermediate 13

Preparation of 1-(azetidin-3-yl)-1H-pyrazole hydrochloride

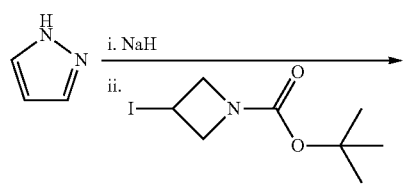

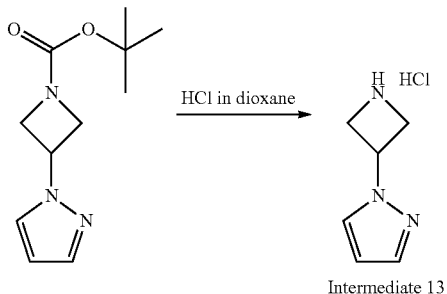

Intermediate 13

Sodium hydride (106 mg, 2.65 mmol) was added to a solution of 1H-pyrazole (120 mg, 1.766 mmol) in NMP (5 mL) in a microwave vial. The reaction was stirred at room temperature for 0.5 hours. tert-Butyl 3-iodoazetidine-1-carboxylate (500 mg, 1.77 mmol) was added and the vial sealed. The reaction was heated to 75° C. overnight. The reaction mixture was partitioned between DCM and water, and the organics purified by column chromatography on silica (25 g), eluting with 0-100% petrol/ethyl acetate to afford tert-butyl 3-(1H-pyrazol-1-yl)azetidine-1-carboxylate (250 mg, 63%) as a colourless oil.

$^1$H NMR (400 MHz, DMSO-d6) δ 1.41 (s, 9 H) 4.05-4.17 (m, 2 H) 4.28 (m, J=8.30, 8.30 Hz, 2 H) 5.06-5.30 (m, 1 H) 6.29 (t, J=1.89 Hz, 1 H) 7.57 (d, J=1.00 Hz, 1 H) 7.86 (d, J=2.27 Hz, 1 H)

4M HCl in dioxane (1.400 mL, 5.60 mmol) was added to a solution of tert-butyl 3-(1H-pyrazol-1-yl)azetidine-1-carboxylate (250 mg, 1.120 mmol) in dioxane (5 mL) and stirred for 17 h. The solvent was removed in vacuo and crude product, 1-(azetidin-3-yl)-1H-pyrazole hydrochloride, Intermediate 13, was used without further purification in the next step of synthesis (see general route i).

General Synthetic Procedures

Route a

Typical Procedure for the Preparation of Amines Via Reductive Alkylation with Intermediate 3, as Exemplified by the Preparation of Example 9, ethyl 4-[4-(1-methyl-1H-imidazol-2-yl)piperidin-1-yl]azepane-1-carboxylate

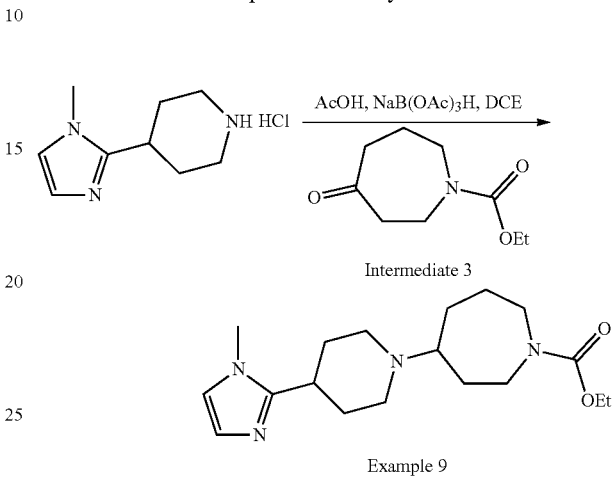

Example 9

To a solution of ethyl 4-oxoazepane-1-carboxylate (222 mg, 1.2 mmol) in 1,2-dichloroethane (10 mL) was added 4-(1-methyl-1H-imidazol-2-yl)piperidine hydrochloride (200 mg, 1.0 mmol) and acetic acid (69 µL, 1.2 mmol). The resultant reaction mixture was stirred at ambient temperature for a further 30 minutes. Sodium triacetoxyborohydride (254 mg, 1.2 mmol) was added to the reaction mixture. The reaction was then stirred until the reaction was complete (usually after 24 hours). The reaction mixture was purified by column chromatography (normal phase, [Biotage SNAP cartridge KP-sil 25 g, 40-63 µm, 60 Å, 25 mL per min, gradient 0% to 10% MeOH in DCM, then 7.5% (7N NH$_3$ in MeOH) in DCM] as eluent to give ethyl 4-[4-(1-methyl-1H-imidazol-2-yl)piperidin-1-yl]azepane-1-carboxylate as a colourless oil (110 mg, 33%). The data for the title compound are in Table 2 below.

Route b

Typical Procedure for the Preparation of Amines Via the Alkylation of Heterocycles, Deprotection and then Reductive Alkylation with Intermediate 3, as Exemplified by the Preparation of Example 10, ethyl 4-[4-(1-ethyl-1H-imidazol-2-yl)piperidin-1-yl]azepane-1-carboxylate

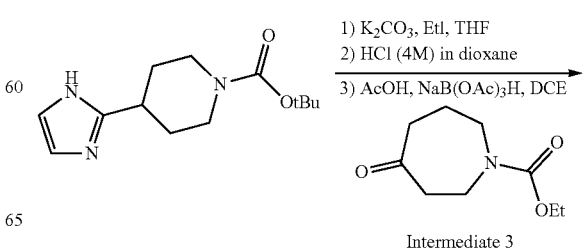

Intermediate 3

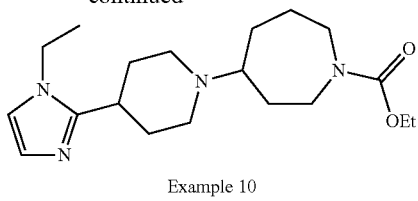

Example 10

To a mixture of tert-butyl-4-(1H-imidazol-2-yl)piperidine-1-carboxylate (250 mg, 1.0 mmol) and potassium carbonate (207 mg, 1.5 mmol) in THF (10 mL) was added iodoethane (96 µl, 1.2 mmol). The reaction mixture was then heated at 50° C. for 24 hours. Further iodoethane (200 µl, 2.5 mmol) was added and then heated at 50° C. for a further 24 hours. The reaction mixture was partitioned between DCM and water. The layers were separated using a phase separator, the solvent evaporated in vacuo from the organic phase to give a pale yellow oil (270 mg) which was used crude in the next step.

The crude material was dissolved in HCl in dioxane (4M, 10 mL) and then stirred at ambient temperature for 24 hours. The solvent was evaporated in vacuo, and then azeotroped using a solvent mixture of methanol:toluene (1:1) twice to give a yellow solid (210 mg) which was taken through to the next step without further purification.

The crude material was then reacted using the procedure described in route a to give ethyl 4-[4-(1-ethyl-1H-imidazol-2-yl)piperidin-1-yl]azepane-1-carboxylate as a light brown oil (130 mg, 37% over the 3 steps). The data for the title compound are in Table 2 below.

Route c

Typical Procedure for the Preparation of Amines Via the Alkylation of Heterocycles, Deprotection and then Reductive Alkylation with Intermediate 3, as Exemplified by the Preparation of Example 11, ethyl 4-[4-(1-propyl-1H-imidazol-2-yl)piperidin-1-yl]azepane-1-carboxylate

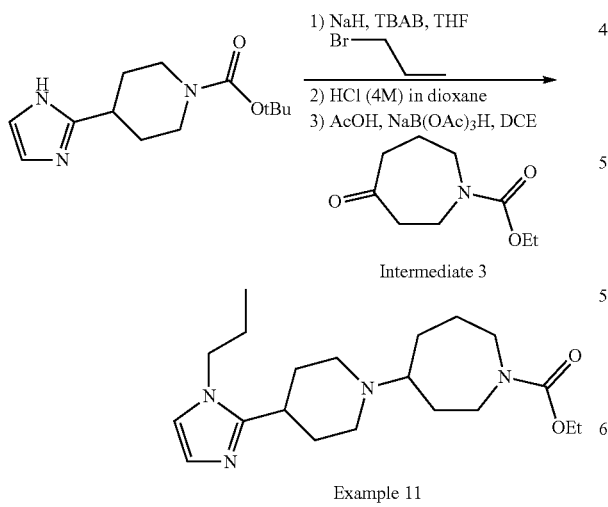

Example 11

To a mixture of tert-butyl-4-(1H-imidazol-2-yl)piperidine-1-carboxylate (200 mg, 0.8 mmol) and tetra n-butyl ammonium bromide (258 mg, 0.8 mmol) in THF (10 mL, anhydrous) under an atmosphere of nitrogen was added sodium hydride (64 mg, 1.6 mmol). The resultant mixture was stirred at ambient temperature for 10 minutes. 1-Bromopropane (109 µl, 1.2 mmol) was added and then the reaction mixture was heated at 60° C. for 24 hours. The reaction mixture was partitioned between DCM and water. The layers were separated using a phase separator, the solvent evaporated in vacuo from the organic phase to give an orange oil (210 mg) which was used without purification in the next step.

The crude material was dissolved in HCl in dioxane (4M, 10 mL) and then stirred at ambient temperature for 24 hours. The solvent was evaporated in vacuo, and then azeotroped using a solvent mixture of methanol:toluene (1:1) twice to give a yellow solid (210 mg) which was taken through to the next step without purification.

The crude material was then reacted using the procedure described in route a to give ethyl 4-[4-(1-propyl-1H-imidazol-2-yl)piperidin-1-yl]azepane-1-carboxylate as a light brown oil (30 mg, 10% over the 3 steps). The data for the title compound are in Table 2 below.

Route d

Typical Procedure for the Preparation of Biaryl Compounds by Suzuki Reaction of Boronic Acids with Intermediate 4, as Exemplified by the Preparation of Example 5, ethyl 4-(4-(5-(4-chlorophenyl)-1H-pyrazol-1-yl)piperidin-1-yl)azepane-carboxylate

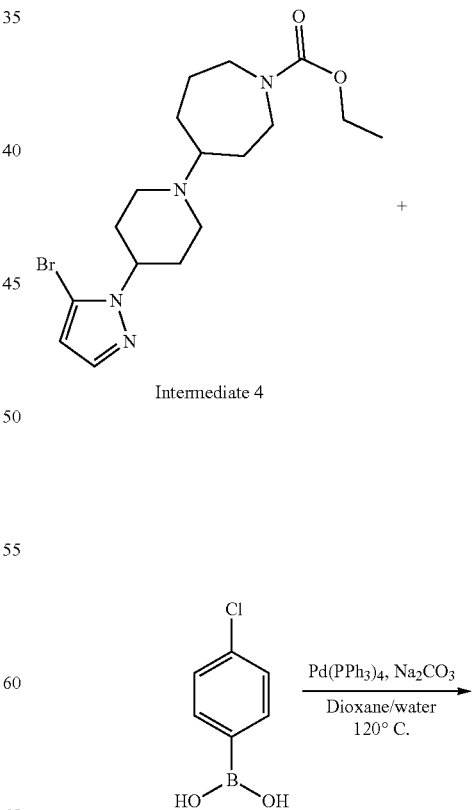

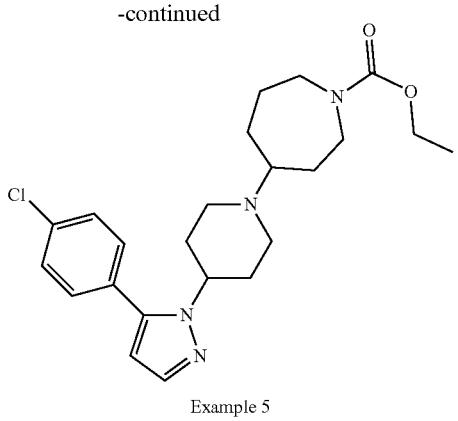

Example 5

A suspension of ethyl 4-(4-(5-bromo-1H-pyrazol-1-yl)piperidin-1-yl)azepane-1-carboxylate (54 mg, 0.14 mmol), 4-chlorophenyl)boronic acid (25.4 mg, 0.16 mmol), Pd(Ph$_3$P)$_4$ (7.81 mg, 6.76 µmol) and Na$_2$CO$_3$ (0.25 mL, 0.14 mmol) in dioxane (0.5 mL) was heated under microwave irradiation at 120° C. for 0.5 hours. The reaction mixture was then partitioned between DCM and water and the extracts dried (hydrophobic frit) and concentrated in vacuo. The crude product was purified by reverse phase preparative HPLC eluted with acetonitrile/water (with 0.1% ammonia) to afford ethyl 4-(4-(5-(4-chlorophenyl)-1H-pyrazol-1-yl)piperidin-1-yl)azepane-1-carboxylate (27 mg, 45.4%) as a yellow glass. The data for the title compound are in Table 2 below.

Route e

Typical Procedure for the Preparation of Oxadiazoles Via Intermediate 1 as Exemplified by the Preparation of Example 15, ethyl 4-(4-(5-isopropyl-1,3,4-oxadiazol-2-yl)piperidin-1-yl)azepane-1-carboxylate

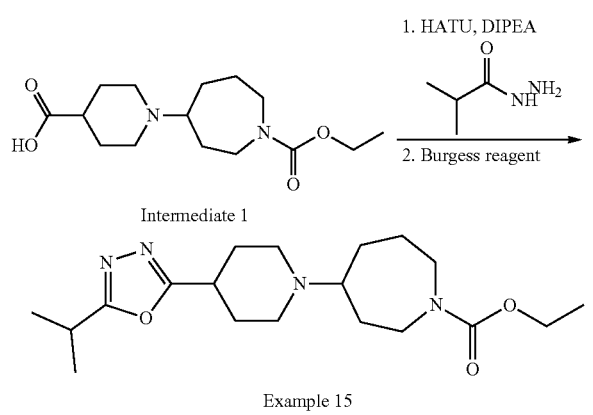

Example 15

1-(1-(Ethoxycarbonyl)azepan-4-yl)piperidine-4-carboxylic acid (200 mg, assumed 0.67 mmol), HATU (178 mg, 0.74 mmol), isobutyramidoxime (68.5 mg, 0.670 mmol) and DIPEA (128 µl, 0.74 mmol) in DMF (4 mL) were stirred at room temperature for 5 hours. The reaction mixture was concentrated in vacuo. Burgess reagent (259 mg, 1.09 mmol) was added and the reaction was heated at 80° C. for 3 days. A second amount of Burgess Reagent (164 mg, 0.69 mmol) was added and heating was continued at 80° C. for 1 day. A further portion of Burgess Reagent (100 mg, 0.42 mmol) was added and heating was continued at 80° C. for 1 day. The reaction mixture was concentrated in vacuo and the residue was purified by reverse phase column chromatography acidic 10 min [reverse phase HPLC (XSELECT CSH Prep 5 µm, 19×50 mm, 28 mL per min, gradient 5% MeCN in 0.1 HCOOH in water (30 secs), 5% to 40% (over 7 min) then 95% MeCN in 0.1 HCOOH in water (1 min) then 5% MeCN in 0.1 HCOOH in water (1.5 min)]. The residue was dissolved in DCM (10 mL) and washed with sat. NaHCO$_3$ sol. (2×2 mL). The phases were separated using a phase separation cartridge and the organic layer was concentrated in vacuo. The product was loaded onto a column of SCX (1 g) in 5% AcOH in MeOH. The column was washed with MeOH and then the product was eluted with 0.7 M ammonia in MeOH. The resultant mixture was concentrated in vacuo to afford ethyl 4-(4-(5-isopropyl-1,3,4-oxadiazol-2-yl)piperidin-1-yl)azepane-1-carboxylate (21.7 mg, 4% yield) as a brown oil. The data for the title compound are in Table 2 below.

Route f

Typical Procedure for Aminocarbonylation Reaction of Intermediate 4, as Exemplified by the Preparation of Example 24, ethyl 4-(4-(5-(((cyclopropylmethyl)carbamoyl)-1H-pyrazol-1-yl)piperidin-1-yl)azepane-1-carboxylate

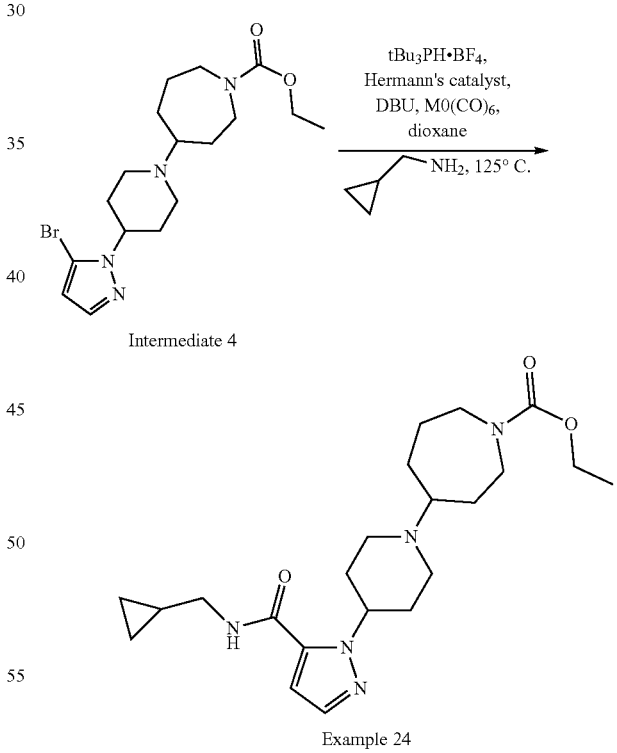

A suspension of tBu$_3$PH.BF$_4$ (1.090 mg, 3.76 µmol), Hermann's catalyst (1.174 mg, 1.25 µmol), DBU (12.77 mg, 0.084 mmol), Mo(CO)$_6$ (16.53 mg, 0.063 mmol), ethyl 4-(4-(5-bromo-1H-pyrazol-1-yl)piperidin-1-yl)azepane-1-carboxylate (50 mg, 0.125 mmol) and cyclopropylmethanamine (9 mg, 0.125 mmol) in dioxane (0.5 mL) was heated under microwave irradiation at 125° C. for 20 minutes. The reaction mixture was partitioned between DCM and water and combined organics dried (hydrophobic frit) and concentrated in vacuo. The crude product was purified by reverse phase preparative HPLC eluted with acetonitrile/water (with 0.1% ammonia) to afford ethyl 4-(4-(5-((cyclopropylmethyl)-carbamoyl) 1H-pyrazol-1-yl)piperidin-1-yl) azepane-1-carboxylate (10 mg, 19%). The data for the title compound are in Table 2 below.

Route g

Typical Procedure for Suzuki Reaction, Hydrogenation of Double Bond, Removal of N-Tert-Butoxycarbonyl Protecting Group to Give Piperidine Intermediate for Use in Route a, as Exemplified by the Preparation of Example 38, ethyl 4-[4-(3-methoxypyridin-2-yl)piperidin-1-yl]azepane-1-carboxylate

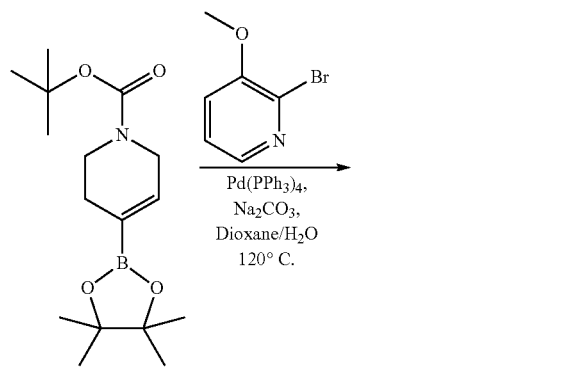

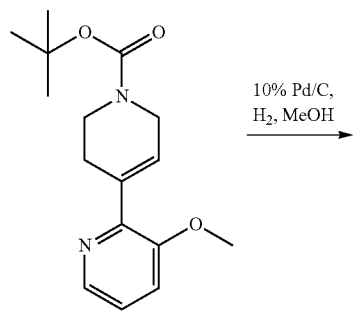

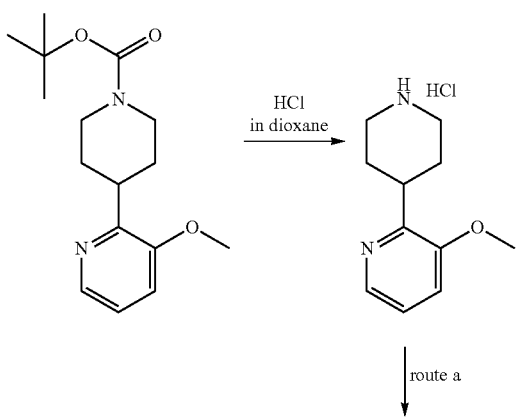

route a

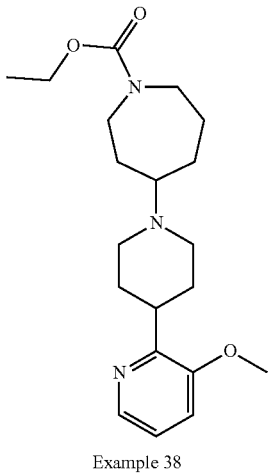

Example 38

A suspension of tert-butyl 4-(4,4,5,5-tetramethyl-1,3,2-dioxaborolan-2-yl)-5,6-dihydropyridine-1(2H)-carboxylate (250 mg, 0.81 mmol), Pd(Ph$_3$P)$_4$ (9.34 mg, 8.09 μmol) and Na$_2$CO$_3$ (1.5 mL, 0.81 mmol) in dioxane (3 mL) with 2-bromo-3-methoxypyridine (152 mg, 0.81 mmol)) was heated under microwave irradiation at 120° C. for 0.5 hours. The reaction mixture was partitioned between DCM and water. The organics were dried (hydrophobic frit) and concentrated in vacuo. The crude product was purified by column chromatography on silica, eluted with 0-50% petrol/ethyl acetate to afford tert-butyl 4-(3-methoxypyridin-2-yl)-1,2,3,6-tetrahydropyridine-1-carboxylate (215 mg, 92%)

$^1$H NMR (400 MHz, DMSO-d6) δ 1.44 (s, 9 H) 2.55 (m, J=1.80 Hz, 2 H) 3.30 (s, 3 H) 3.50 (t, J=5.56 Hz, 2 H) 3.95-4.11 (m, 2 H) 6.52 (br. s., 1 H) 7.25 (dd, J=8.34, 4.55 Hz, 1H) 7.45 (d, J=7.58 Hz, 1 H) 8.03-8.27 (m, 1 H)

A solution of tert-butyl 4-(3-methoxypyridin-2-yl)-1,2,3,6-tetrahydropyridine-1-carboxylate (220 mg, 0.76 mmol) in methanol (15.2 mL) was passed through a 10% Pd/C catcart in the H-cube (1 mL/min, full hydrogen mode, room temperature and atmospheric pressure). The solvent was removed in vacuo yielding tert-butyl 4-(3-methoxypyridin-2-yl)piperidine-1-carboxylate (200 mg, 90%)

$^1$H NMR (400 MHz, DMSO-d6) δ 1.35-1.44 (m, 9 H) 1.52-1.78 (m, 4 H) 3.11-3.27 (m, 1 H) 3.75-3.87 (m, 5 H) 4.05 (d, J=12.38 Hz, 2 H) 7.21 (m, J=8.30, 4.80 Hz, 1 H) 7.36 (m, J=7.60 Hz, 1 H) 8.08 (m, J=4.70, 0.90 Hz, 1 H)

4M HCl in dioxane (1 mL, 4.00 mmol) was added to a solution of tert-butyl 4-(3-methoxypyridin-2-yl)piperidine-1-carboxylate (200 mg, 0.68 mmol) in dioxane (5 mL). The reaction was stirred at room temperature for 17 hours after which the solvent was removed in vacuo, yielding 3-methoxy-2-(piperidin-4-yl)pyridine (132 mg, 100%)

$^1$H NMR (400 MHz, DMSO-d6) δ 1.91 (d, J=13.39 Hz, 2 H) 2.02-2.20 (m, 2 H) 2.92-3.11 (m, 2 H) 3.28-3.51 (m, 3 H) 3.90 (s, 3 H) 7.43-7.59 (m, 1 H) 7.75 (d, J=7.83 Hz, 1 H) 8.21 (d, J=4.80 Hz, 1 H) 9.18 (br. s., 2 H)

3-Methoxy-2-(piperidin-4-yl)pyridine was then used in route a to give the title compound, ethyl 4-[4-(3-methoxypyridin-2-yl)piperidin-1-yl]azepane-1-carboxylate, The data for the title compound are in Table 2 below.

Route h

Typical Procedure for Copper Coupling of Substituted Pyrazole with tert-butyl 4-(4,4,5,5-tetramethyl-1,3,2-dioxaborolan-2-yl)-5,6-dihydropyridine-1(2H)-carboxylate, Hydrogenation of Double Bond, Removal of N-Tert-Butoxycarbonyl Protecting Group to Give Piperidine Intermediate for Use in Reductive Amination and Separation of Regioisomers as Exemplified by the Preparation of Examples 12 and 16, ethyl 4-[4-(3-methyl-1H-pyrazol-1-yl)piperidin-1-yl]azepane-1-carboxylate and ethyl 4-[4-(5-methyl-1H-pyrazol-1-yl)piperidin-1-yl]azepane-1-carboxylate

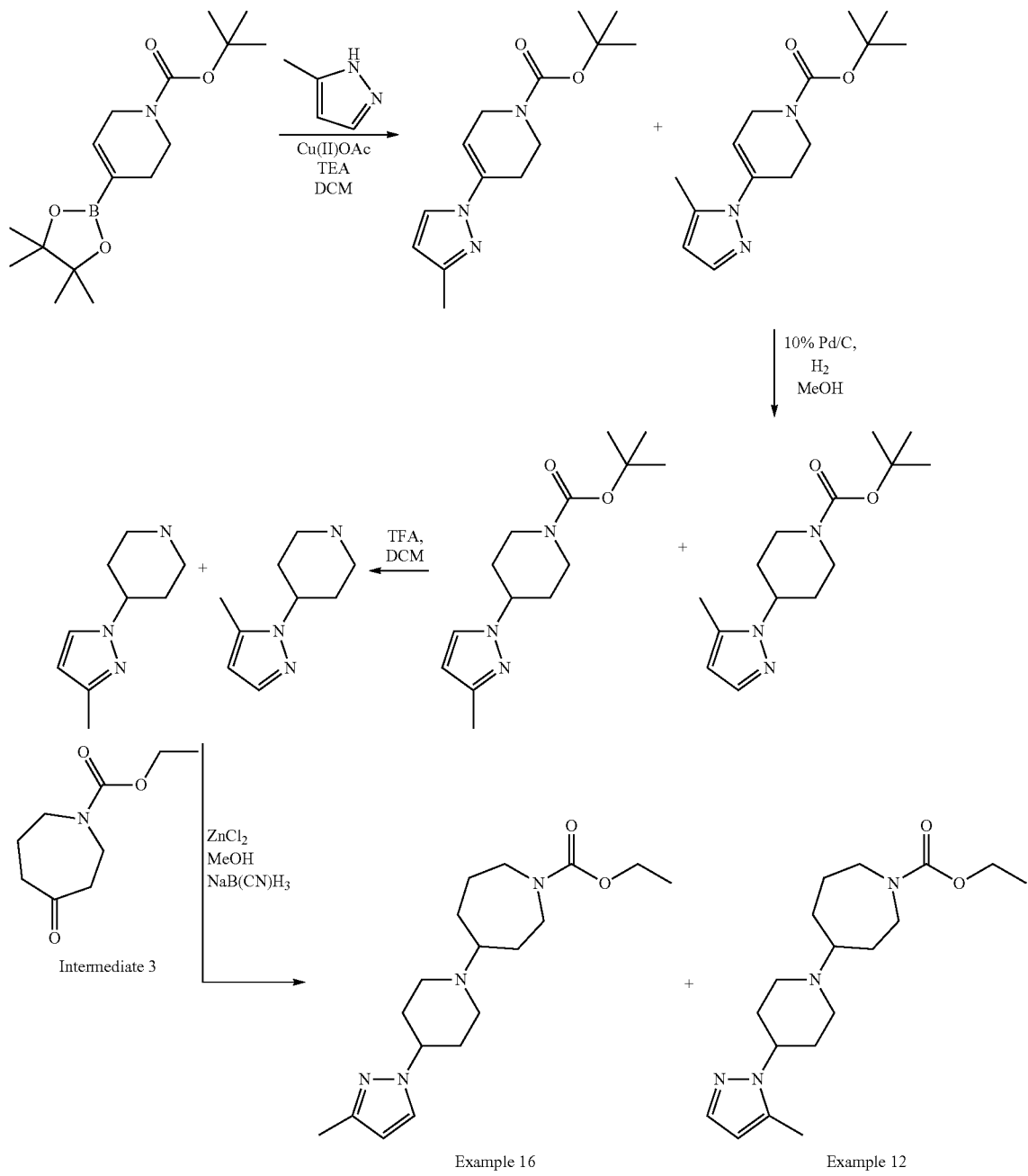

Example 16

Example 12 tert-Butyl 4-(4,4,5,5-tetramethyl-1,3,2-dioxaborolan-2-yl)-5,6-dihydropyridine-1(2H)-carboxylate (2 g, 6.47 mmol), 3-methyl-1H-pyrazole (0.584 g, 7.12 mmol), Cu(II)OAc (1.76 g, 9.7 mmol) and TEA (1.96 g, 19.4 mmol) were combined in anhydrous DCM (60 mL). The reaction mixture was stirred at room temperature for 24 h and then poured into water (100 mL). The aqueous layer was separated and extracted with (3×30 mL) of DCM. The combined organic layer was washed with brine, dried over sodium sulphate and concentrated in vacuo. The crude product was purified by column chromatography using neutral silica gel of 60-120 mesh size. 0-50% EtOAc in hexane was used as gradient for elution of the mixture of regioisomers (0.8 g, 47%).

The residue was dissolved in methanol (50 mL) and 10% Pd/C (80 mg) was added. Hydrogen gas was bubbled through the stirred solution for 3 h. The reaction mixture was filtered through a "Celite" (trade mark) pad and washed with excess of ethyl acetate. The filtrate was concentrated in vacuo and the residue used in the next step.

The residue (0.6 g, 2.26 mmol) was dissolved in DCM (50 mL) and cooled to 0° C. under a nitrogen atmosphere. TFA (6 mL) was added to the solution and the reaction mixture was allowed to attain room temperature and stirred for 45 min. The reaction mixture was poured into cold water (70 mL), neutralized with solid potassium carbonate and extracted with (3×30 mL) of DCM. The combined organic phase was washed with brine, dried over sodium sulphate and concentrated in vacuo. DCM (20 mL) was added and the residual solvent co-distilled with DCM to obtain crude product that was used in the next step without further purification.

The residue from the preceeding step (0.25 g, 1.51 mmol) and 1-carbethoxyazepan-4-one (0.336 g, 1.81 mmol) were dissolved in dry MeOH (50 mL). Zinc chloride (1 eq. 0.5 M in THF) was added and heated at 90° C. for 3 h under a nitrogen atmosphere. Sodium cyanoborohydride (0.19 g, 3.03 mmol) was added portion wise at 0° C. and allowed to stir at room temperature overnight. The reaction mixture was poured into water (100 mL) and extracted with (3×30 mL) of EtOAc. The combined organic layer was washed with brine and dried over sodium sulphate. The volatiles were evaporated under vacuum to obtain a mixture of crude products.

Product was purified by prep HPLC to give ethyl 4-[4-(3-methyl-1H-pyrazol-1-yl)piperidin-1-yl]azepane-1-carboxylate (0.085 g, 16.7% yield) and ethyl 4-[4-(5-methyl-1H-pyrazol-1-yl)piperidin-1-yl]azepane-1-carboxylate (0.04 g, 7.9%).

The data for the title compounds are in Table 2 below.

Route i

Typical Procedure for Reductive Amination of Amine with Tert-Butyl 4-Formylpiperidine-1-Carboxylate, N-Tert-Butoxycarbonyl Deprotection and Ethyl Carbamate Formation, as Exemplified by the Preparation of Example 29, ethyl 4-{[3-(1H-pyrazol-1-yl)azetidin-1-yl]methyl}piperidine-1-carboxylate

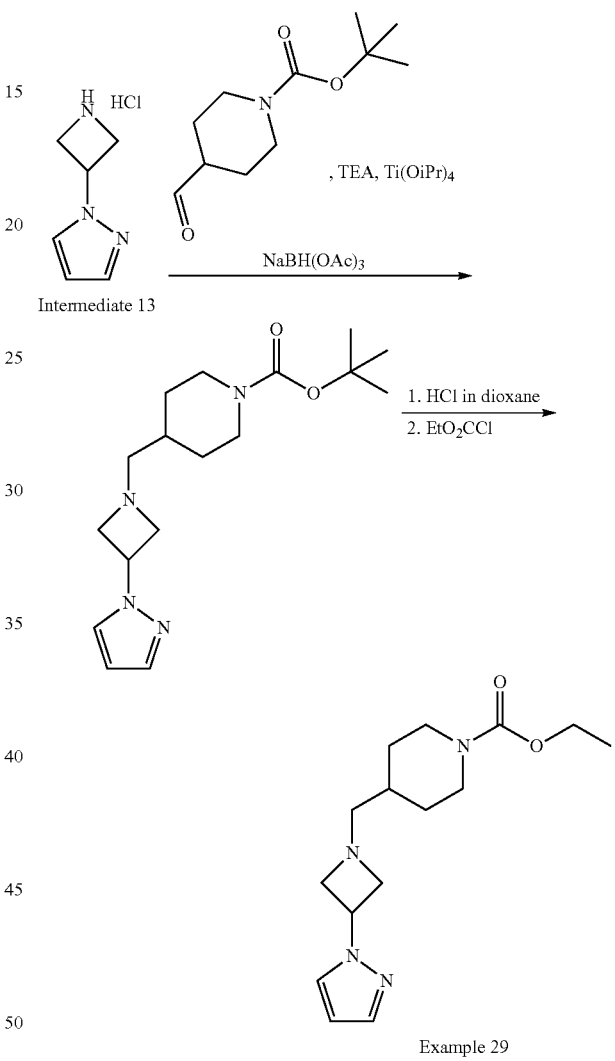

Example 29

Titanium(IV) isopropoxide (0.788 ml, 2.69 mmol) was added to a solution of 1-(azetidin-3-yl)-1H-pyrazole hydrochloride (1.12 mmol), TEA (0.187 ml, 1.344 mmol) and tert-butyl 4-formylpiperidine-1-carboxylate (239 mg, 1.120 mmol) in DCM (5 mL) under nitrogen. The reaction was stirred at room temperature for 1 hour. Sodium triacetoxyborohydride (1187 mg, 5.60 mmol) was added and stirring continued for 72 hours. Reaction mixture was quenched with sodium bicarbonate solution and washed with EtOAc. The aqueous phase was filtered and the filtrate was purified by reverse phase chromatography on C18 silica eluted with 5-95% water (with 0.05% ammonia)/acetonitrile to afford tert-butyl 4-((3-(1H-pyrazol-1-yl)azetidin-1-yl)methyl)piperidine-1-carboxylate (28 mg, 8% yield).

ES+=321.4

4M HCl in dioxane (0.109 mL, 0.437 mmol) was added to a solution of tert-butyl 4-((3-(1H-pyrazol-1-yl)azetidin-1-yl)methyl)piperidine-1-carboxylate (28 mg, 0.087 mmol) in dioxane (1 mL) and stirred at room temperature for 17 hours. Solvent was removed in vacuo. Residue was dissolved in DCM (1 mL) and TEA (0.5 ml, 3.59 mmol) and ethyl chloroformate (0.013 ml, 0.131 mmol) were added. After stirring for 2 hours, the reaction mixture was diluted with DCM and washed with water. The crude product was purified by reverse phase preparative HPLC eluted with acetonitrile/water (with 0.1% ammonia) to afford ethyl 4-((3-(1H-pyrazol-1-yl)azetidin-1-yl)methyl)piperidine-1-carboxylate (6 mg, 22%) as a colourless oil. The data for the title compound is in Table 2 below.
Route j Typical Procedure for O-Alkylation of Intermediate 8 with Sodium 2-Chloro-2,2-Difluoroacetate, as Exemplified by the Preparation of Example 52, ethyl 4-{4-[2-(difluoromethoxy)pyridin-3-yl]piperidin-1-yl}azepane-1-carboxylate

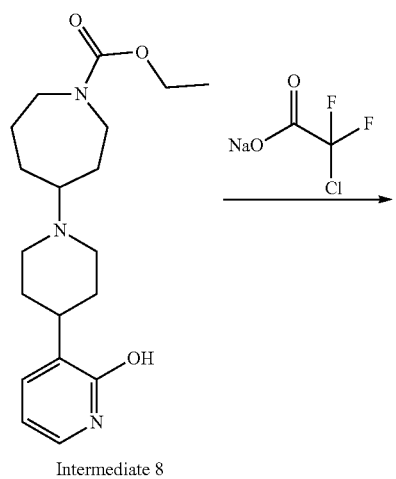

Intermediate 8

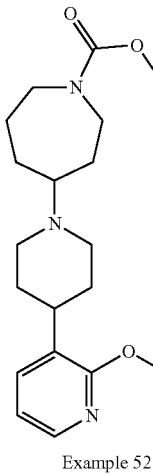

Example 52

A suspension of ethyl 4-(4-(2-hydroxypyridin-3-yl)piperidin-1-yl)azepane-1-carboxylate hydrochloride (50 mg, 0.130 mmol) and sodium 2-chloro-2,2-difluoroacetate (39.7 mg, 0.260 mmol) in acetonitrile (0.5 mL) was heated to 90° C. for 3 hours. Reaction mixture was partitioned between DCM and water and the organic phase was dried (hydrophobic frit) before purification by reverse phase preparative HPLC eluted with acetonitrile/water (with 0.1% ammonia) to afford ethyl 4-(4-(2-(difluoromethoxy)pyridin-3-yl)piperidin-1-yl)azepane-1-carboxylate (8 mg, 14%) as a yellow oil. The data for the title compound is in Table 2 below.
Route k Typical Procedure for O- and N-Alkylation of Intermediate 8 with Alkyl Halide, as Exemplified by the Preparation of Example 53, ethyl 4-(4-(2-ethoxypyridin-3-yl)piperidin-1-yl)azepane-1-carboxylate, and Example 57, ethyl 4-(4-(1-ethyl-2-oxo-1,2-dihydropyridin-3-yl)piperidin-1-yl)azepane-1-carboxylate Ethyl 4-(4-(2-hydroxypyridin-3-yl)piperidin-1-yl)azepane-1-carboxylate hydrochloride (59 mg, 0.154 mmol), ethyl iodide (72 mg, 0.46 mmol), silver carbonate (127 mg, 0.461 mmol) and THF (1 ml) were combined in a microwave vial, sealed and heated to 70° C. for 17 hours. Reaction mixture was partitioned between DCM and water and organics dried (hydrophobic frit) and concentrated in vacuo before purification by reverse phase preparative HPLC eluted with acetonitrile/water (with 0.1% ammonia) to afford ethyl 4-(4-(2-ethoxypyridin-3-yl)piperidin-1-yl)azepane-1-carboxylate (13 mg, 22%) and ethyl 4-(4-(1-ethyl-2-oxo-1,2-dihydropyridin-3-yl)piperidin-1-yl)azepane-1-carboxylate (9 mg, 16%). The data for the title compounds are in Table 2 below.

Route 1

Typical Procedure for Replacement of Bromo with Nitrile, as Exemplified by the Preparation of Example 27, ethyl 4-[4-(5-cyano-1H-pyrazol-1-yl)piperidin-1-yl]azepane-1-carboxylate

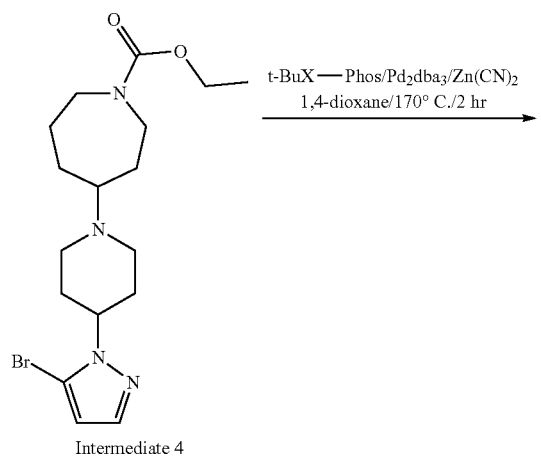

Intermediate 4

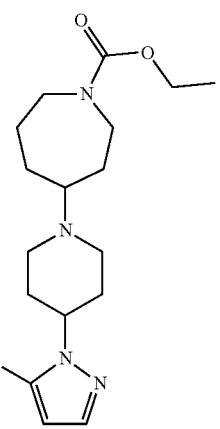

Example 27

Intermediate 4 (0.95 g, 2.37 mmol) was dissolved in 1,4-dioxane (25 mL) and degassed for min. Pd$_2$(dba)$_3$ (0.108 g, 0.12 mmol), t-BuX-Phos (0.101 g, 0.23 mmol), and Zn(CN)$_2$ (0.419 g, 3.56 mmol) were added to the reaction mixture and heated under microwave irradiation at 170° C. for 2 h. The reaction mixture was poured in water (100 mL) and extracted with (3×30 mL) of EtOAc. Combined organic layer was washed with brine, dried over sodium sulphate and concentrated in vacuo. The crude product was purified by column chromatography using neutral silica gel of 100-200 mesh size. 0-5% MeOH in DCM was used as gradient yielding ethyl 4-[4-(5-cyano-1H-pyrazol-1-yl)piperidin-1-yl]azepane-1-carboxylate (0.64 g, 77.8%). The data for the title compound is in Table 2 below.

Route m

Typical Procedure for Reduction of Nitrile, Followed by Amide Formation, as Exemplified by the Preparation of Example 28, ethyl 4-{4-[5-(acetamidomethyl)-1H-pyrazol-1-yl]piperidin-1-yl}azepane-1-carboxylate

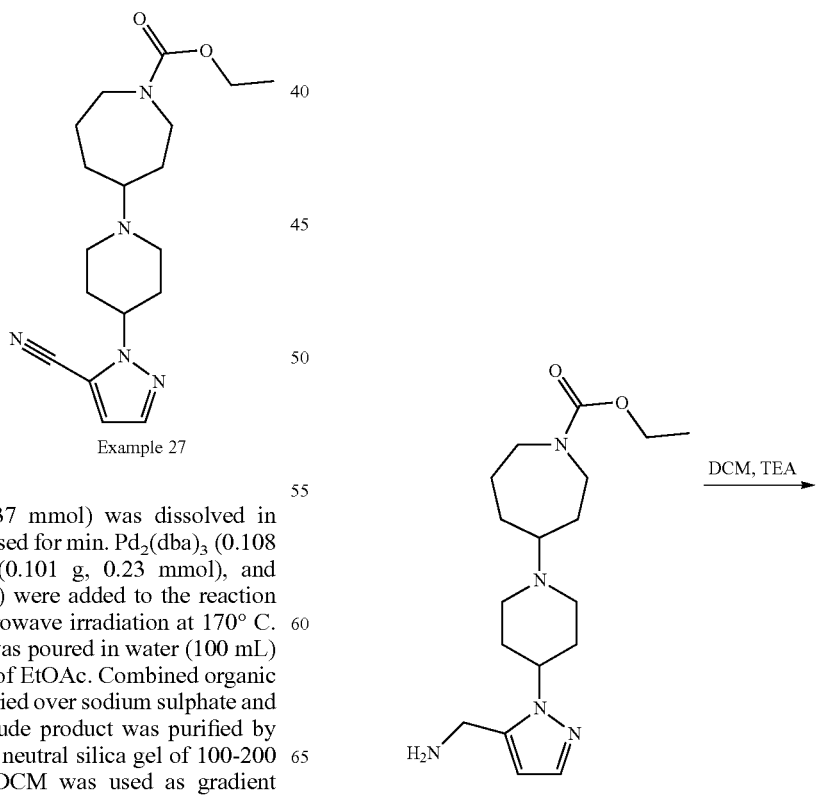

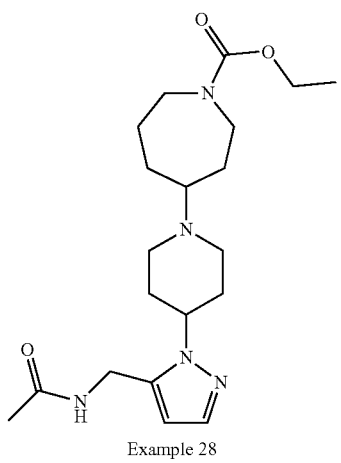

Example 28

Activated Raney Ni 200 mg (20% by wt) was added to solution of ethyl 4-[4-(5-cyano-1H-pyrazol-1-yl)piperidin-1-yl]azepane-1-carboxylate (0.95 g, 2.74 mmol) in MeOH (40 mL). Reaction mixture was stirred at RT overnight under 50 mm atmosphere H$_2$ pressure. Reaction mixture was filtered through "Celite" (trade mark) pad and washed with MeOH. Filtrate was concentrated in vacuo to give ethyl 4-(4-(5-(aminomethyl)-1H-pyrazol-1-yl)piperidin-1-yl) azepane-1-carboxylate (0.65 g, 67.6%).

$^1$H NMR (400 MHz, MeOD) δ 1.3 (t, 3H), 1.5-1.6 (m, 2H), 1.75 (m, 1H), 1.9-2.1 (m, 5H), 2.2 (m, 2H), 2.5-2.6 (m, 3H), 2.95 (b, 2H), 3.35 (m, 2H), 3.6 (m, 2H), 3.9 (s, 2H), 4.15 (m, 3H), 6.25 (d, 1H), 7.42 (d, 1H)

Acetyl chloride (0.026 g, 0.34 mmol) in DCM (0.5 mL) was added drop wise to a solution of ethyl 4-(4-(5-(aminomethyl)-1H-pyrazol-1-yl)piperidin-1-yl)azepane-1-carboxylate (0.1 g, 0.28 mmol) and TEA (0.086 g, 0.85 mmol) in DCM (20 mL) at 0° C. under nitrogen. Reaction mixture was then stirred at rt for 45 min, before dilution with DCM (100 mL). Organic layer was washed with water (2×50 mL), brine, dried over sodium sulphate and concentrated in vacuo. The crude product was purified by column chromatography using neutral silica gel of 100-200 mesh size. 0-8% MeOH (4 mL Aq. NH$_3$ in 100 mL MeOH) in DCM was used as gradient yielding ethyl 4-{4-[5-(acetamidomethyl)-1H-pyrazol-1-yl]piperidin-1-yl}azepane-1-carboxylate (0.06 g, 53.5%). The data for the title compound is in Table 2 below Route n Typical Procedure for Suzuki Reaction with Pyridyl Chloride, as Exemplified by the Preparation of Example 61, ethyl 4-(4-{2-[1-(propan-2-yl)-1H-pyrazol-4-yl]pyridin-3-yl}piperidin-1-yl)azepane-1-carboxylate

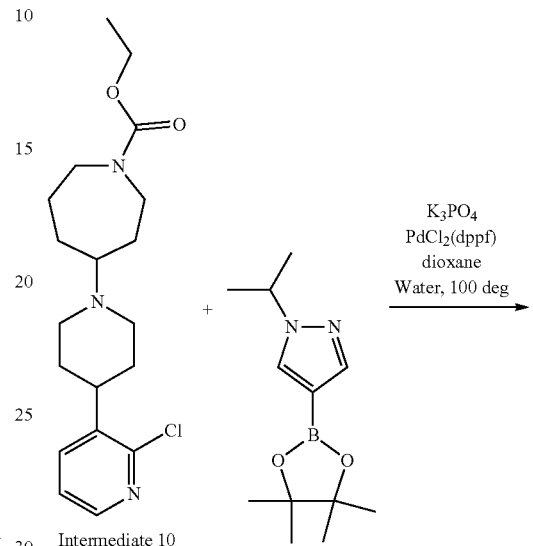

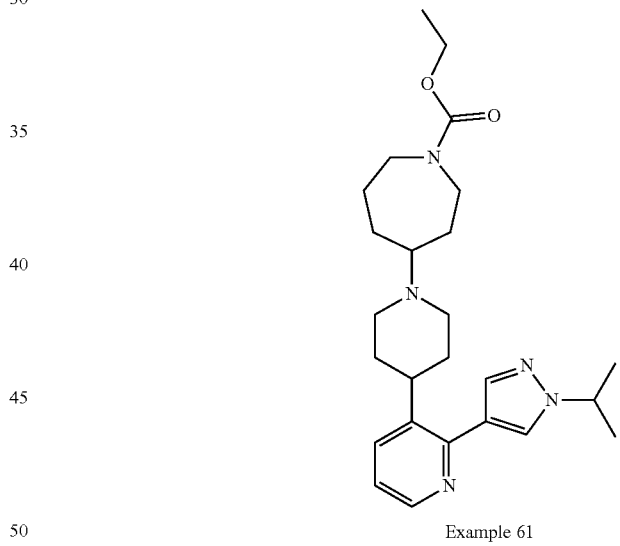

Example 61

1-isopropyl-4-boronicacid, pinacol ester (0.387 g, 1.63 mmol) was added to a mixture of ethyl 4-(4-(2-chloropyridin-3-yl)piperidin-1-yl)azepane-1-carboxylate (0.15 g, 0.409 mmol) and K$_3$PO$_4$ (0.695 g, 3.27 mmol) in Dioxane:Water (8 mL:2 mL). Reaction mixture was degassed using N$_2$ gas for 10 min. PdCl$_2$(dppf) (0.029 g, 0.0409 mmol) was added to a reaction mixture at RT under N$_2$. Reaction mixture was stirred for 3 h at 100° C. The reaction mixture was poured onto water (70 mL) and extracted with ethyl acetate (3×30 mL), combined organic layer was washed with brine, dried over sodium sulfate and concentrated in vacuo. The crude product was purified by column chromatography using neutral silica gel of 100-200 mesh size. 3-6% MeOH in DCM was used as gradient for elution of ethyl 4-(4-{2-[1-(propan-2-yl)-1H-pyrazol-4-yl]pyridin-3-yl}piperidin-1-yl)azepane-1-carboxylate (0.085 g, 47%). The data for the title compound is in Table 2 below Route p Typical Procedure for Buchwald Reaction of Pyridyl Chloride with Amine, as Exemplified by the Preparation of Example 62, ethyl 4-{4-[2-(methylamino)pyridin-3-yl]piperidin-1-yl}azepane-1-carboxylate

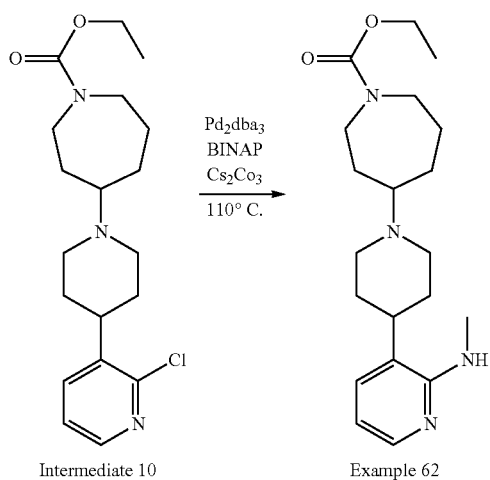 [SMILES: CCOC(=O)N1CCCC(N2CCC(c3cccnc3Cl)CC2)CC1 ; CCOC(=O)N1CCCC(N2CCC(c3cccnc3NC)CC2)CC1]

Ethyl 4-(4-(2-chloropyridin-3-yl)piperidin-1-yl)azepane-1-carboxylate (0.1 g, 0.27 mmol) and Cesium carbonate (0.356 g, 1.09 mmol) were added to dry Dioxane (5 mL). Reaction mixture was degassed under $N_2$ for 10 min. Methylamine hydrochloride (0.036 g, 0.54 mmol), $Pd_2dba_3$ (0.012 g, 0.0135 mmol) and BINAP (0.017 g, 0.027 mmol) were added under $N_2$. Reaction mixture was heated to 110° C. for 5 hr in sealed tube. The reaction mixture was poured onto water (70 mL) and extracted with ethyl acetate (3×30 mL), combined organic layer was washed with brine, dried over sodium sulfate and concentrated in vacuo. The crude product was purified by column chromatography using neutral silica gel of 100-200 mesh size. 0-8% MeOH (4 mL Aq. $NH_3$ in 100 mL MeOH) in DCM was used as gradient yielding ethyl 4-{4-[2-(methylamino)pyridin-3-yl]piperidin-1-yl}azepane-1-carboxylate (0.03 g, 35%). The data for the title compound is in Table 2 below.

Route q

Typical Procedure for Mesylation of N-Tert-Butoxycarbonyl 4-Hydroxypiperidine, Displacement of Mesyl Group with Substituted Pyrazole, N-Tert-Butoxycarbonyl Deprotection and Reductive Amination as Exemplified by Preparation of Intermediate 4, ethyl 4-(4-(5-bromo-1H-pyrazol-1-yl)piperidin-1-yl)azepane-1-carboxylate

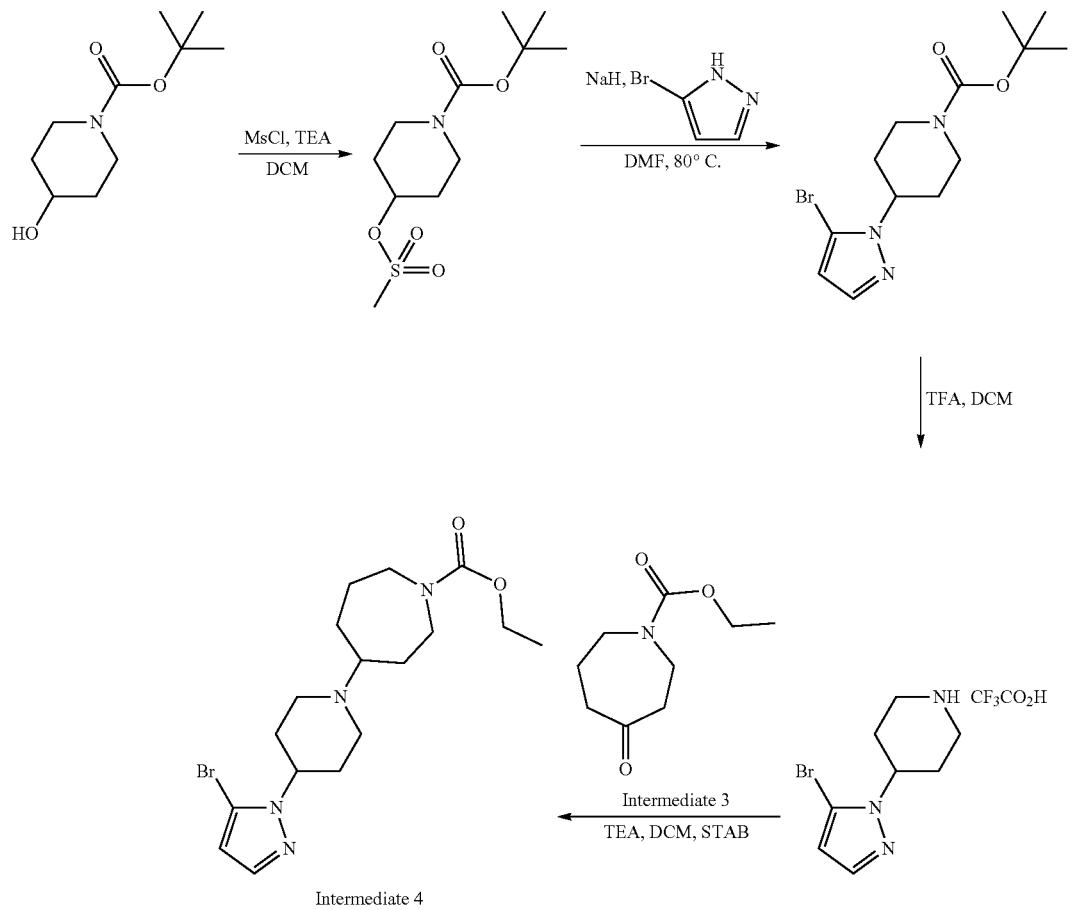

To a solution of tert-butyl 4-hydroxypiperidine-1-carboxylate (500 mg, 2.5 mmol) and TEA (0.346 mL, 2.5 mmol) in DCM (10 mL) was added methanesulphonyl chloride (0.2 mL, 2.5 mmol). The reaction mixture was stirred at rt for 1 h. The reaction was diluted with DCM, washed with water, dried (hydrophobic frit) and the organic phase concentrated in vacuo, yielding the crude product. This was used without further purification in the next reaction.

$^1$H NMR (400 MHz, DMSO-$d_6$) δ: 4.77-4.89 (m, 1H), 3.66 (d, J=8.8 Hz, 2H), 3.12-3.20 (m, 2H), 2.88-3.02 (m, 2H), 2.37 (s, 3H), 1.86-1.98 (m, 2H), 1.40-1.42 (m, 9H)

To a stirred solution of 3-bromo-1H-pyrazole (365 mg, 2.5 mmol) and sodium hydride (149 mg, 3.7 mmol) in DMF (5 mL) was added tert-butyl 4-((methylsulphonyl)oxy)-piperidine-1-carboxylate (694 mg, 2.5 mmol). The reaction mixture was stirred at 80° C. overnight. The reaction mixture was poured into water and extracted with EtOAc. The organic extracts were washed with brine, dried (hydrophobic frit) and concentrated in vacuo. The resulting residue was purified by flash chromatography (0-50% EtOAc in petrol) yielding the product tert-butyl 4-(5-bromo-1H-pyrazol-1-yl)piperidine-1-carboxylate (120 mg, 15%).

$^1$H NMR (400 MHz, DMSO-$d_6$) δ: 7.58 (d, J=1.5 Hz, 1H), 6.45 (d, J=1.8 Hz, 1H), 4.43-4.58 (m, 1H), 4.03-4.10 (m, 2H), 2.83-3.08 (m, 2H), 1.73-1.91 (m, 4H), 1.38-1.46 (m, 9H)

ES+=256.5 (MS-tBu)

A solution of tert-butyl 4-(5-bromo-1H-pyrazol-1-yl)piperidine-1-carboxylate (120 mg, 0.36 mmol) and TFA (0.56 mL, 7.3 mmol) in DCM (10 mL) were stirred at rt for 2 hours. The reaction mixture was concentrated in vacuo yielding the product 4-(5-bromo-1H-pyrazol-1-yl)-piperidine 2,2,2-trifluoroacetate as a colourless oil which was used in the next step without further purification.

$^1$H NMR (400 MHz, MeOD) δ: 7.59 (d, J=2.0 Hz, 1H), 6.42 (d, J=2.0 Hz, 1H), 4.78 (tt, J=10.6, 4.3 Hz, 1H), 3.60 (dt, J=13.2, 3.3 Hz, 2H), 3.26 (td, J=12.7, 3.2 Hz, 2H), 2.12-2.43 (m, 4H)

ES+=230.5[M+H]+

To a stirred solution of the 4-(5-bromo-1H-pyrazol-1-yl)-piperidine 2,2,2-trifluoroacetate (125 mg) and TEA (0.152 mL, 1.09 mmol) in THF (5 mL) was added ethyl 4-oxoazepane-1-carboxylate (67.3 mg, 0.36 mmol) and ethyl 4-oxoazepane-1-carboxylate (67.3 mg, 0.36 mmol). The reaction mixture was stirred at rt for 5 min. Sodium triacetoxyborohydride (123 mg, 0.58 mmol) was added and the reaction was stirred at rt overnight. The reaction was quenched with 2M NaOH and extracted with EtOAc. The organics were collected, dried (hydrophobic frit) and conc in vacuo. The resulting residue was taken up in THF (5 mL) and acetic acid (0.025 mL, 0.436 mmol) and sodium triacetoxyborohydride (123 mg, 0.581 mmol) were added and stirred at rt overnight. The reaction was quenched with 2M NaOH and extracted with EtOAc. The organics were collected, dried (hydrophobic frit) and concentrated in vacuo. The resulting residue was purified by reverse phase preparative HPLC eluted with acetonitrile/water (with 0.1% ammonia) yielding ethyl 4-[4-(5-bromo-1H-pyrazol-1-yl)piperidin-1-yl]azepane-1-carboxylate (18 mg, 12%).

$^1$H NMR (400 MHz, MeCN-$d_3$) δ: 7.45-7.59 (m, 1H), 6.29-6.41 (m, 1H), 4.27 (s, 1H), 4.04-4.15 (m, 2H), 3.44-3.58 (m, 2H), 3.21-3.37 (m, 2H), 2.91 (br. s., 2H), 2.54 (br. s., 1H), 2.33-2.48 (m, 2H), 2.00-2.11 (m, 2H), 1.81-1.93 (m, 6H), 1.44-1.74 (m, 2H), 1.16-1.28 (m, 3H)

ES+=399.6 [M+H]+

Route r

Typical Procedure for Negishi Reaction with Pyridyl Chloride, as Exemplified by the Preparation of Example 70, ethyl 4-[4-(2-ethylpyridin-3-yl)piperidin-1-yl]azepane-1-carboxylate

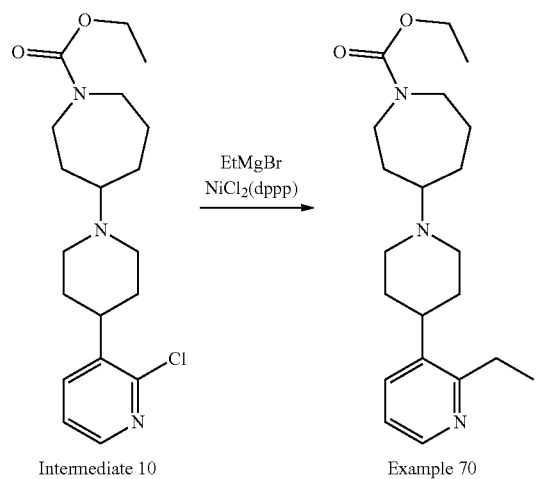 [SMILES: CCOC(=O)N1CCCC(N2CCC(c3cccnc3Cl)CC2)CC1 ; CCOC(=O)N1CCCC(N2CCC(c3cccnc3CC)CC2)CC1]

Intermediate 10    Example 70

Ethyl 4-(4-(2-chloropyridin-3-yl)piperidin-1-yl)azepane-1-carboxylate (0.1 g, 0.273 mmol) was dissolved in mixture of THF (3 mL) and diethyl ether (5 mL). Reaction mixture was degassed by nitrogen and cooled to 0° C. Catalyst NiCl$_2$(dppp) (0.007 g, 0.013 mmol) was added under nitrogen. After 10 min, ethylmagnesium bromide (1M in THF, 0.328 mL, 0.328 mmol) was added to reaction mixture at 0° C. The reaction temperature was raised to rt over 30 min. The reaction mixture was quenched by addition of a saturated solution of sodium bicarbonate (30 mL) and extracted by dichloromethane (2×25 ml). Organic phase was washed with brine, dried over sodium sulfate and concentrated in vacuo.

The residue was purified by column chromatography using neutral silica gel of 100-200 mesh size eluting with 0-5% MeOH (4 mL Aq. NH$_3$ in 100 mL MeOH) in DCM, yielding ethyl 4-[4-(2-ethylpyridin-3-yl)piperidin-1-yl] azepane-1-carboxylate (0.04 g, 36.59%). The data for the title compound is in Table 2 below.

Route s

Typical Procedure for Grignard Reaction with Pyridyl Chloride, as Exemplified by Preparation of Example 77, ethyl 4-{4-[2-(2-methylpropyl)pyridin-3-yl]piperidin-1-yl}azepane-1-carboxylate

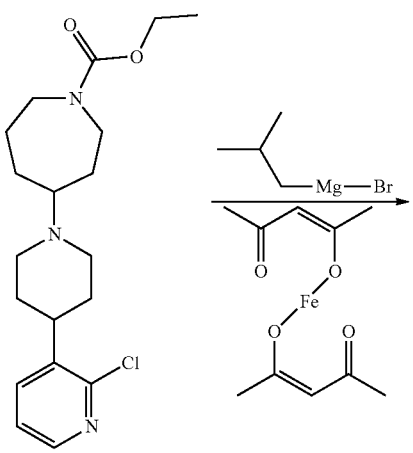

Intermediate 10

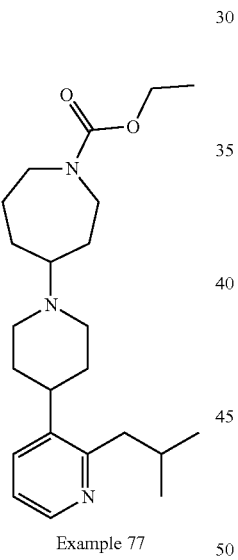

Example 77

Isobutylmagnesium chloride (2M in Et$_2$O, 0.273 ml, 0.547 mmol) was added dropwise to a solution of ethyl 4-(4-(2-chloropyridin-3-yl)piperidin-1-yl)azepane-1-carboxylate (100 mg, 0.273 mmol) and Fe(acac)$_2$ (69.4 mg, 0.273 mmol) in THF (2 mL) and N-methyl-2-pyrrolidinone (0.2 mL) under nitrogen. The reaction mixture was stirred at room temperature overnight. The reaction was quenched by addition of water (5 mL) and extracted with ethyl acetate (5×10 mL). The combined organics were filtered through a pad of diatomaceous earth and concentrated in vacuo. The crude product was purified by reverse phase preparative HPLC eluted with acetonitrile/water (with 0.1% ammonia) to afford ethyl 4-(4-(2-isobutylpyridin-3-yl)piperidin-1-yl)azepane-1-carboxylate (9 mg, 7.9%). The data for the title compound is in Table 2 below.

Route t

Typical Procedure for Stille Coupling of Stannane with Pyridyl Chloride, as Exemplified by Preparation of Example 80, ethyl 4-{4-[2-(1,3-oxazol-2-yl)pyridin-3-yl]piperidin-1-yl}azepane-1-carboxylate

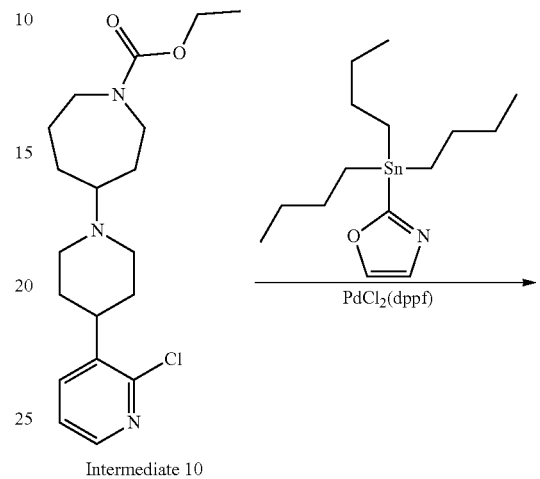

Intermediate 10

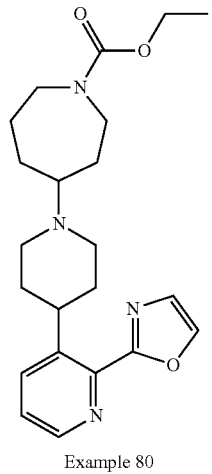

Example 80

PdCl$_2$(dppf) (20.00 mg, 0.027 mmol), then 2-(tributylstannyl)oxazole (0.167 ml, 0.547 mmol) were added to a degassed solution of ethyl 4-(4-(2-chloropyridin-3-yl)piperidin-1-yl)azepane-1-carboxylate (100 mg, 0.273 mmol) in 1,4-dioxane (2 mL). The mixture was heated under microwave irradiation at 140° C. for 30 minutes. The mixture was filtered through a pad of diatomaceous earth, washing with ethyl acetate and concentrated in vacuo. The crude product was purified by reverse phase preparative HPLC eluted with acetonitrile/water (with 0.1% ammonia) to afford ethyl 4-{4-[2-(1,3-oxazol-2-yl)pyridin-3-yl]piperidin-1-yl}azepane-1-carboxylate (46 mg, 40%). The data for the title compound is in Table 2 below.

Example 1 was prepared by route a using 4-(1-methyl-1H-imidazol-2-yl)piperidine, (CAS:1084976-68-0) and ethyl 4-oxopiperidine-1-carboxylate (CAS: 29976-53-2).

Example 2 was prepared by route c using Intermediates 6 and 3.

Example 3 was prepared by route a using 4-(1H-pyrrol-1-yl)piperidine (CAS: 169751-01-3) and Intermediate 3.

Example 4 was prepared by route a using 4-(1H-pyrazol-1-yl)piperidine (CAS:762240-09-5) and Intermediate 3.

Example 5 was prepared by route d as described above.

Example 6 was prepared by route a using 4-(1H-pyrazol-3-yl)piperidine (CAS:278798-08-6) and Intermediate 3

Example 7 was prepared by route d using (1-methyl-1H-pyrazol-5-yl)boronic acid, (CAS:720702-41-0) and Intermediate 4.

Example 8 was prepared by route a using 4-(4-(4-chlorophenyl)-1H-pyrazol-1-yl)piperidine CAS:902836-38-8 and Intermediate 3.

Example 9 was prepared by route a as described above.

Example 10 was prepared by route b as described above.

Example 11 was prepared by route c as described above.

Example 12 was prepared by route h as described above.

Example 13 was prepared by route a using Intermediates 2 and 3.

Example 14 was prepared by route a using 4-(1-methyl-1H-pyrazol-5-yl)piperidine (CAS:640270-01-5) and Intermediate 3.

Example 15 was prepared by route e as described above.

Example 16 was prepared by route h as described above.

Example 17 was prepared by route a using 4-(3-(thiophen-2-yl)-1H-pyrazol-5-yl)piperidine (CAS:321848-28-6) and Intermediate 3.

Example 18 was prepared by route a using 4-(4-(4-fluorophenyl)-1H-pyrazol-1-yl)piperidine (CAS: 1205747-45-0) and Intermediate 3.

Example 19 was prepared by route c using 2-chloro-N-cyclopropylacetamide (CAS:19047-31-5) and Intermediate 3.

Example 20 was prepared by route d using cyclopropylboronic acid (CAS:411235-57-9) and Intermediate 4.

Example 21 was prepared by route f using dimethylamine (CAS:124-40-3) and Intermediate 4.

Example 22 was prepared by route d using (1-isopropyl-1H-pyrazol-4-yl)boronic acid (CAS:1201643-90-4) and Intermediate 4.

Example 23 was prepared by route a using Intermediates 7 and 3.

Example 24 was prepared by route f as described above.

Example 25 was prepared by route d using (2,4-dimethylthiazol-5-yl)boronic acid (CAS:936361-37-4) and Intermediate 4.

Example 26 was prepared by route a using 2-(piperidin-4-yl)thiazole (CAS: 788822-03-7) and Intermediate 3.

Example 27 was prepared by route l as described above.

Example 28 was prepared by route m as described above.

Example 29 was prepared by route i as described above.

Example 30 was prepared by route a using 4-(piperidin-4-yl)pyridine (CAS:581-45-3) and Intermediate 3.

Example 31 was prepared by route a using 4-(piperidin-4-yl)pyridine (CAS:581-45-3) and ethyl 4-oxopiperidine-1-carboxylate (CAS: 29976-53-2).

Example 32 was prepared by route g using 2-bromo-6-methoxypyridine (CAS:40473-07-2) and ethyl 4-oxopiperidine-1-carboxylate (CAS: 29976-53-2).

Example 33 was prepared by route g using 2-bromo-6-methoxypyridine (CAS:40473-07-2) and Intermediate 3.

Example 34 was prepared by route g using 3-bromo-2-methoxypyridine (CAS:13472-59-8) and ethyl 4-oxopiperidine-1-carboxylate (CAS: 29976-53-2).

Example 35 was prepared by route g using 3-bromo-2-methoxypyridine (CAS:13472-59-8) and Intermediate 3.

Example 36 was prepared by route a using 2-methyl-4-(piperidin-4-yl)pyrimidine (CAS:949100-33-8) and ethyl 4-oxopiperidine-1-carboxylate (CAS: 29976-53-2).

Example 37 was prepared by route a using 4,6-dimethoxy-2-(piperidin-4-yl)pyrimidine (CAS:849924-99-8) and ethyl 4-oxopiperidine-1-carboxylate (CAS: 29976-53-2).

Example 38 was prepared by route g as described above.

Example 39 was prepared by route g using Intermediates 5 and 3.

Example 40 was prepared by route g using 2-bromo-3-methoxypyrazine (CAS: 1209905-41-8) and Intermediate 3.

Example 41 was prepared by route g using 3-bromo-2-methylpyridine (CAS:38749-79-0) and Intermediate 3.

Example 42 was prepared by route g using 3-bromo-2-ethoxy-5-methyl-pyridine (CAS:760207-82-7) and Intermediate 3.

Example 43 was prepared by route g using 3-bromo-2-methoxy-5-trifluoromethyl-pyridine (CAS:124432-63-9) and Intermediate 3.

Example 44 was prepared by route g using 4-bromo-3-methoxypyridine (CAS:109911-38-8) and Intermediate 3.

Example 45 was prepared by route g using 3-bromo-5-methoxypyridine (CAS:50720-12-2) and Intermediate 3.

Example 46 was prepared by route g using 3-bromo-2-methylpyridine (CAS:38749-79-0) and ethyl 4-oxopiperidine-1-carboxylate (CAS: 29976-53-2).

Example 47 was prepared by route g using 3-bromo-2-ethoxy-5-methyl-pyridine (CAS:760207-82-7) and ethyl 4-oxopiperidine-1-carboxylate (CAS: 29976-53-2).

Example 48 was prepared by route g using 3-bromo-4-methoxypyridine (CAS:82257-09-8) and Intermediate 3.

Example 49 was prepared by route a using N,N-dimethyl-3-(piperidin-4-yl)pyrazin-2-amine (CAS: 1316220-75-3) and Intermediate 3.

Example 50 was prepared by route a using N,N-dimethyl-6-(piperidin-4-yl)pyrazin-2-amine (CAS:1316227-13-0) and Intermediate 3.

Example 51 was prepared by route g using 5-bromo-4-methoxypyrimidine (CAS:4319-85-1) and Intermediate 3.

Example 52 was prepared by route j as described above.

Example 53 was prepared by route k as described above.

Example 54 was prepared by route k using 3-methyl-5-bromomethylisoxazole (CAS:36958-61-9) and Intermediate 8.

Example 55 was prepared by route k using 2-iodopropane (CAS:75-30-9) and Intermediate 8.

Example 56 was prepared by route k using 2-bromoacetonitrile (CAS:590-17-0) and Intermediate 8.

Example 57 was prepared by route k as described above.

Example 58 was prepared by route g using 3-bromo-5-chloro-2-methoxypyridine (CAS:102830-75-1) and Intermediate 3.

Example 59 was prepared by route g using 3-chloro-2,5-dimethylpyrazine (CAS:95-89-6) and Intermediate 3.

Example 60 was prepared by route g using 4-chloro-5-methoxy-2-(trifluoromethyl)pyrimidine (CAS:808770-41-4) and Intermediate 3.

Example 61 was prepared by route n using, 1-(1-methylethyl)-4-(4,4,5,5-tetramethyl-1,3,2-dioxaborolan-2-yl)-1H-pyrazole (CAS:879487-10-2) and Intermediate 10.

Example 62 was prepared by route p using methanamine hydrochloride (CAS:593-51-1) and Intermediate 10.

Example 63 was prepared by route a using Intermediates 3 and 11.

Example 64 was prepared by route n using 1-methyl-5-(4,4,5,5-tetramethyl 1,3,2-dioxaborolan-2-yl)-1H-pyrazole (CAS:847818-74-0) and Intermediate 10.

Example 65 was prepared by route p using N-methylnethanamine hydrochloride (CAS:506-59-2) and Intermediate 10.

Example 66 was prepared by route n using B-cyclopropylboronic acid (CAS:411235-57-9) and Intermediate 10.

Example 67 was prepared by route p using cyclopropanemethanmine (CAS:2516-47-4) and Intermediate 10.

Example 68 was prepared by route a using 4-(2-thiazolyl)piperidine (CAS:788822-03-7) and 4-oxo-1-piperidinecarboxylic acid, ethyl ester (CAS:29976-53-2).

Example 69 was prepared by route q using 3-(trifluoromethyl)-1H-pyrazole (CAS:20154-03-4) and Intermediate 3.

Example 70 was prepared by route r using bromoethylmagnesium (CAS:925-90-6) and Intermediate 10.

Example 71 was prepared by route g using 3-chloro-4-methoxypyridazine (CAS:1677-81-2) and Intermediate 3.

Example 72 was prepared by route g using 2-chloro-6-ethoxypyridine (CAS:42144-78-5) and Intermediate 3.

Example 73 was prepared by route n using B-(1-methyl-1H-pyrazol-4-yl)boronic acid (CAS:847818-55-7) and Intermediate 10.

Example 74 was prepared by route g using 2-chloropyrimidine (CAS:1722-12-9) and Intermediate 3.

Example 75 was prepared by route g using 5-bromo-4-methylpyrmidine (CAS:1439-09-4) and Intermediate 3.

Example 76 was prepared by route a using Intermediates 3 and 12.

Example 77 was prepared by route s using bromo(2-methylpropyl)magnesium (CAS:926-62-5) and Intermediate 10.

Example 78 was prepared by route i using 3,5-dimethyl-1-(3-pyrrolidinyl)-H-pyrazole (CAS: 177347-39-5), 4-formyl-1-piperidinecarboxylic acid, 1,1-dimethylethyl ester (CAS:137076-22-3) and carbonochloridic acid, methyl ester (CAS:79-22-1).

Example 79 was prepared by route i using 3,5-dimethyl-1-(3-pyrrolidinyl)-1H-pyrazole (CAS:1177347-39-5), 4-formyl-1-piperidinecarboxylic acid 1,1-dimethylethyl ester (CAS:137076-22-3) and carbonochloridic acid, ethyl ester (CAS:541-41-3).

Example 80 was prepared by route t using 2-(tributylstannyl)oxazole (CAS:145214-05-7) and Intermediate 10.

EXAMPLES 81 and 82

Enantiomers of the compound of Example 4 were prepared according to the following procedure:

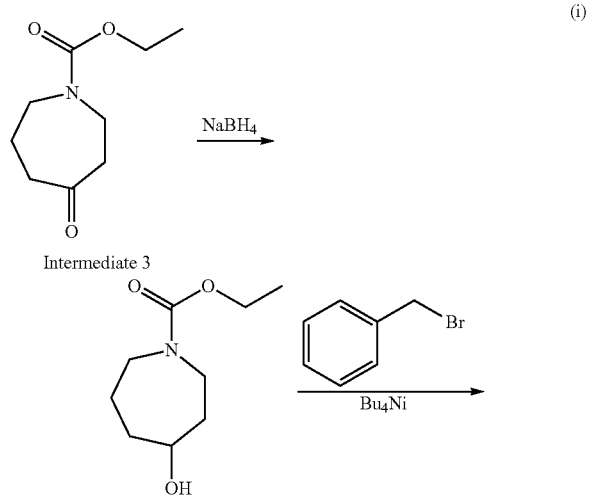

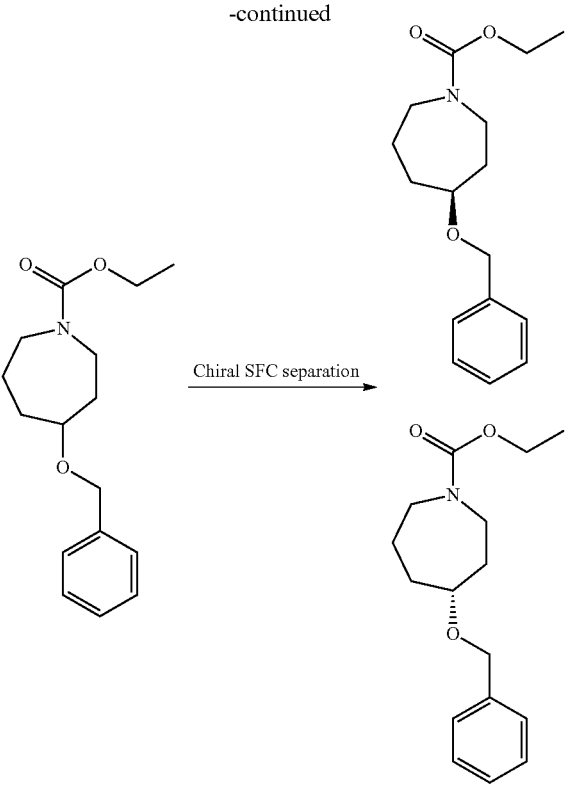

Sodium borohydride (0.837 g, 22.11 mmol) was added to an ice/water cooled solution of ethyl 4-oxoazepane-1-carboxylate (2.048 g, 11.06 mmol) in methanol (10 mL). After stirring under nitrogen for 2 h, reaction mixture was partitioned between water and EtOAc. The organic phase dried over $MgSO_4$ and solvent removed in vacuo yielding ethyl 4-hydroxyazepane-1-carboxylate (1.937 g, 94%).

$^1$H NMR (400 MHz, DMSO-$d_6$) δ ppm 1.18 (t, J=1.00 Hz, 3 H) 1.37-1.59 (m, 3 H) 1.60-1.70 (m, 1 H) 1.72-1.86 (m, 2 H) 3.07-3.31 (m, 2 H) 3.32-3.44 (m, 2 H) 3.64 (m, J=7.10, 3.50 Hz, 1 H) 3.94-4.09 (m, 2 H) 4.50 (m, J=3.40, 3.40 Hz, 1 H)

Sodium hydride (2.476 g, 61.9 mmol) was added to a suspension of ethyl 4-hydroxyazepane-1-carboxylate (1.932 g, 10.32 mmol) and TBAI (0.762 g, 2.064 mmol) in THF (50 mL) with ice/water cooling. After stirring for 30 minutes, (bromomethyl)benzene (5.29 g, 31.0 mmol) was added and the reaction left stirring for 16 hours. Solvent was removed in vacuo and the residue partitioned between DCM and water. The organics were concentrated in vacuo prior to purification by column chromatography on silica eluted with 0-30% petrol/ethyl acetate to afford ethyl 4-(benzyloxy)azepane-1-carboxylate (2.1 g, 73%).

$^1$H NMR (400 MHz, DMSO-$d_6$) δ ppm 1.16 (t, J=1.00 Hz, 3 H) 1.44-1.93 (m, 6 H) 3.20-3.46 (m, 4 H) 3.50-3.64 (m, 1 H) 4.03 (q, J=1.00 Hz, 2 H) 4.47 (s, 2 H) 7.15-7.47 (m, 5H)

1.95 g of Ethyl 4-(benzyloxy)azepane-1-carboxylate was separated by chiral SFC. The crude material was dissolved to 100 mg/ml and was then purified by SFC. Each injection was 0.4 mL (40 mg). The column used was a Lux Amylose 2 21.2×250 mm 5 um. The eluent was IPA 15%. No modifier was added and the flow rate was 60 ml/min. The fractions were concentrated in vacuo yielding Isomer 1 (689.8 mg, 71%, retention time=2.7 min) and Isomer 2 (704.2 mg, 72%, retention time=3.7 min).

The final analysis was performed by SFC using a Lux Amylose-2 4.6×250 mm 5 um. The eluent was IPA 15%. No modifier was added and the flow rate was 4 ml/min.

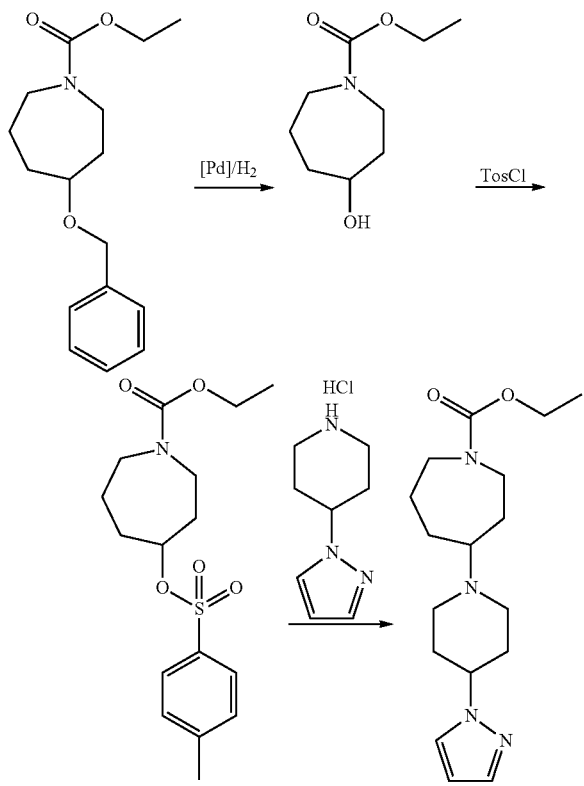

A solution of Isomer 2, ethyl 4-(benzyloxy)azepane-1-carboxylate (700 mg, 2.52 mmol) in MeOH (3 mL) was passed through a 10% Pd/C catcart in the H-cube (1 ml/min, 60° C., full H₂). The solvent was removed in vacuo yielding Isomer 2a, ethyl 4-hydroxyazepane-1-carboxylate (478 mg, 100%).

Mosher's esters ethyl 4-(((R)-3,3,3-trifluoro-2-methoxy-2-phenylpropanoyl)oxy)azepane-1-carboxylate and ethyl 4-(((S)-3,3,3-trifluoro-2-methoxy-2-phenylpropanoyl)oxy)azepane-1-carboxylate were prepared and analysed according to literature procedures (ref. Nature protocols, vol. 2, no. 10, 2007, 2451) which showed that Isomer 2a had the R configuration.

4-Methylbenzene-1-sulfonyl chloride (0.580 g, 3.04 mmol), (R)-ethyl 4-hydroxyazepane-1-carboxylate (0.475 g, 2.54 mmol) and pyridine (2 mL) were combined and stirred at room temperature for 3 h. The reaction mixture was partitioned between DCM and water and organics concentrated in vacuo. Purification by column chromatography, silica, eluting with petrol to EtOAc yielded (R)-ethyl 4-(tosyloxy)azepane-1-carboxylate (444 mg, 51%)

¹H NMR (400 MHz, DMSO-d₆) δ ppm 1.16 (t, J=1.00 Hz, 3 H) 1.37-1.90 (m, 6 H) 2.43 (s, 3 H) 3.19-3.44 (m, 4 H) 4.02 (q, J=1.00 Hz, 2 H) 4.54-4.79 (m, 1 H) 7.48 (d, J=8.08 Hz, 2 H) 7.79 (d, J=1.00 Hz, 2 H)

(R)-ethyl 4-(tosyloxy)azepane-1-carboxylate (50 mg, 0.146 mmol) and 4-(1H-pyrazol-1-yl)piperidine hydrochloride (55.0 mg, 0.293 mmol) were combined with KOH (41.1 mg, 0.732 mmol) in Acetonitrile (0.3 mL) in a sealed vial and heated to reflux for 4 hours. The reaction mixture was partitioned between DCM and water and the organic phase concentrated in vacuo. The crude product was purified by reverse phase preparative HPLC eluted with acetonitrile/water (with 0.1% ammonia) to afford ethyl (4S)-4-[4-(1H-pyrazol-1-yl)piperidin-1-yl]azepane-1-carboxylate (7 mg, 13%).

Ethyl (4R)-4-[4-(1H-pyrazol-1-yl)piperidin-1-yl]azepane-1-carboxylate was prepared in the same way from (S)-ethyl 4-(tosyloxy)azepane-1-carboxylate.

EXAMPLES 83 and 84 the enantiomers of the compound of Example 9 were prepared by processes analogous to those described above for the enantiomers of Examples 81 and 82.

EXAMPLES 85 and 86 the enantiomers of the compound of Example 35 were prepared by processes analogous to those described above for the enantiomers of Examples 81 and 82.

TABLE 2

| Ex. No. | Structure | Name | Intermediate | Synthetic method | $^1$H NMR | LCMS data |
|---|---|---|---|---|---|---|
| 1 | 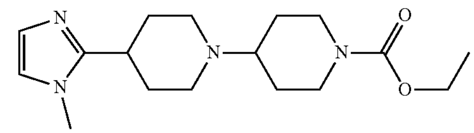 | ethyl 4-[4-(1-methyl-1H-imidazol-2-yl)piperidin-1-yl]piperidine-1-carboxylate | CAS: 1084976-68-0 and CAS: 29976-53-2 | a | $^1$H NMR (400 MHz, DMSO-d6) δ 1.15 (t, J = 6.9, 3H), 1.21-1.35-m, 2H), 1.58-1.75 (m, 4H), 2.15-2.29 (m, 2H), 2.31-2.44 (m, 1H), 2.60-2.76 (m, 4H), 2.81-2.89 (m, 2H), 3.45-3.60 (m, 3H), 3.53 (s, 3H), 3.98 (q, J = 6.9, 2H), 6.67 (s, 1H), 6.92 (s, 1H) | ES+ 321.2 |
| 2 | 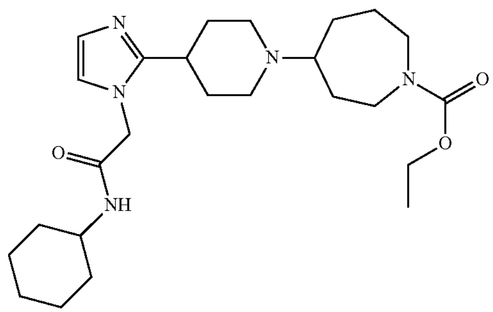 [SMILES: CCOC(=O)N1CCCC(N2CCC(c3nccn3CC(=O)NC3CCCCC3)CC2)CC1] | ethyl 4-(4-{1-[(cyclohexylcarbamoyl)methyl]-1H-imidazol-2-yl}piperidin-1-yl)azepane-1-carboxylate | Intermediates 6 and 3 | c | $^1$H NMR (CDCl$_3$-) δ 0.93-1.19 (m, 3H), 1.26-1.51 (m, 6H), 1.60-1.72 (m, 5H), 1.75-1.85 (m, 4H), 1.87-2.04 (m, 5H), 2.25-2.42 (m, 2H), 2.46-2.57 (m, 2H), 2.73-2.84 (m, 1H), 3.22-3.38 (m, 2H), 3.48-3.69 (m, 2H), 3.75-3.87 (m, 1H), 4.11-4.22 (m, 2H), 4.58 (s, 2H), 5.02-5.16 (m, 1H), 6.84 (s, 1H), 7.10 (s, 1H) | ES+ 460.8 |
| 3 | 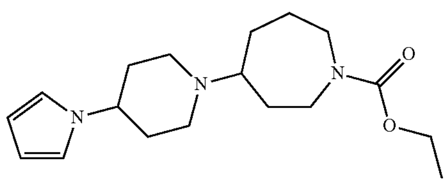 [SMILES: CCOC(=O)N1CCCC(N2CCC(n3cccc3)CC2)CC1] | ethyl 4-[4-(1H-pyrrol-1-yl)piperidin-1-yl]azepane-1-carboxylate | CAS: 169751-01-3 and Intermediate 3 | a | $^1$H NMR (400 MHz, DMSO-d6) δ 1.08-1.20 (m, 3H), 1.36-1.47 (m, 2H), 1.52-1.63 (m, 2H), 1.71-1.80 (m, 4H), 2.24-2.36 (m, 1H), 2.51-2.61 (m, 1H), 2.73-2.84 (m, 1H), 3.16-3.22 (m, 1H), 3.28-3.35 (m, 2H), 3.36-4.43 (m, 1H), 3.45-3.49 (m, 1H), 3.51-3.65 (m, 2H), 3.72-3.84 (m, 1H), 3.91-4.04 (m, 2H), 5.90-5.94 (m, 2H), 6.68-6.80 (m, 2H) | ES+ 320.1 |
| 4 | 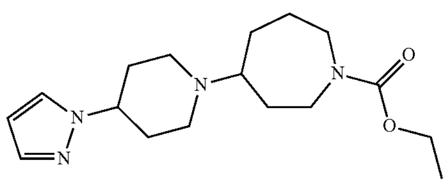 [SMILES: CCOC(=O)N1CCCC(N2CCC(n3cccn3)CC2)CC1] | ethyl 4-[4-(1H-pyrazol-1-yl)piperidin-1yl]azepane-1-carboxylate | CAS: 762240-09-5 and Intermediate 3 | a | $^1$H NMR (400 MHz, DMSO-d6) δ 1.15 (t, J = 7.3, 3H), 1.33-1.45 (m, 2H), 1.50-1.62 (m, 1H), 1.77-1.89 (m, 4H), 1.91-1.96 (m, 2H), 2.29-2.40 (m, 2H), 2.75-2.87 (m, 2H), 3.20 (m, 2H), 3.30-3.35 (m, 2H), 3.37-3.43 (m, 2H), 3.96-4.08 (m, 4H), 6.18 (m, 1H), 7.30-7.40 (m, 1H), 7.71 (m, 1H) | ES+ 321.1 |

TABLE 2-continued

| Ex. No. | Structure | Name | Intermediate | Synthetic method | ¹H NMR | LCMS data |
|---|---|---|---|---|---|---|
| 5 | 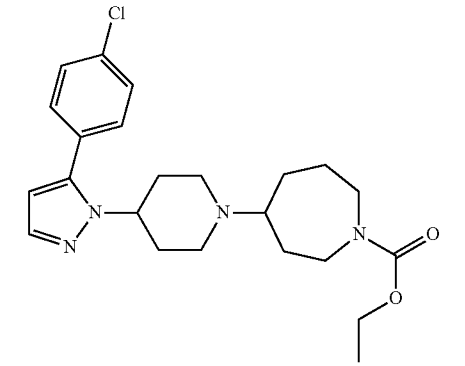 [SMILES: CCOC(=O)N1CCCC(N2CCC(n3nccc3-c3ccc(Cl)cc3)CC2)CC1] | ethyl 4-{4-[5-(4-chlorophenyl)-1H-pyrazol-1-yl]piperidin-1-yl}azepane-1-carboxylate | CAS: 1679-18-1 and Intermediate 4 | d | ¹H NMR (400 MHz, MeCN-d3) δ 1.23 (t, J = 7.07 Hz, 3H) 1.40-1.68 (m, 1H) 1.81 (d, J = 8.08 Hz, 5H) 2.09-2.33 (m, 6H) 2.41-2.60 (m, 1H) 2.85 (br. s., 2H) 3.28 (dd, J = 9.47, 4.17 Hz, 2H) 3.49 (br. s., 2H) 3.92-4.27 (m, 3H) 6.30 (d, J = 1.52 Hz, 1H) 7.41 (d, J = 8.59 Hz, 2H) 7.47-7.58 (m, 3H) | ES+ 431.4 |
| 6 | 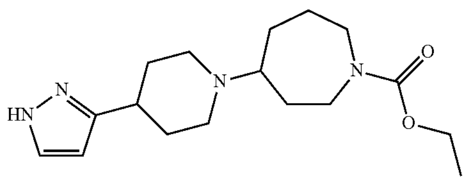 [SMILES: CCOC(=O)N1CCCC(N2CCC(c3cc[nH]n3)CC2)CC1] | ethyl 4-{4-(1H-pyrazol-3-yl)piperidin-1yl]azepane-1-carboxylate | CAS: 278798-08-6 and Intermediate 3 | a | ¹H NMR (400 MHz, DMSO-d6) δ 1.15 (t, J = 7.3, 3H), 1.32-1.42 (m, 2H), 1.45-1.57 (m, 4H), 1.70-1.83 (m, 4H), 2.17-2.29 (m, 2H), 2.33-2.45 (m, 2H), 2.48-2.60 (m, 2H), 2.66-2.77 (m, 2H), 3.12-3.22 (m, 1H), 3.34-3.46 (m, 2H), 3.94-4.03 (q, J = 7.3, 2H), 4.04-4.09 (m, 1H), 5.94-6.04 (br. s, 1H), 7.31-7.43 (br. s, 1H), 12.31-12.42 (br. s, 1H) | ES+ 321.2 |
| 7 | 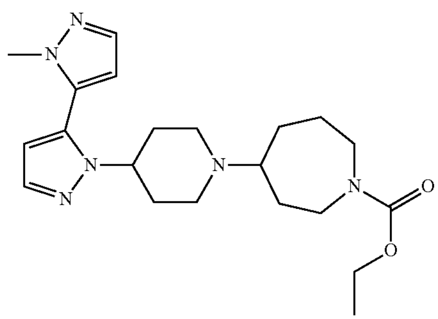 [SMILES: CCOC(=O)N1CCCC(N2CCC(n3nccc3-c3ccnn3C)CC2)CC1] | ethyl 4-{4-[5-(1-methyl-1H-pyrazol-5-yl)-1H-pyrazol-1-yl]piperidin-1-yl}azepane-1-carboxylate | CAS: 720702-41-0 and Intermediate 4 | d | ¹H NMR (400 MHz, MeCN-d3) δ 1.23 (t, J = 6.69 Hz, 3H) 1.70-1.90 (m, 6H) 2.03-2.10 (m, 1H) 2.16-2.32 (m, 8H) 2.75-2.93 (m, 1H) 3.19-3.32 (m, 2H) 3.41-3.56 (s, 2H) 3.73 (s, 3H) 4.08 (m, J = 6.10 Hz, 2H) 6.40 (m, J = 4.80, 1.80 Hz, 2H) 7.55 (d, J = 1.77 Hz, 1H) 7.60 (d, J = 1.00 Hz, 1H) | ES+ 401.4 |

TABLE 2-continued

| Ex. No. | Structure | Name | Intermediate | Synthetic method | $^1$H NMR | LCMS data |
|---|---|---|---|---|---|---|
| 8 | 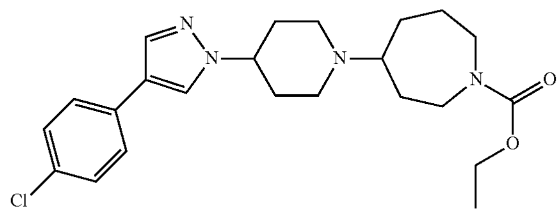 [SMILES: CCOC(=O)N1CCCC(N2CCC(n3cc(-c4ccc(Cl)cc4)cn3)CC2)CC1] | ethyl 4-{4-[4-(4-chlorophenyl)-1H-pyrazol-1-yl]piperidin-1-yl}azepane-1-carboxylate | CAS: 90286-38-8 and Intermediate 3 | a | $^1$H NMR (400 MHz, CD$_2$Cl$_2$) δ 1.24 (t, J = 7.1 Hz, 3H), 1.40-1.70 (m, 4H), 1.82-2.05 (m, 4H), 2.11 (m, 2H), 2.35-2.60 (m, 3H), 2.92 (m, 2H), 3.28 (m, 2H), 3.52 (m, 2H), 4.09 (q, J = 7.1 Hz, 2H), 7.32 (m, 2H), 7.42 (m, 2H), 7.71 +7.72 (2 × s, 2H) | ES+ 431, 433 |
| 9 | 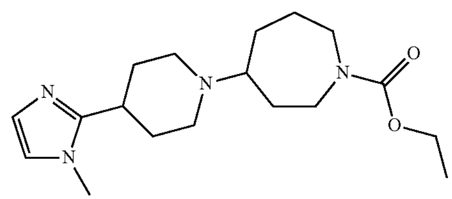 | ethyl 4-[4-(1-methyl-1H-imidazol-2-yl)piperidin-1-yl]azepane-1-carboxylate | CAS: 1084976-68-0 and Intermediate 3 | a | $^1$H NMR (400 MHz, DMSO-d6) δ 1.15 (t, J = 7.3, 3H), 1.32-1.45 (m, 2H), 1.61 (m, 1H), 1.66-1.78 (m, 3H), 2.18-2.31 (m, 2H), 2.33-2.45 (m, 1H), 2.60 (m, 1H), 2.67-2.79 (m, 2H), 3.11-3.23 (m, 3H), 3.41 (m, 2H), 3.47-3.55 (m, 3H), 4.02 (q, J = 7.3, 2H), 6.67 (s, 1H), 6.91 (s, 1H) | ES+ 335.2 |
| 10 | 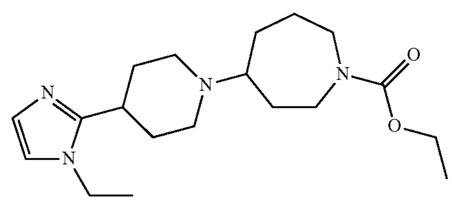 [SMILES: CCOC(=O)N1CCCC(N2CCC(c3nccn3CC)CC2)CC1] | ethyl 4-[4-(1-ethyl-1H-imidazol-2-yl)piperidin-1-yl]azepane-1-carboxylate | CAS: 75-03-6, CAS: 158654-96-7 and Intermediate 3 | b | $^1$H NMR (400 MHz, DMSO-d6) δ 1.00 (t, J = 7.3, 3H), 1.15 (t, J = 6.9, 3H), 1.33-1.45 (m, 2H), 1.57 (m, 1H), 1.65-1.75 (m, 4H), 1.96-2.08 (m, 1H), 2.25-2.33 (m, 2H), 2.35-2.45 (m, 2H), 2.49-2.54 (m, 2H), 2.55-2.67 (m, 1H), 2.71-2.81 (m, 2H), 2.89-3.00 (m, 1H), 3.37-3.49 (m, 2H), 3.87 (q, J = 6.9, 2H), 4.00 (q, J = 7.3, 2H), 6.62-7.01 (br. s, 1H), 6.90-7.01 (br. s, 1H) | ES+ 349.2 |
| 11 | 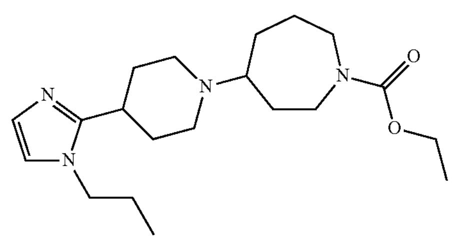 [SMILES: CCCn1ccnc1C1CCN(C2CCCN(C(=O)OCC)CC2)CC1] | ethyl 4-[4-(1-propyl-1H-imidazol-2-yl)piperidin-1-yl]azepane-1-carboxylate | CAS: 106-94-5, CAS: 158654-96-7 and Intermediate 3 | c | $^1$H NMR (400 MHz, DMSO-d6) δ 0.81 (t, J = 7.3, 3H), 0.92 (t, J = 7.1, 3H), 1.10-1.20 (m, 2H), 1.24-1.35 (m, 2H), 1.51-1.58 (m, 2H), 1.59-1.69 (m, 3H), 1.71-1.80 (m, 2H), 2.19-2.31 (m, 2H), 2.34-2.45 (m, 2H), 2.52-2.64 (m, 2H), 2.74 (m, 1H), 3.10-3.22 (m, 2H), 3.33-3.45 (m, 2H), 3.78 (t, J = 7.3, 2H), 3.99 (q, J = 7.1, 2H), 6.70 (s, 1H), 6.96 (s, 1H) | ES+ 363.2 |

TABLE 2-continued

| Ex. No. | Structure | Name | Intermediate | Synthetic method | ¹H NMR | LCMS data |
|---|---|---|---|---|---|---|
| 12 | 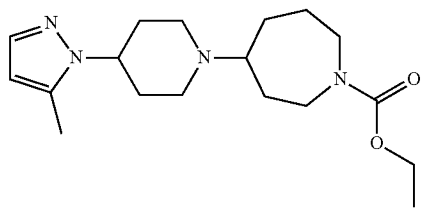 [SMILES: CCOC(=O)N1CCCC(N2CCC(n3nccc3C)CC2)CC1] | ethyl 4-[4-(5-methyl-1H-pyrazol-1-yl)piperidin-1-yl]azepane-1-carboxylate | CAS: 286961-14-6, CAS: 88054-14-2 and Intermediate 3 | h | ¹H NMR (400 MHz, MeOD) δ 1.3 (t, 3H), 1.6 (m, 2H), 1.75 (m, 1H), 1.9-2.1 (m, 5H), 2.2 (m, 2H), 2.34 (s, 3H), 3.65 (b, 3H), 3.1 (b, 2H), 3.4 (m, 2H), 3.6 (m, 2H), 4.1-4.3 (m, 3H), 6.05 (d, 1H), 7.38 (d, 1H) | ES+ 335.2 |
| 13 | 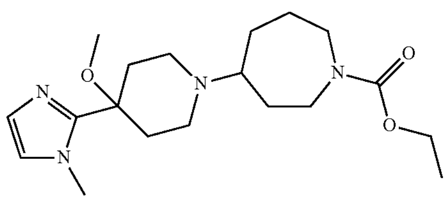 [SMILES: CCOC(=O)N1CCCC(N2CCC(OC)(c3nccn3C)CC2)CC1] | ethyl 4-[4-[4-methoxy-4-(1-methyl-1H-imidazol-2-yl)piperidin-1-yl]azepane-1-carboxylate | Intermediates 2 and 3 | a | ¹H NMR (400 MHz, DMSO-d₆) δ 1.17 (td, J = 7.0, 1.4 Hz, 3H), 1.33-1.46 (m, 2H), 1.54-1.63 (m, 1H), 1.76-1.79 (m, 3H), 1.95-2.05 (m, 4H), 2.39-2.48 (m, 3H), 2.86 (s, 3H), 3.17-3.24 (m, 4H), 3.41-3.48 (m, 2H), 3.71 (s, 3H), 4.03 (qd, J = 7.0, 1.8 Hz, 2H), 6.76 (s, 1H), 7.09 (s, 1H) | ES+ 365.2 |
| 14 | 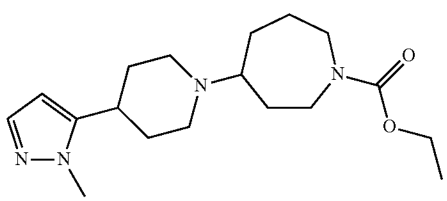 [SMILES: CCOC(=O)N1CCCC(N2CCC(c3ccnn3C)CC2)CC1] | ethyl 4-[4-(1-methyl-1H-pyrazol-5-yl)piperidin-1-yl]azepane-1-carboxylate | CAS: 640270-01-5 and Intermediate 3 | a | ¹H NMR (400 MHz, DMSO-d6) δ 1.17 (t, J = 7.4, 3H), 1.35-1.51 (m, 5H), 1.72-1.83 (m, 3H), 2.22-2.35 (m, 2H), 2.38-2.51 (m, 4H), 2.68-2.82 (m, 3H), 3.14-3.25 (m, 2H), 3.31-3.47 (m, 6H), 3.98 (q, J = 7.4, 2H), 5.86-6.03 (br. s, 1H), 7.08-7.25 (br. s, 1H) | ES+ 335.2 |
| 15 | 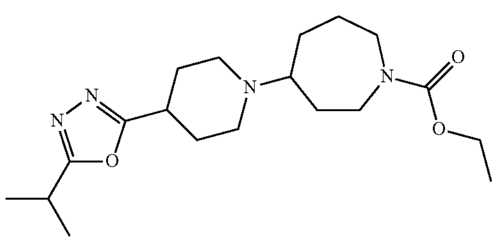 [SMILES: CCOC(=O)N1CCCC(N2CCC(c3nnc(C(C)C)o3)CC2)CC1] | ethyl 4-(4-(5-isopropyl-1,3,4-oxadiazol-2-yl)piperidin-1-yl)azepane-1-carboxylate | CAS: 3619-17-8 and Intermediate 1 | e | ¹H NMR (400 MHz, CD₃OD) δ 1.29 (td, J = 7.1, 3.3 Hz, 3H), 1.39 (d, J = 7.0 Hz, 6H), 2.20-1.46 (m, 10H), 2.73-2.47 (m, 3H), 3.06-2.93 (m, 3H), 3.21 (dt, J = 13.9, 7.0 Hz, 1H), 3.44-3.35 (m, 2H), 3.59 (dt, J = 10.1, 4.9 Hz, 2H), 4.15 (qd, J = 7.1, 3.0 Hz, 2H) | ES+ 365.2 |

TABLE 2-continued

| Ex. No. | Structure | Name | Intermediate | Synthetic method | ¹H NMR | LCMS data |
|---|---|---|---|---|---|---|
| 16 | 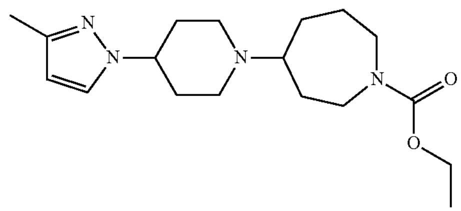 [SMILES: CCOC(=O)N1CCCC(N2CCC(n3ccc(C)n3)CC2)CC1] | ethyl 4-{4-(3-methyl-1H-pyrazol-1-yl)piperidin-1-yl]azepane-1-carboxylate | CAS: 286961-14-6, CAS : 88054-14-2 and Intermediate 3 | h | ¹H NMR (400 MHz, MeOD) δ 1.3 (t, 3H), 1.75 (m, 1H), 1.9-2.17 (m, 7H), 2.24 (s, 3H), 2.5-2.7 (m, 3H), 3 (b, 2H), 3.4 (m, 2H), 3.6 (m 2H), 4-4.2 (m, 3H), 6.06 (d, 1H), 7.54 (d, 1H) | ES+ 335.2 |
| 17 | 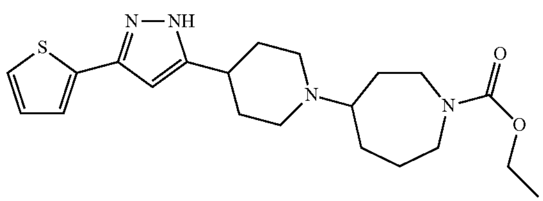 [SMILES: CCOC(=O)N1CCCC(N2CCC(c3cc(-c4cccs4)n[nH]3)CC2)CC1] | ethyl 4-{4-[3-(thiophen-2-yl)-1H-pyrazol-5-yl]piperidin-1-yl}azepane-1-carboxylate | CAS: 321848-28-6 and Intermediate 3 | a | ¹H NMR (400 MHz, DMSO-d6) δ 1.15 (t, J = 7.3, 3H), 1.32-1.44 9m, 2H), 1.48-1.61, (m, 3H), 1.73-1.79 (m, 2H), 1.81-1.88 (m, 6H), 2.19-2.31 (m, 2H), 2.39-2.51 (m, 2H), 2.70-2.80 (m, 2H), 3.99 (q, J = 7.3, 2H), 6.30 (s, 1H), 6.92-7.04 (m, 1H), 7.27 (m, 1H), 7.36 (m, 1H) | ES+ 403.2 |
| 18 | 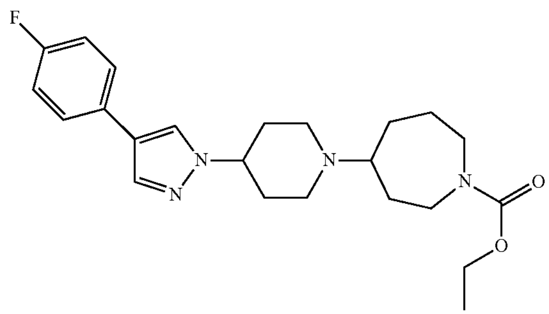 [SMILES: CCOC(=O)N1CCCC(N2CCC(n3cc(-c4ccc(F)cc4)cn3)CC2)CC1] | ethyl 4-{4-[4-(4-fluorophenyl)-1H-pyrazol-1-yl]azepane-1-carboxylate | CAS: 1205747-45-0 and Intermediate 3 | | ¹H NMR (400 MHz, CDCl₃) δ 1.24-1.34 (m, 3H), 1.43-1.58 (m, 2H), 1.63-1.74 (m, 1H), 1.85-2.09 (m, 5H), 2.16-2.28 (m, 2H), 2.37-2.65 (m, 3H), 2.88-3.03 (m, 2H), 3.31 (br. s, 2H), 3.49-3.72 (m, 2H), 4.06-4.24 (m, 3H), 6.99-7.12 (m, 2H), 7.39-7.48 (m, 2H), 7.65 (s, 1H), 7.73 (s, 1H) | ES+ 415.7 |
| 19 | 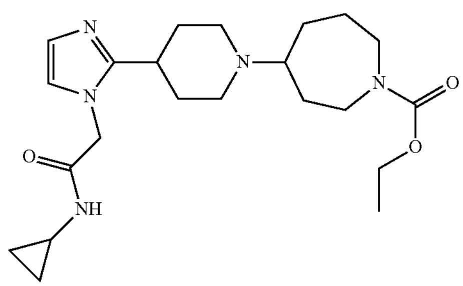 [SMILES: CCOC(=O)N1CCCC(N2CCC(c3nccn3CC(=O)NC3CC3)CC2)CC1] | ethyl 4-(4-{1-[(cyclopropylcarbamoyl)methyl]-1H-imidazol-2-yl}piperidin-1-yl)azepane-1-carboxylate | CAS: 19047-31-5 and Intermediate 3 | c | ¹H NMR (400 MHz, MeCN-d3) δ 0.38-0.50 (m, 2H) 0.60-0.72 (m, 2H) 1.24 (t, J = 6.32 Hz, 3H) 1.36-1.92 (m, 10H) 2.25-2.38 (m, 2H) 2.42-2.57 (m, 2H) 2.66 (td, J = 7.20, 3.54 Hz, 1H) 2.76-2.90 (m, 2H) 3.28 (m, J = 14.00, 9.50, 4.00 Hz, 2H) 3.44-3.60 (m, 2H) 4.09 (q, J = 6.57 Hz, 2H) 4.48 (s, 2H) 6.61 (br. s., 1H) 6.84 (d, J = 8.84 Hz, 2H) | ES+ 418.4, ES− 416.4 |

TABLE 2-continued

| Ex. No. | Structure | Name | Intermediate | Synthetic method | ¹H NMR | LCMS data |
|---|---|---|---|---|---|---|
| 20 | 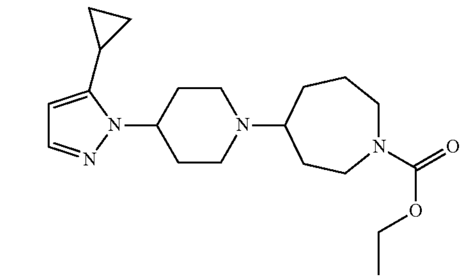 [SMILES: CCOC(=O)N1CCCC(N2CCC(n3nccc3C3CC3)CC2)CC1] | ethyl 4-{4-(5-cyclopropyl-1H-pyrazol-1-yl)piperidin-1-yl]azepane-1-carboxylate | CAS: 411235-57-9 and Intermediate 4 | d | ¹H NMR (400 MHz, MeCN-d3) δ 0.63 (dd, J = 5.05, 1.77 Hz, 2H) 0.82-1.03 (m, 2H) 1.24 (t, J = 6.06 Hz, 3H) 1.41-1.75 (m, 2H) 1.77-1.92 (m, 5H) 2.08 (d, J = 11.87 Hz, 2H) 2.13-2.15 (m, 2H) 2.42 (d, J = 11.37 Hz, 2H) 2.49-2.63 (m, 1H) 2.91 (br. s., 2H) 3.31 (dd, J = 9.47, 4.17 Hz, 2H) 3.46-3.60 (m, 2H) 4.10 (d, J = 5.31 Hz, 2H) 4.32 (s, 1H) 5.84 (d, J = 1.26 Hz, 1H) 7.28 (d, J = 1.26 Hz, 1H) | ES+ 361.4 |
| 21 | 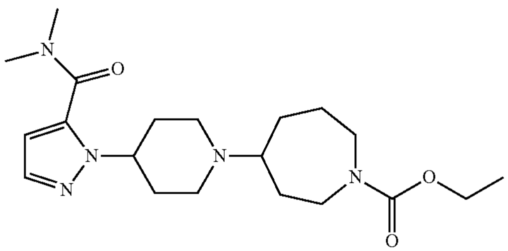 [SMILES: CCOC(=O)N1CCCC(N2CCC(n3nccc3C(=O)N(C)C)CC2)CC1] | ethyl 4-{4-[5-(dimethylcarbamoyl)-1H-pyrazol-1-yl]piperidin-1-yl}azepane-1-carboxylate | CAS: 124-40-3 and Intermediate 4 | f | ¹H NMR (400 MHz, MeOD) δ 1.3 (t, 3H), 1.4-1.6 (m, 2H), 1.7 (m, 1H), 1.9-2.05 (m, 5H), 2.2 (m, 2H), 2.48 (m, 2H), 2.6 (t, 1H), 2.95 (b, 2H), 3.09 (s, 3H), 3.12 (s, 3H), 3.35 (m, 2H), 3.6 (m, 2H), 4.12 (q, 2H), 4.3 (m, 1H), 6.45 (d, 1H), 7.52 (d, 1H) | ES+ 392.2 |
| 22 | 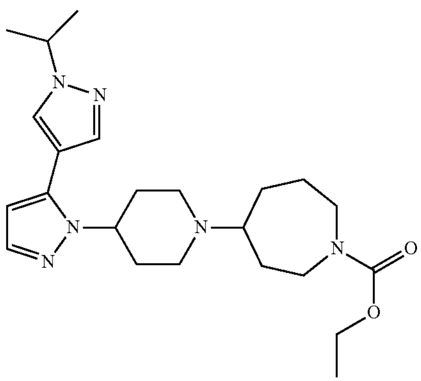 [SMILES: CCOC(=O)N1CCCC(N2CCC(n3nccc3-c3cnn(C(C)C)c3)CC2)CC1] | ethyl 4-(4-{5-[1-(propan-2-yl)-1H-pyrazol-4-yl]-1H-pyrazol-1-yl}piperidin-1-yl)azepane-1-carboxylate | CAS: 1201643-90-4 and Intermediate 4 | d | ¹H NMR (400 MHz, MeCN-d3) δ 1.24 (t, J = 6.57 Hz, 3H) 1.37-1.73 (m, 8H) 1.78-1.92 (m, 6H) 2.12 (m, J = 4.30 Hz, 2H) 2.37 (d, J = 11.62 Hz, 2H) 2.48-2.62 (m, 1H) 2.79-2.96 (m, 2H) 3.17-3.37 (m, 2H) 3.51 (m, J = 5.60 Hz, 2H) 4.09 (q, J = 6.57 Hz, 2H) 4.13-4.27 (m, 1H) 4.48-4.65 (m, 1H) 6.25 (d, J = 1.77 Hz, 1H) 7.45 (d, J = 1.26 Hz, 1H) 7.59 (s, 1H) 7.74 (s, 1H) | ES+ 429.4 |

TABLE 2-continued

| Ex. No. | Structure | Name | Intermediate | Synthetic method | ¹H NMR | LCMS data |
|---|---|---|---|---|---|---|
| 23 | 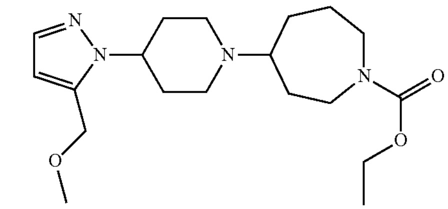 [SMILES: CCOC(=O)N1CCCC(N2CCC(n3nccc3COC)CC2)CC1] | ethyl 4-{4-[5-(methoxymethyl)-1H-pyrazol-1-yl]piperidin-1-yl}azepane-1-carboxylate | Intermediates 7 and 3 | a | ¹H NMR (400 MHz, MeCN-d3) δ 1.18-1.29 (m, 3H) 1.40-1.92 (m, 8H) 2.01-2.22 (m, 3H) 2.27-2.45 (m, 2H) 2.49-2.62 (m, 1H) 2.90 (br. s., 2H) 3.20-3.38 (m, 5H) 3.42-3.62 (m, 2H) 4.01-4.19 (m, 3H) 4.47 (s, 2H) 6.20 (d, J = 1.52 Hz, 1H) 7.39 (d, J = 1.00 Hz, 1H) | ES+ 365.4 |
| 24 | 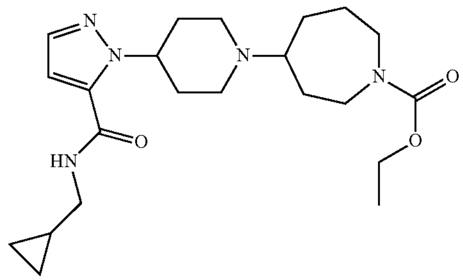 [SMILES: CCOC(=O)N1CCCC(N2CCC(n3nccc3C(=O)NCC3CC3)CC2)CC1] | ethyl 4-(4-{5-[(cyclopropylmethyl)carbamoyl]-1H-pyrazol-1-yl}piperidin-1-yl)azepane-1-carboxylate | CAS: 2516-47-4 and Intermediate 4 | f | ¹H NMR (400 MHz, MeCN-d3) δ 0.02 (d, J = 5.05 Hz, 2H) 0.26 (d, J = 6.57 Hz, 2H) 0.99 (s, 3H) 1.65 (d, J = 11.37 Hz, 5H) 1.76-1.87 (m, 3H) 1.90 (s, 10H) 2.02-2.21 (m, 2H) 2.94 (t, J = 6.32 Hz, 2H) 2.99-3.11 (m, 2H) 3.72-3.94 (m, 2H) 6.38 (d, J = 1.77 Hz, 1H) 7.21 (d, J = 1.77 Hz, 1H) | ES+ 418.8, ES− 416.8 |
| 25 | 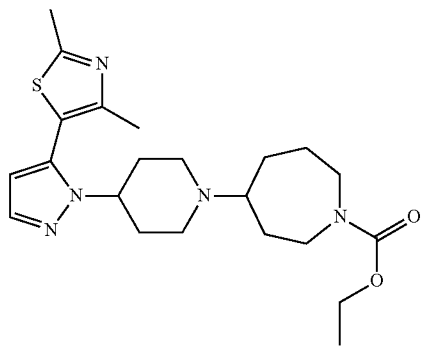 [SMILES: CCOC(=O)N1CCCC(N2CCC(n3nccc3-c3sc(C)nc3C)CC2)CC1] | ethyl 4-{4-[5-(dimethyl-1,3-thiazol-5-yl)-1H-pyrazol-1-yl]piperidin-1-yl}azepane-1-carboxylate | CAS: 936361-37-4 and Intermediate 4 | d | ¹H NMR (400 MHz, MeCN-d3) δ 1.23 (t, J = 6.95 Hz, 3H) 1.37-1.91 (m, 7H) 2.11 (dd, J = 11.49, 5.68 Hz, 3H) 2.19-2.34 (m, 5H) 2.41-2.57 (m, 1H) 2.68 (s, 3H) 2.79-2.95 (m, 2H) 3.28 (m, J = 9.50, 4.20 Hz, 2H) 3.42-3.60 (m, 2H) 3.85-4.01 (m, 1H) 4.08 (q, J = 6.80 Hz, 2H) 6.33 (d, J = 1.77 Hz, 1H) 7.55 (d, J = 1.52 Hz, 1H) | ES+ 432.4 |

TABLE 2-continued

| Ex. No. | Structure | Name | Intermediate | Synthetic method | ¹H NMR | LCMS data |
|---|---|---|---|---|---|---|
| 26 | 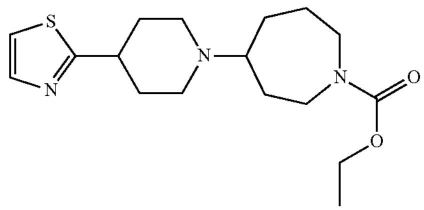 [SMILES: CCOC(=O)N1CCCC(N2CCC(c3nccs3)CC2)CC1] | ethyl 4-[4-(1,3-thiazol-2-yl)piperidin-1-yl]azepane-1-carboxylate | CAS: 788822-03-7 and Intermediate 3 | a | ¹H NMR (400 MHz, MeCN-d3) δ 1.24 (t, J = 6.95 Hz, 3H) 1.41-1.58 (m, 2H) 1.59-1.79 (m, 3H) 1.81-1.94 (m, 3H) 2.07 (m, J = 12.60 Hz, 2H) 2.38 (q, J = 11.45 Hz, 2H) 2.51 (m, J = 8.80, 8.80 Hz, 1H) 2.87 (m, J = 9.50, 9.50 Hz, 2H) 2.93-3.10 (m, 1H) 3.28 (m, J = 14.00, 9.50, 4.00 Hz, 2H) 3.43-3.59 (m, 2H) 4.09 (q, J = 6.99 Hz, 2H) 7.36 (d, J = 3.28 Hz, 1H) 7.68 (d, J = 3.03 Hz, 1H) | ES+ 338.3 |
| 27 | 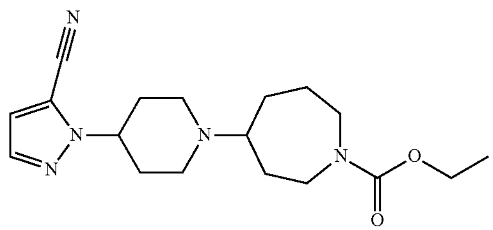 [SMILES: CCOC(=O)N1CCCC(N2CCC(n3nccc3C#N)CC2)CC1] | ethyl 4-[4-(5-cyano-1H-pyrazol-1-yl)piperidin-1-yl]azepane-1-carboxylate | CAS: 557-21-1 and Intermediate 4 | l | ¹H NMR (400 MHz, MeOD) δ 1.3 (t, 3H), 1.6 (m, 2H), 1.75 (m, 1H), 1.9-2.1 (m, 5H), 2.25 (m, 2H), 2.5-2.7 (m, 3H), 3.0 (b, 2H), 3.35 (m, 2H), 3.6 (m, 2H), 4.15 (q, 2H), 4.45 (m, 1H), 6.95 (d, 1H), 7.65 (d, 1H) | ES+ 346.1 |
| 28 | 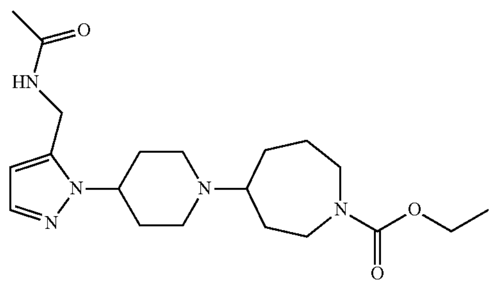 [SMILES: CCOC(=O)N1CCCC(N2CCC(n3nccc3CNC(C)=O)CC2)CC1] | ethyl 4-{4-[5-(acetamidomethyl)-1H-pyrazol-1-yl]piperidin-1-yl}azepane-1-carboxylate | Example 27 and CAS: 75-36-5 | m | ¹H NMR (400 MHz, MeOD) δ 1.3 (m, 4H), 1.4-1.6 (m, 2H), 1.7 (m, 1H), 1.9 (m, 2H), 2.0 (s, 3H), 2.1 (m, 2H), 2.2 (m, 2H), 2.45-2.65 (m, 3H), 2.95 (b, 2H), 3.35 (m, 3H), 3.6 (m, 2H), 4.15 (q, 2H), 4.25 (m, 1H), 4.47 (d, 2H), 6.22 (d, 1H), 7.41 (d, 1H) | ES+ 392.2 |
| 29 | 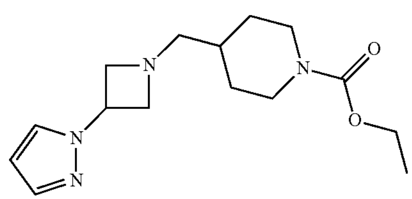 [SMILES: CCOC(=O)N1CCC(CN2CC(n3cccn3)C2)CC1] | ethyl 4-{[3-(1H-pyrazol-1-yl)azetidin-1-yl]methyl}piperidine-1-carboxylate | CAS: 288-13-1, CAS: 254454-54-1, CAS: 137076-22-3 and CAS: 541-41-3 | i | ¹H NMR (400 MHz, MeCN-d3) δ 0.93-1.13 (m, 2H) 1.23 (t, J = 7.07 Hz, 3H) 1.43-1.61 (m, 1H) 1.67-1.78 (m, 2H) 2.41 (m, J = 7.10 Hz, 2H) 2.68-2.84 (m, 1H) 3.32-3.45 (m, 2H) 3.72 (m, J = 7.50, 7.50 Hz, 2H) 3.95-4.14 (m, 4H) 4.85-5.02 (m, 1H) 6.21-6.33 (m, 1H) 7.49 (d, J = 1.00 Hz, 1H) 7.67 (d, J = 2.02 Hz, 1H) | ES+ 293.3 |

TABLE 2-continued

| Ex. No. | Structure | Name | Intermediate | Synthetic method | ¹H NMR | LCMS data |
|---|---|---|---|---|---|---|
| 30 | 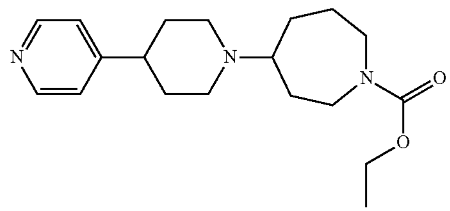 [SMILES: CCOC(=O)N1CCCC(N2CCC(c3ccncc3)CC2)CC1] | ethyl 4-[4-(pyridin-4-yl)piperidin-1-yl]azepane-1-carboxylate | CAS: 581-45-3 and Intermediate 3 | a | ¹H NMR (400 MHz, CD₂Cl₂) δ 1.24 (t, J = 6.3 Hz, 3H), 1.54 (m, 3H), 1.67 (m, 3H), 1.85 (m, 5H), 2.3-2.5 (m, 3H), 2.87 (m, 2H), 3.26 (m, 2H), 3.53 (m, 2H), 4.09 (q, J = 6.3 Hz, 2H), 7.15 (brs, 2H), 8.46 (brs, 2H) | ES+ 332 |
| 31 | 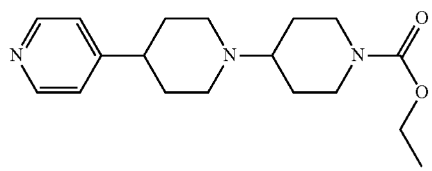 | ethyl 4-[4-(pyridin-4-yl)piperidin-1-yl]piperidine-1-carboxylate | CAS: 581-45-3 and CAS: 29976-53-2 | a | ¹H NMR (400 MHz, CDCl₃) δ 1.23 (t, J = 7.1 Hz, 3H), 1.42-1.93 (m, 8H), 2.26-2.54 (m, 4H), 2.73 (m, 2H), 3.01 (brs, 2H), 4.08 (q, J = 7.1 Hz, 2H), 4.16 (brs, 2H), 7.15 (d, J = 5.5 Hz, 2H), 8.46 (d, J = 5.5 Hz, 2H) | ES+ 318 |
| 32 | 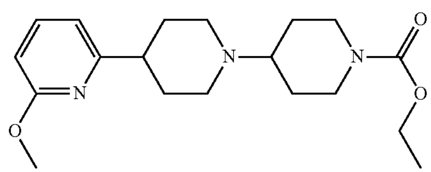 [SMILES: CCOC(=O)N1CCC(N2CCC(c3cccc(OC)n3)CC2)CC1] | ethyl 4-[4-(6-methoxypyridin-2-yl)piperidin-1-yl]piperidine-1-carboxylate | CAS: 40473-07-2 and CAS: 29976-53-2 | g | ¹H NMR (400 MHz, CD₂Cl₂) δ 1.24 (t, J = 7.2 Hz, 3H), 1.41-1.96 (m, 8H), 2.31-2.64 (m, 4H), 2.75 (m, 2H), 3.03 (m, 2H), 3.89 (s, 3H), 4.08 (q, J = 7.2 Hz, 2H), 4.17 (m, 2H), 6.53 (d, J = 8.3 Hz, 1H), 6.73 (d, J = 7.1 Hz, 1H), 7.49 (m, 1H) | ES+ 348 |
| 33 | 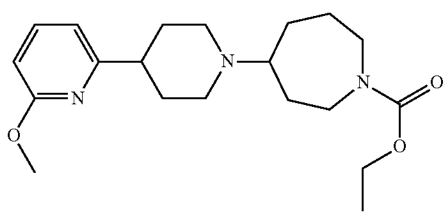 [SMILES: CCOC(=O)N1CCCC(N2CCC(c3cccc(OC)n3)CC2)CC1] | ethyl 4-[4-(6-methoxypyridin-2-yl)piperidin-1-yl]azepane-1-carboxylate | CAS: 40473-07-2 and Intermediate 3 | g | ¹H NMR (400 MHz, CD₂Cl₂) δ 1.24 (t, J = 6.8 Hz, 3H), 1.40-1.72 (m, 6H), 1.75-2.05 (m, 5H), 2.32-2.60 (m, 3H), 2.91 (m, 2H), 3.27 (m, 2H), 3.54 (m, 2H), 3.89 (s, 3H), 4.09 (q, J = 6.8 Hz, 2H), 6.53 (d, J = 8.1 Hz, 1H), 6.73 (d, J = 7.3 Hz, 1H), 7.48 (t, J = 7.7 Hz, 1H) | ES+ 362 |
| 34 | 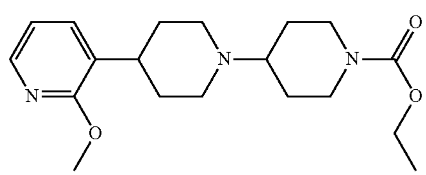 [SMILES: CCOC(=O)N1CCC(N2CCC(c3cccnc3OC)CC2)CC1] | ethyl 4-[4-(2-methoxypyridin-3-yl)piperidin-1-yl]piperidine-1-carboxylate | CAS: 13472-59-8 and CAS: 29976-53-2 | g | ¹H NMR (400 MHz, CD₂Cl₂) δ 1.23 (t, J = 7.1 Hz, 3H), 1.45 (dd, J = 12, 4.2 Hz, 2H), 1.66 (m, 2H), 1.82 (m, 4H), 2.34 (t, J = 11.2 Hz, 2H), 2.48 (m, 1H), 2.76 (m, 3H), 3.00 (d, J = 11.1 Hz, 2H), 3.91 (s, 3H), 4.08 (q, J = 7.1 Hz, 2H), 4.16 (m, 2H), 6.84 (dd, J = 7.2, 4.9 Hz, 1H), 7.45 (dd, J = 7.2, 1.5 Hz, 1H), 7.97 (dd, J = 4.9, 1.5 Hz, 1H) | ES+ 348 |

TABLE 2-continued

| Ex. No. | Structure | Name | Intermediate | Synthetic method | $^1$H NMR | LCMS data |
|---|---|---|---|---|---|---|
| 35 | 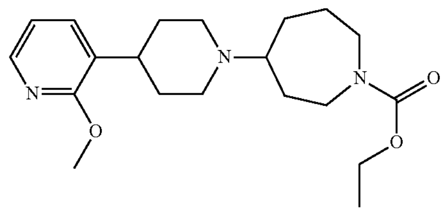 | ethyl 4-[4-(2-methoxypyridin-3-yl)piperidin-1-yl]azepane-1-carboxylate | CAS: 13472-59-8 and Intermediate 3 | g | $^1$H NMR (400 MHz, CD$_2$Cl$_2$) δ 1.24 (t, J = 6.8 Hz, 3H), 1.41-1.71 (m, 6H), 1.77-2.01 (m, 4H), 2.33-2.55 (m, 3H), 2.71-2.93 (m, 3H), 3.26 (m, 2H), 3.54 (m, 2H), 3.91 (s, 3H), 4.09 (q, J = 6.8 Hz, 2H), 6.83 (dd, J = 7.2, 4.9 Hz, 1H), 7.45 (d, J = 7.2 Hz, 1H), 7.96 (dd, J = 4.9, 1.6 Hz, 1H) | ES+ 362 |
| 36 | 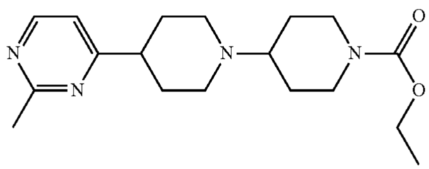 | ethyl 4-[4-(2-methylpyrimidin-4-yl)piperidin-1-yl]piperidine-1-carboxylate | CAS: 949100-33-8 and CAS: 29976-53-2 | a | $^1$H NMR (400 MHz, CD$_2$Cl$_2$) δ 1.23 (m, 3H), 1.45 (qd, J = 12.1, 4.3 Hz, 2H), 1.71-1.84 (m, 4H), 1.87-1.95 (m, 2H), 2.33 (t, J = 11 Hz, 2H), 2.44-2.65 (m, 5H), 2.75 (m, 2H), 3.02 (d, J = 11 Hz, 2H), 4.13-4.20 (m, 4H), 6.98 (d, J = 5.2 Hz, 1H), 8.48 (d, J = 5.2 Hz, 1H) | ES+ 333 |
| 37 | 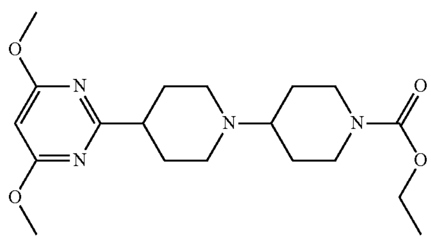 [SMILES: CCOC(=O)N1CCC(N2CCC(c3nc(OC)cc(OC)n3)CC2)CC1] | ethyl 4-[4-(4,6-dimethoxypyrimidin-2-yl)piperidin-1-yl]piperidine-1-carboxylate | CAS: 849924-99-8 and CAS: 29976-53-2 | a | $^1$H NMR (400 MHz, CD$_2$Cl$_2$) δ 1.23 (t, J = 7.1 Hz, 3H), 1.44 (dd, J = 12, 4.2 Hz, 2H), 1.76-1.92 (m, 4H), 1.94-2.15 (m, 2H), 2.32 (m, 2H), 2.46 (m, 1H), 2.63 (m, 1H), 2.74 (m, 2H), 2.97 (m, 2H), 3.90 (s, 6H), 4.08 (q, J = 7.1 Hz, 2H), 4.16 (m, 2H), 5.84 (s, 1H) | ES+ 379 |
| 38 | 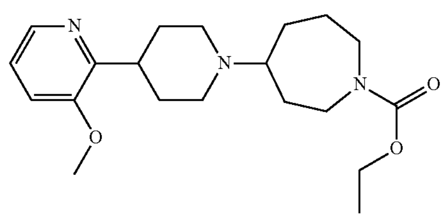 | ethyl 4-[4-(3-methoxypyridin-2-yl)piperidin-1-yl]azepane-1-carboxylate | CAS: 24100-18-3 and Intermediate 3 | g | $^1$H NMR (400 MHz, DMSO-d6) δ 1.68-1.92 (m, 3H) 2.01-2.47 (m, 8H) 2.62-2.75 (m, 4H) 2.80-2.99 (m, 2H) 3.00-3.14 (m, 1H) 3.30-3.50 (m, 2H) 3.53-3.68 (m, 1H) 3.85 (ddd, J = 13.96, 9.41, 4.17 Hz, 2H) 4.39 (s, 3H) 4.58-4.73 (m, 2H) 7.62-7.75 (m, 1H) 7.82 (d, J = 8.34 Hz, 1H) 8.65 (d, J = 4.55 Hz, 1H) | ES+ 362.4 |

TABLE 2-continued

| Ex. No. | Structure | Name | Intermediate | Synthetic method | ¹H NMR | LCMS data |
|---|---|---|---|---|---|---|
| 39 | 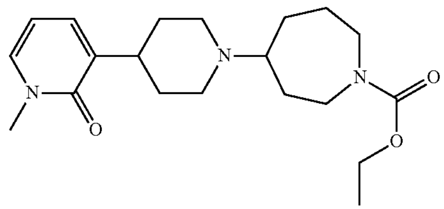 [SMILES: CCOC(=O)N1CCCC(N2CCC(c3cccn(C)c3=O)CC2)CC1] | ethyl 4-[4-(1-methyl-2-oxo-1,2-dihydropyridin-3-yl)piperidin-1-yl]azepane-1-carboxylate | Intermediates 5 and 3 | g | ¹H NMR (400 MHz, MeCN-d3) δ 1.14-1.30 (m, 3H) 1.38-1.58 (m, 2H) 1.71-1.91 (m, 4H) 1.98-2.03 (m, 4H) 2.27-2.90 (m, 3H) 3.30 (s, 3H) 3.46 (s, 4H) 4.08 (d, J = 6.82 Hz, 2H) 6.14 (s, 1H) 7.15-7.23 (m, 1H) 7.28-7.37 (m, 1H) | ES+ 362.4 |
| 40 | 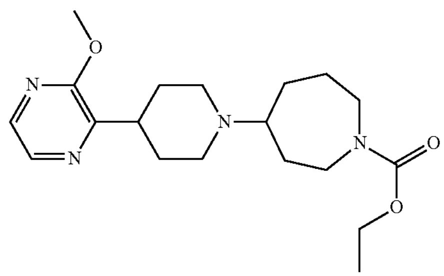 [SMILES: CCOC(=O)N1CCCC(N2CCC(c3nccnc3OC)CC2)CC1] | ethyl 4-[4-(3-methoxypyrazin-2-yl)piperidin-1-yl]azepane-1-carboxylate | CAS: 1209905-41-8 and Intermediate 3 | g | ¹H NMR (400 MHz, MeCN-d3) δ 1.24 (t, J = 6.19 Hz, 3H) 1.37-1.92 (m, 10H) 2.37 (m, J = 10.60 Hz, 2H) 2.46-2.57 (m, 1H) 2.81-3.02 (m, 3H) 3.29 (m, J = 13.80, 9.40, 4.00 Hz, 2H) 3.44-3.60 (m, 2H) 3.95 (s, 3H) 4.09 (q, J = 6.74 Hz, 2H) 7.95 (d, J = 2.78 Hz, 1H) 8.05 (d, J = 2.78 Hz, 1H) | ES+ 363.0 |
| 41 | 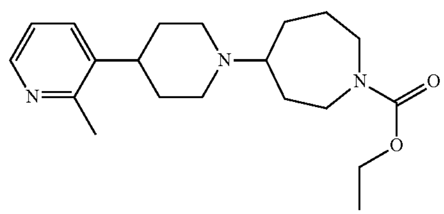 [SMILES: CCOC(=O)N1CCCC(N2CCC(c3cccnc3C)CC2)CC1] | ethyl 4-[4-(2-methylpyridin-3-yl)piperidin-1-yl]azepane-1-carboxylate | CAS: 38749-79-0 and Intermediate 3 | g | ¹H NMR (400 MHz, MeCN-d3) δ 1.24 (t, J = 6.19 Hz, 3H) 1.40-1.80 (m, 7H) 1.88 (d, J = 10.86 Hz, 3H) 2.30-2.60 (m, 6H) 2.64-2.78 (m, 1H) 2.90 (m, J = 9.20, 9.20 Hz, 2H) 3.20-3.35 (m, 2H) 3.52 (m, J = 9.20, 9.20, 4.70 Hz, 2H) 4.10 (q, J = 6.65 Hz, 2H) 7.14 (dd, J = 7.83, 4.80 Hz, 1H) 7.58 (d, J = 6.82 Hz, 1H) 8.28 (dd, J = 4.67, 1.39 Hz, 1H) | ES+ 346.0 |
| 42 | 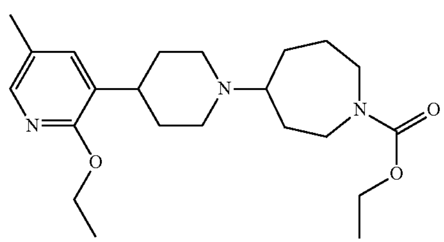 [SMILES: CCOC(=O)N1CCCC(N2CCC(c3cc(C)cnc3OCC)CC2)CC1] | ethyl 4-[4-(2-ethoxy-5-methylpyridin-3-yl)piperidin-1-yl]azepane-1-carboxylate | CAS: 760207-82-7 and Intermediate 3 | g | ¹H NMR (400 MHz, MeCN-d3) δ 1.24 (t, J = 6.19 Hz, 3H) 1.34 (t, J = 6.95 Hz, 3H) 1.40-1.92 (m, 10H) 2.22 (s, 3H) 2.27-2.56 (m, 3H) 2.65-2.77 (m, 1H) 2.88 (m, J = 9.10, 9.10 Hz, 2H) 3.22-3.38 (m, 2H) 3.43-3.62 (m, 2H) 4.09 (q, J = 6.65 Hz, 2H) 4.33 (q, J = 7.07 Hz, 2H) 7.36 (d, J = 1.52 Hz, 1H) 7.77 (s, 1H) | ES+ 390.0 |

TABLE 2-continued

| Ex. No. | Structure | Name | Intermediate | Synthetic method | $^1$H NMR | LCMS data |
|---|---|---|---|---|---|---|
| 43 | 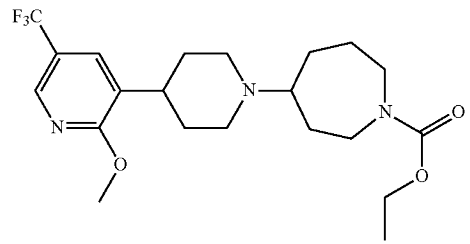 [SMILES: CCOC(=O)N1CCCC(N2CCC(c3cc(C(F)(F)F)cnc3OC)CC2)CC1] | ethyl 4-{4-[2-methoxy-5-(trifluoromethyl)pyridin-3-yl]piperidin-1-yl}azepane-1-carboxylate | CAS: 124432-63-9 and Intermediate 3 | g | $^1$H NMR (400 MHz, MeCN-d3) δ 1.24 (t, J = 6.44 Hz, 3H) 1.38-1.93 (m, 10H) 2.37 (q, J = 10.95 Hz, 2H) 2.47-2.57 (m, 1H) 2.70-2.83 (m, 1H) 2.86-2.96 (m, 2H) 3.19-3.37 (m, 2H) 3.52 (m, J = 9.20, 9.20, 4.50 Hz, 2H) 4.00 (s, 3H) 4.09 (q, J = 6.82 Hz, 2H) 7.75 (s, 1H) 8.36 (s, 1H) | ES+ 430.4 |
| 44 | 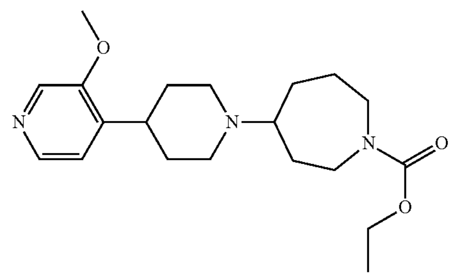 [SMILES: CCOC(=O)N1CCCC(N2CCC(c3ccncc3OC)CC2)CC1] | ethyl 4-[4-(3-methoxypyridin-4-yl)piperidin-1-yl]azepane-1-carboxylate | CAS: 109911-38-8 and Intermediate 3 | g | $^1$H NMR (400 MHz, MeCN-d3) δ 1.24 (t, J = 6.32 Hz, 3H) 1.38-1.93 (m, 10H) 2.37 (m, J = 10.90, 10.90, 10.90 Hz, 2H) 2.46-2.59 (m, 1H) 2.72-2.98 (m, 3H) 3.14-3.35 (m, 2H) 3.43-3.60 (m, 2H) 3.92 (s, 3H) 4.09 (q, J = 6.82 Hz, 2H) 7.18 (d, J = 4.80 Hz, 1H) 8.16 (d, J = 4.80 Hz, 1H) 8.24 (s,1H) | ES+ 362.3 |
| 45 | 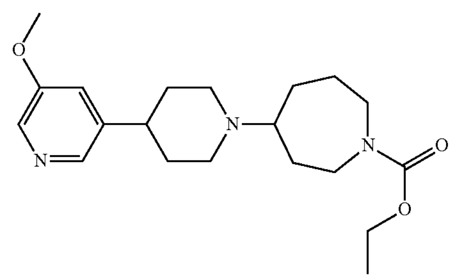 [SMILES: CCOC(=O)N1CCCC(N2CCC(c3cncc(OC)c3)CC2)CC1] | ethyl 4-[4-(5-methoxypyridin-3-yl)piperidin-1-yl]azepane-1-carboxylate | CAS: 50720-12-2 and Intermediate 3 | g | $^1$H NMR (400 MHz, MeCN-d3) δ 1.24 (t, J = 6.44 Hz, 3H) 1.40-1.93 (m, 8H) 2.11-2.19 (m, 4H) 2.24-2.43 (m, 2H) 2.46-2.61 (m, 2H) 2.80-2.98 (m, 2H) 3.20-3.37 (m, 2H) 3.86 (s, 3H) 4.09 (q, J = 7.10 Hz, 2H) 7.17 (s, 1H) 8.03-8.17 (m, 2H) | ES+ 362.3 |
| 46 | 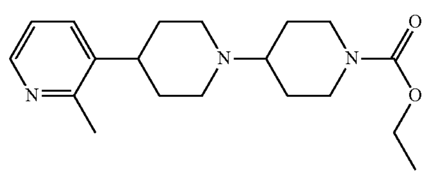 [SMILES: CCOC(=O)N1CCC(N2CCC(c3cccnc3C)CC2)CC1] | ethyl 4-[4-(2-methylpyridin-3-yl)piperidin-1-yl]piperidine-1-carboxylate | CAS: 38749-79-0 and CAS: 29976-53-2 | g | $^1$H NMR (400 MHz, MeCN-d3) δ 1.24 (t, J = 7.07 Hz, 3H) 1.34-1.50 (m, 2H) 1.52-1.70 (m, 2H) 1.78 (m, J = 6.80 Hz, 4H) 2.36 (s, 2H) 2.43-2.59 (m, 4H) 2.63-2.88 (m, 2H) 2.95-3.08 (m, 2H) 3.96-4.23 (m, 4H) 7.07-7.23 (m, 1H) 7.49-7.65 (m, 1H) 8.22-8.34 (m, 1H) | ES+ 332.4 |

TABLE 2-continued

| Ex. No. | Structure | Name | Intermediate | Synthetic method | ¹H NMR | LCMS data |
|---|---|---|---|---|---|---|
| 47 | 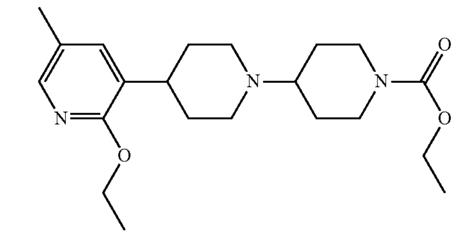 [SMILES: CCOC(=O)N1CCC(N2CCC(c3cc(C)cnc3OCC)CC2)CC1] | ethyl 4-[4-(2-ethoxy-5-methylpyridin-3-yl)piperidin-1-yl]piperidine-1-carboxylate | CAS: 760207-82-7 and CAS: 29976-53-2 | g | ¹H NMR (400 MHz, MeCN-d3) δ 1.24 (t, J = 7.07 Hz, 3H) 1.29-1.50 (m, 5H) 1.59 (m, J = 12.30, 3.40 Hz, 2H) 1.73-1.85 (m, 4H) 2.26-2.38 (m, 2H) 2.42-2.56 (m, 1H) 2.68-2.89 (m, 3H) 3.00 (d, J = 11.37 Hz, 2H) 3.96-4.16 (m, 4H) 4.33 (q, J = 6.91 Hz, 2H) 7.38 (s, 1H) 7.78 (s, 1H) | ES+ 376.4 |
| 48 | 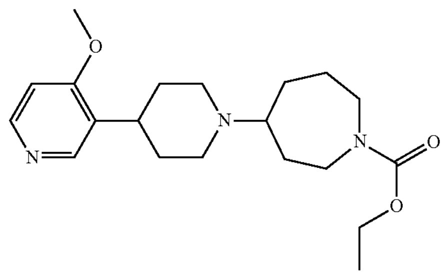 [SMILES: CCOC(=O)N1CCCC(N2CCC(c3cnccc3OC)CC2)CC1] | ethyl 4-[4-(4-methoxypyridin-3-yl)piperidin-1-yl]piperidine-1-carboxylate | CAS: 82257-09-8 and Intermediate 3 | g | ¹H NMR (400 MHz, MeCN-d3) δ 1.24 (s, 3H) 1.56-1.92 (m, 4H) 2.07-2.23 (m, 12H) 2.30-2.60 (m, 2H) 2.73-3.01 (m, 1H) 3.17-3.61 (s, 3H) 3.87 (s, 3H) 4.10 (q, J = 1.00 Hz, 2H) 6.78-6.93 (m, 1H) 8.23-8.36 (m, 2H) | ES+ 362.4 |
| 49 | 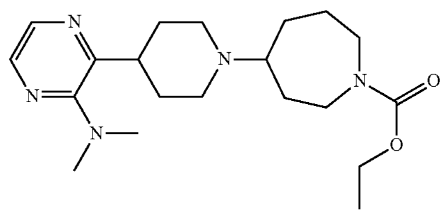 [SMILES: CCOC(=O)N1CCCC(N2CCC(c3nccnc3N(C)C)CC2)CC1] | ethyl 4-{4-[3-(dimethylamino)pyrazin-2-yl]piperidin-1-yl}azepane-1-carboxylate | CAS: 1316220-75-3 and Intermediate 3 | a | ¹H NMR (400 MHz, MeCN-d3) δ 1.24 (t, J = 6.69 Hz, 3H) 1.40-1.92 (m, 10H) 2.35 (d, J = 11.37 Hz, 2H) 2.44-2.60 (m, 2H) 2.88 (m, J = 9.00, 9.00 Hz, 2H) 3.09 (s, 6H) 3.29 (m, J = 9.30 Hz, 2H) 3.43-3.62 (m, 2H) 4.09 (q, J = 7.10 Hz, 2H) 7.68 (d, J = 1.00 Hz, 1H) 7.88 (d, J = 1.00 Hz, 1H) | ES+ 376.4 |
| 50 | 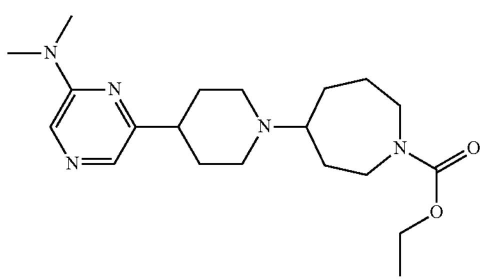 [SMILES: CCOC(=O)N1CCCC(N2CCC(c3cncc(N(C)C)n3)CC2)CC1] | ethyl 4-{4-[6-(dimethylamino)pyrazin-2-yl]piperidin-1-yl}azepane-1-carboxylate | CAS: 1316227-13-0 and Intermediate 3 | a | ¹H NMR (400 MHz, MeCN-d3) δ 1.24 (t, J = 1.00 Hz, 3H) 1.42-1.93 (m, 10H) 2.37 (m, J = 11.60 Hz, 2H) 2.47-2.58 (m, 1H) 2.74-3.07 (m, 9H) 3.31 (m, J = 9.30, 4.00 Hz, 2H) 3.52 (m, J = 13.90, 4.50 Hz, 2H) 4.10 (q, J = 1.00 Hz, 2H) 7.98 (d, J = 2.53 Hz, 1H) 8.05 (d, J = 2.53 Hz, 1H) | ES+ 376.4 |

TABLE 2-continued

| Ex. No. | Structure | Name | Intermediate | Synthetic method | ¹H NMR | LCMS data |
|---|---|---|---|---|---|---|
| 51 | 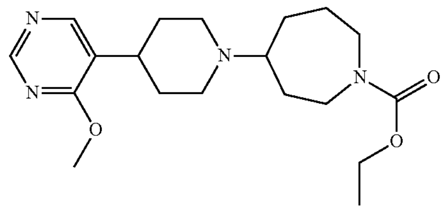 [SMILES: CCOC(=O)N1CCCC(N2CCC(c3cncnc3OC)CC2)CC1] | ethyl 4-[4-(4-methoxypyrimidin-5-yl)piperidin-1-yl]azepane-1-carboxylate | CAS: 4319-85-1 and Intermediate 3 | g | ¹H NMR (400 MHz, MeCN-d3) δ 1.24 (t, J = 6.44 Hz, 3H) 1.38-1.92 (m, 10H) 2.35 (q, J = 10.86 Hz, 2H) 2.51 (m, J = 9.90, 9.90 Hz, 1H) 2.61-2.76 (m, 1H) 2.83-2.99 (m, 2H) 3.16-3.38 (m, 2H) 3.44-3.61 (m, 2H) 3.98 (s, 3H) 4.09 (q, J = 6.65 Hz, 2H) 8.32 (s, 1H) 8.59 (s, 1H) | ES+ 363.4 |
| 52 | 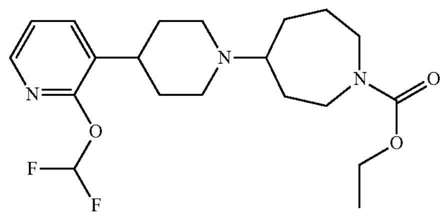 [SMILES: CCOC(=O)N1CCCC(N2CCC(c3cccnc3OC(F)F)CC2)CC1] | ethyl 4-{4-[2-(difluoromethoxy)pyridin-3-yl]piperidin-1-yl}azepane-1-carboxylate | CAS: 76-04-0 and Intermediate 8 | j | ¹H NMR (400 MHz, MeCN-d3) δ 1.24 (t, J = 6.06 Hz, 3H) 1.37-1.93 (m, 10H) 2.31-2.45 (m, 2H) 2.48-2.56 (m, 1H) 2.70-2.84 (m, 1H) 2.85-2.97 (m, 2H) 3.21-3.35 (m, 2H) 3.44-3.61 (m, 2H) 4.09 (q, J = 6.82 Hz, 2H) 7.18 (dd, J = 7.45, 4.93 Hz, 1H) 7.28-7.80 (m, 2H) 8.06 (dd, J = 4.93, 1.64 Hz, 1H) | ES+ 398.4 |
| 53 | 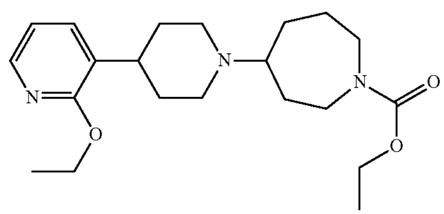 [SMILES: CCOC(=O)N1CCCC(N2CCC(c3cccnc3OCC)CC2)CC1] | ethyl 4-{4-[2-ethoxypyridin-3-yl]piperidin-1-yl}azepane-1-carboxylate | CAS: 75-03-6, and Intermediate 8 | k | ¹H NMR (400 MHz, MeCN-d3) δ 1.24 (t, J = 6.44 Hz, 3H) 1.36 (t, J = 7.07 Hz, 3H) 1.44-1.74 (m, 5H) 1.75-1.92 (m, 5H) 2.37 (m, J = 11.10 Hz, 2H) 2.46-2.57 (m, 1H) 2.70-2.82 (m, 1H) 2.84-2.97 (m, 2H) 3.19-3.36 (m, 2H) 3.45-3.60 (m, 2H) 4.09 (q, J = 6.80 Hz, 2H) 4.37 (q, J = 6.99 Hz, 2H) 6.88 (dd, J = 7.33, 5.05 Hz, 1H) 7.52 (d, J = 6.06 Hz, 1H) 7.87-8.00 (m, 1H) | ES+ 376.4 |
| 54 | 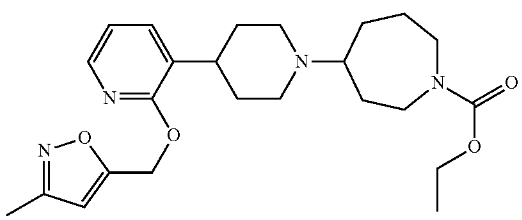 [SMILES: CCOC(=O)N1CCCC(N2CCC(c3cccnc3OCc3cc(C)no3)CC2)CC1] | ethyl 4-(4-{2-[(3-methyl-1,2-oxazol-5-yl)methoxy]pyridin-3-yl}piperidin-1-yl)azepane-1-carboxylate | CAS: 36958-61-9 and Intermediate 8 | k | ¹H NMR (400 MHz, MeCN-d3) δ 1.24 (t, J = 1.00 Hz, 3H) 1.72-1.94 (m, 9H) 2.07-2.13 (m, 3H) 2.27 (s, 3H) 2.31-2.58 (m, 3H) 2.69-2.81 (m, 1H) 2.83-2.97 (m, 2H) 3.21-3.39 (m, 2H) 4.08 (q, J = 1.00 Hz, 2H) 5.47 (s, 2H) 6.27 (s, 1H) 6.88-7.06 (m, 1H) 7.59 (d, J = 1.00 Hz, 1H) 8.00 (d, J = 1.00 Hz, 1H) | ES+ 443.4 |

TABLE 2-continued

| Ex. No. | Structure | Name | Intermediate | Synthetic method | $^1$H NMR | LCMS data |
|---|---|---|---|---|---|---|
| 55 | 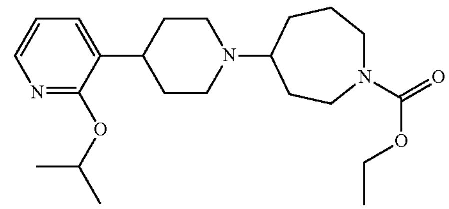 [SMILES: CCOC(=O)N1CCCC(N2CCC(c3cccnc3OC(C)C)CC2)CC1] | ethyl 4-{4-[2-(propan-2-yloxy)pyridin-3-yl]piperidin-1-yl}azepane-1-carboxylate | CAS: 75-30-9 and Intermediate 8 | k | $^1$H NMR (400 MHz, MeCN-d3) δ 1.24 (t, J = 6.32 Hz, 3H) 1.33 (d, J = 6.06 Hz, 6H) 1.44-1.93 (m, 10H) 2.36 (m, J = 11.40 Hz, 2H) 2.46-2.59 (m, 1H) 2.66-2.80 (m, 1H) 2.83-2.96 (m, 2H) 3.17-3.35 (m, 2H) 3.50 (m, J = 4.30 Hz, 2H) 4.09 (q, J = 6.80 Hz, 2H) 5.23-5.41 (m, 1H) 6.86 (dd, J = 7.33, 5.05 Hz, 1H) 7.50 (d, J = 7.33 Hz, 1H) 7.95 (d, J = 4.80 Hz, 1H) | ES+ 390.4 |
| 56 | 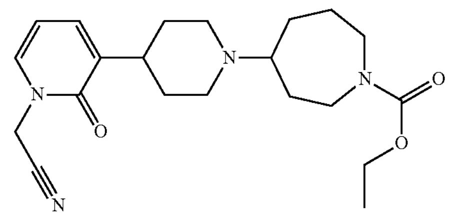 [SMILES: CCOC(=O)N1CCCC(N2CCC(c3cccn(CC#N)c3=O)CC2)CC1] | ethyl 4-{4-[1-(cyanomethyl)-2-oxo-1,2-dihydropyridin-3-yl]piperidin-1-yl}azepane-1-carboxylate | CAS: 590-17-0 and Intermediate 8 | k | $^1$H NMR (400 MHz, MeCN-d3) δ 1.24 (t, J = 6.57 Hz, 3H) 1.41-1.92 (m, 10H) 2.37 (m, J = 11.40 Hz, 2H) 2.46-2.56 (m, 1H) 2.66-2.78 (m, 1H) 2.80-2.95 (m, 2H) 3.19-3.35 (m, 2H) 3.44-3.60 (m, 2H) 4.09 (q, J = 6.80 Hz, 2H) 4.79 (s, 2H) 6.26 (t, J = 1.00 Hz, 1H) 7.29 (d, J = 6.82 Hz, 1H) 7.35 (d, J = 1.00 Hz, 1H) | ES+ 387.4 |
| 57 | 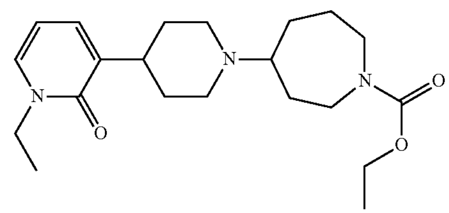 [SMILES: CCOC(=O)N1CCCC(N2CCC(c3cccn(CC)c3=O)CC2)CC1] | ethyl 4-{4-[1-ethyl-2-oxo-1,2-dihydropyridin-3-yl]piperidin-1-yl]azepane-1-carboxylate | CAS: 75-03-6, and Intermediate 8 | k | $^1$H NMR (400 MHz, MeCN-d3) δ 1.15-1.33 (m, 6H) 1.36-1.93 (m, 10H) 2.36 (m, J = 11.40 Hz, 2H) 2.46-2.57 (m, 1H) 2.65-2.78 (m, 1H) 2.80-2.92 (m, 2H) 3.29 (m, J = 10.10 Hz, 2H) 3.50 (m, J = 4.00 Hz, 2H) 3.95 (q, J = 7.16 Hz, 2H) 4.09 (q, J = 7.10 Hz, 2H) 6.16 (t, J = 6.82 Hz, 1H) 7.20 (d, J = 6.82 Hz, 1H) 7.32 (d, J = 6.57 Hz, 1H) | ES+ 376.4 |
| 58 | 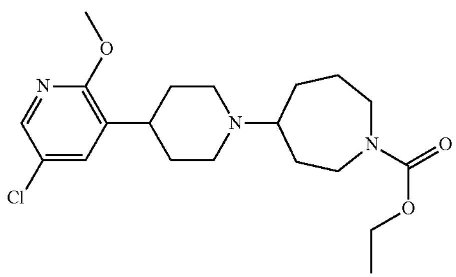 [SMILES: CCOC(=O)N1CCCC(N2CCC(c3cc(Cl)cnc3OC)CC2)CC1] | ethyl 4-[4-(5-chloro-2-methoxypyridin-3-yl)piperidin-1-yl]azepane-1-carboxylate | CAS: 102830-75-1 and Intermediate 3 | g | $^1$H NMR (400 MHz, MeCN-d3) δ 1.24 (t, J = 1.00 Hz, 3H) 1.39-1.92 (m, 8H) 1.90-1.96 (m, 2H) 2.43 (m, J = 11.10 Hz, 2H) 2.53-2.66 (m, 1H) 2.70-2.82 (m, 1H) 2.86-3.02 (m, 2H) 3.17-3.37 (m, 2H) 3.52 (dd, J = 13.01, 7.20 Hz, 2H) 3.92 (s, 3H) 4.09 (q, J = 6.82 Hz, 2H) 7.54 (d, J = 2.27 Hz, 1H) 7.99 (d, J = 2.53 Hz, 1H) | ES+ 396.3 |

TABLE 2-continued

| Ex. No. | Structure | Name | Intermediate | Synthetic method | ¹H NMR | LCMS data |
|---|---|---|---|---|---|---|
| 59 | 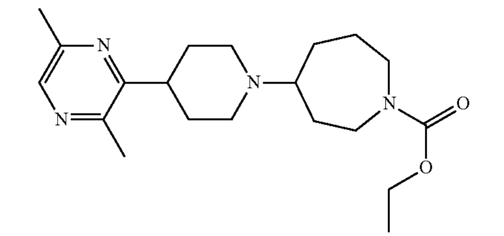 [SMILES: CCOC(=O)N1CCCC(N2CCC(c3nc(C)cnc3C)CC2)CC1] | ethyl 4-[4-(3,6-dimethylpyrazin-2-yl)piperidin-1-yl]azepane-1-carboxylate | CAS: 95-89-6 and Intermediate 3 | g | ¹H NMR (400 MHz, MeCN-d3) δ ppm 1.13-129 (m, 3H) 1.52 (d, J = 9.60 Hz, 2H) 1.64-1.93 (m, 8H) 2.28-2.57 (m, 9H) 2.73-2.99 (m, 3H) 3.19-3.37 (m, 2H) 3.52 (m, J = 14.10 Hz, 2H) .01-4.17 (m, 2H) 8.14 (s, 1H) | ES+ 361.4 |
| 60 | 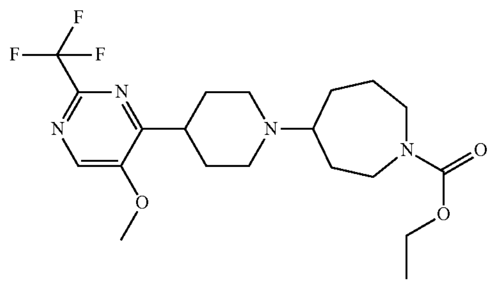 [SMILES: CCOC(=O)N1CCCC(N2CCC(c3nc(C(F)(F)F)ncc3OC)CC2)CC1] | ethyl 4-{4-[5-methoxy-2-(trifluoromethyl)pyrimidin-4-yl]piperidin-1-yl}azepane-1-carboxylate | CAS: 808770-41-4 and Intermediate 3 | g | ¹H NMR (400 MHz, MeCN-d3) δ ppm 1.24 (t, J = 6.95 Hz, 3H) 1.40-1.93 (m, 10H) 2.37 (m, J = 9.30 Hz, 2H) 2.46-2.67 (m, 1H) 2.92 (m, J = 9.10, 9.10 Hz, 2H) 3.11 (m, J = 5.80 Hz, 1H) 3.20-3.38 (m, 2H) 3.43-3.60 (m, 2H) 4.01 (s, 3H) 4.09 (q, J = 7.07 Hz, 2H) 8.46 (s, 1H) | ES+ 431.4 |
| 61 | 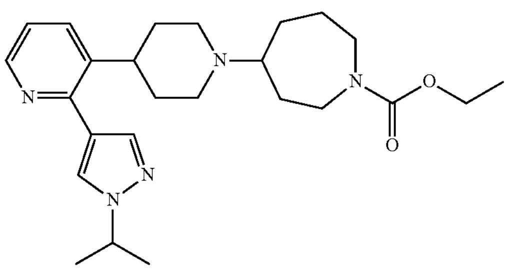 [SMILES: CCOC(=O)N1CCCC(N2CCC(c3cccnc3-c3cnn(C(C)C)c3)CC2)CC1] | ethyl 4-(4-{2-[1-(propan-2-yl)-1H-pyrazol-4-yl]pyridin-3-yl}piperidin-1-yl)azepane-1-carboxylate | CAS: 870487-10-2 and Intermediate 10 | n | ¹H NMR (400 MHz, MeOD) δ 1.3 (t, 3H), 1.7-1.9 (m, 5H), 1.6 (d, 8H), 1.9-2.2 (m, 3H), 2.55(s, 2H), 2.75 (s, 1H), 3.1 (s, 3H), 3.4 (q, 2H), 3.6 (m, 2H), 4.15 (m, 2H), 4.65 (m, 1H), 7.35 (t, 1H), 7.75 (s, 1H), 7.85 (d, 1H), 7.95 (s, 1H), 8.35 (d, 1H) | ES+ 440.2 |
| 62 | 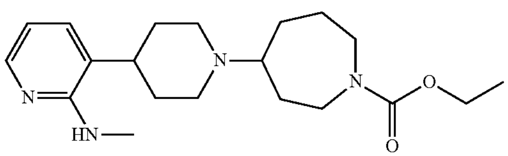 [SMILES: CCOC(=O)N1CCCC(N2CCC(c3cccnc3NC)CC2)CC1] | ethyl 4-{4-[2-(methylamino)pyridin-3-yl]piperidin-1-yl}azepane-1-carboxylate | CAS: 593-51-1 and Intermediate 10 | p | ¹H NMR (400 MHz, MeOD) δ 1.3 (t, 3H), 1.5-1.65 (m, 2H), 1.7 (m, 3H), 1.85-1.95 (m, 2H), 2.0-2.15 (m, 3H), 2.5 (m, 1H), 2.6-2.7 (m, 3H), 2.9 (d, 3H), 3.0 (d, 2H), 3.4 (m, 2H), 3.6 (m, 2H), 4.15 (m, 2H), 6.6 (t, 1H), 7.35 (d, 1H), 7.85 (d, 1H) | ES+ 361.1 |

| Ex. No. | Structure | Name | Intermediate | Synthetic method | ¹H NMR | LCMS data |
|---|---|---|---|---|---|---|
| 63 | 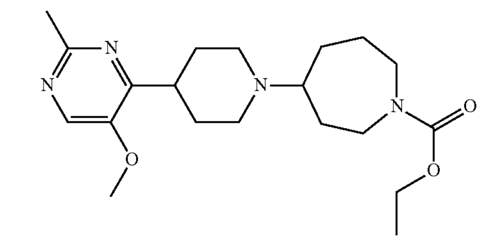 [SMILES: CCOC(=O)N1CCCC(N2CCC(c3nc(C)ncc3OC)CC2)CC1] | ethyl 4-[4-(5-methoxy-2-methylpyrimidin-4-yl)piperidin-1-yl]azepane-1-carboxylate | Intermediate 11 and Intermediate 3 | a | ¹H NMR (400 MHz, MeCN-d3) δ ppm 1.25 (t, J = 1.00 Hz, 3H) 1.38-1.92 (m, 9H) 2.34 (m, J = 11.60 Hz, 2H) 2.43-2.53 (m, 1H) 2.47-2.61 (m, 4H) 2.89 (m, J = 9.50, 9.50 Hz, 2H) 2.95-3.11 (m, 1H) 3.22-3.39 (m, 2H) 3.51 (m, J = 14.00, 4.70 Hz, 2H) 3.76-3.92 (m, 3H) 4.02-4.20 (m, 2H) 8.21 (s, 1H) | ES+ 377.4 |
| 64 | 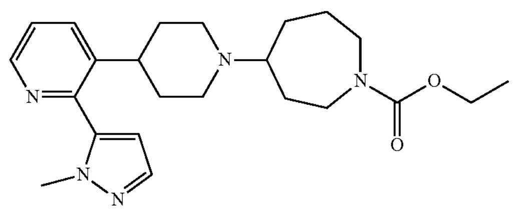 [SMILES: CCOC(=O)N1CCCC(N2CCC(c3cccnc3-c3ccnn3C)CC2)CC1] | ethyl 4-{4-[2-(1-methyl-1H-pyrazol-5-yl)pyridin-3-yl]piperidin-1-yl}azepane-1-carboxylate | CAS: 80818-74-0 and Intermediate 10 | n | ¹H NMR (400 MHz, CD₃CN) δ 1.3 (t, 3H), 1.5 (m, 3H), 1.7 (m, 4H), 1.85 (d, 3H), 2.2 (m, 2H), 2.5 (m, 1H), 2.65 (m, 1H), 2.8 (m, 2H), 3.25 (t, 2H), 3.5 (m, 2H), 3.7 (s, 3H), 4.1 (m, 2H), 6.35 (s, 1H), 7.4 (dd, 1H), 7.5 (s, 1H), 7.85 (dd, 1H), 8.55 (s, 1H) | ES+ 412.2 |
| 65 | 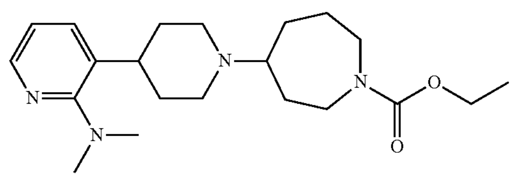 [SMILES: CCOC(=O)N1CCCC(N2CCC(c3cccnc3N(C)C)CC2)CC1] | ethyl 4-{4-[2-(dimethylamino)pyridin-3-yl]piperidin-1-yl}azepane-1-carboxylate | CAS: 506-59-2 and Intermediate 10 | p | ¹H NMR (400 MHz, MeOD) δ 1.3 (m, 3H), 1.5-1.65 (m, 3H), 1.7-1.85 (m, 5H), 1.95-2.15 (m, 3H), 2.5-2.65 (m, 3H), 2.8 (s, 6H), 3.0 (t, 2H), 3.45 (d, 2H), 3.65 (t, 2H), 4.15 (m, 2H), 7.05 (t, 1H), 7.65 (d, 1H), 8.05 (s, 1H) | ES+ 375.2 |
| 66 | 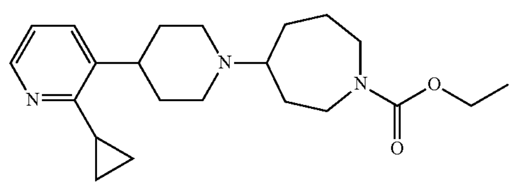 [SMILES: CCOC(=O)N1CCCC(N2CCC(c3cccnc3C3CC3)CC2)CC1] | ethyl 4-[4-(2-cyclopropylpyridin-3-yl)piperidin-1-yl]azepane-1-carboxylate | CAS: 411235-57-9 and Intermediate 10 | n | ¹H NMR (400 MHz, CD₃CN) δ 0.9-1.0 (m, 2H), 1.05 (m, 2H), 1.25 (m, 3H), 1.45-1.55 (m, 2H), 1.85-1.95 (m, 5H), 2.15-2.35 (m, 3H), 2.35-2.5 (m, 2H), 2.5-2.6 (m, 1H), 2.85-3.0 (m, 3H), 3.3 (t, 2H), 3.5 (m, 2H), 4.1 (d, 2H), 7.05 (t, 1H), 7.55 (d, 1H), 8.25 (d, 1H) | ES+ 372.1 |
| 67 | 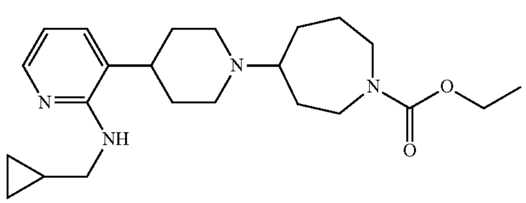 [SMILES: CCOC(=O)N1CCCC(N2CCC(c3cccnc3NCC3CC3)CC2)CC1] | ethyl 4-(4-{2-[(cyclopropylmethyl)amino]pyridin-3-yl}piperidin-1-yl)azepane-1-carboxylate | CAS: 2516-47-1 and Intermediate 10 | p | ¹H NMR (400 MHz, MeOD) δ 0.35 (m, 2H), 0.5 (m,2H), 1.2 (m, 1H), 1.35 (m, 3H), 1.5-1.65 (m, 3H), 1.7-1.8 (m, 3H), 1.85-2.0 (d, 3H), 2.0-2.15 (m, 2H), 2.5-2.7 (q, 4H), 2.9-3.0 (s, 2H), 3.25 (d, 2H), 3.35-3.5 (m, 2H), 3.55-3.65 (m,2H), 4.15 (m, 2H), 6.6 (t, 1H), 7.35 (dd, 1H), 7.85 (dd, 1H) | ES+ 401.2 |

TABLE 2-continued

| Ex. No. | Structure | Name | Intermediate | Synthetic method | ¹H NMR | LCMS data |
|---|---|---|---|---|---|---|
| 68 | 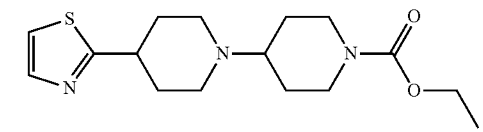 | ethyl 4-[4-(1,3-thiazol-2-yl)piperidin-1-yl]piperidine-1-carboxylate | CAS: 788822-03-7 and CAS: 29976-53-2 | a | ¹H NMR (400 MHz, MeCN-d3) δ ppm 1.23 (t, J = 7.07 Hz, 3H) 1.41 (m, J = 12.10, 12.10, 12.10, 4.40 Hz, 2H) 1.60-1.85 (m, 4H) 2.09 (d, J = 12.38 Hz, 2H) 2.35 (m, J = 11.60, 11.60, 1.90 Hz, 2H) 2.49 (m, J = 11.30, 11.30, 3.40, 3.40 Hz, 1H) 2.78 (m, J = 11.60, 11.60 Hz, 2H) 2.90-3.12 (m, 3H) 3.84-4.19 (m, 4H) 7.36 (d, J = 3.28 Hz, 1H) 7.68 (d, J = 3.28 Hz, 1H) | ES+ 324.4 |
| 69 | 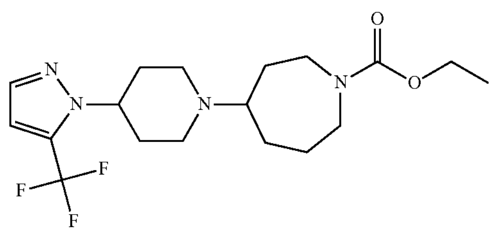 [SMILES: CCOC(=O)N1CCCC(N2CCC(n3nccc3C(F)(F)F)CC2)CC1] | ethyl 4-{4-[5-(trifluoromethyl)-1H-pyrazol-1-yl]piperidin-1-yl}azepane-1-carboxylate | CAS: 20154-03-4 and Intermediate 3 | q | ¹H NMR (400 MHz, MeOD) δ ppm 1.3 (t, 3H), 1.7-1.5 (m, 2H), 1.75 (m, 1H), 2.1-1.9 (m, 5H), 2.2-2.4 (m, 2H), 2.5-2.7 (m, 3H), 3.0 (m, 2H), 3.4 (m, 2H), 3.6 (m, 2H), 4.15 (m, 2H), 4.3 (m, 1H), 6.75 (d, 1H), 7.6 (d, 1H) | ES+ 389.1 |
| 70 | 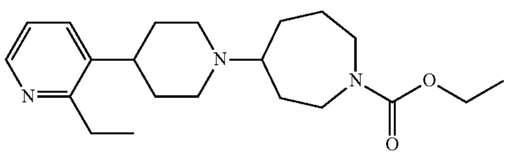 [SMILES: CCOC(=O)N1CCCC(N2CCC(c3cccnc3CC)CC2)CC1] | ethyl 4-[4-(2-ethylpyridin-3-yl)piperidin-1-yl]azepane-1-carboxylate | CAS : 925-90-6 and Intermediate 10 | r | ¹H NMR (400 MHz, MeOD) δ ppm 1.25 (t, 3H), 1.5-1.7 (m, 2H), 1.75 (m, 1H), 1.8 (m, 4H), 1.95 (m, 1H), 2.1-2.0 (m, 2H), 2.5-2.7 (m, 3H), 2.9-2.8 (m, 3H), 3.0 (m, 2H), 3.4 (m, 2H), 3.6 (m, 2H), 4.15 (m, 2H), 7.25 (t, 1H), 7.75 (d, 1H), 8.3 (d, 1H) | ES+ 360.1 |
| 71 | 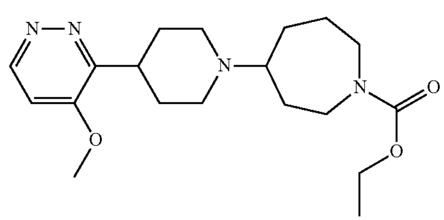 [SMILES: CCOC(=O)N1CCCC(N2CCC(c3nnccc3OC)CC2)CC1] | ethyl 4-[4-(4-methoxypyridazin-3-yl)piperidin-1-yl]azepane-1-carboxylate | CAS: 1677-81-2 and intermediate 3 | g | ¹H NMR (400 MHz, DMSO-d6) δ ppm 1.07-1.22 (m, 3H) 1.31-1.98 (m, 10H) 2.20-2.48 (m, 3H) 2.73-2.92 (m, 2H) 2.95-3.11 (m, 1H) 3.15-3.27 (m, 2H) 3.39-3.57 (m, 2H) 3.89 (s, 3H) 4.04 (q, J = 1.00 Hz, 2H) 7.17 (d, J = 6.06 Hz 1H) 8.88 (d, J = 5.81 Hz, 1H) | ES+ 363.3 |
| 72 | 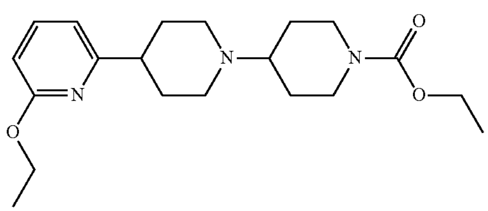 [SMILES: CCOC(=O)N1CCC(N2CCC(c3cccc(OCC)n3)CC2)CC1] | ethyl 4-[4-(6-ethoxypyridin-2-yl)piperidin-1-yl]piperidine-1-carboxylate | CAS: 42144-78-5 and intermediate 3 | g | ¹H NMR (400 MHz, MeCN-d3) δ ppm 1.24 (t, J = 7.07 Hz, 3H) 1.29-1.50 (m, 5H) 1.67-1.92 (m, 6H) 2.31 (td, J = 11.62, 2.27 Hz, 2H) 2.40-2.63 (m, 2H) 2.79 (m, J = 11.60, 11.60 Hz, 2H) 3.00 (d, J = 11.62 Hz, 2H) 3.94-4.18 (m, 4H) 4.36 (q, J = 7.07 Hz, 2H) 6.54 (d, J = 8.34 Hz, 1H) 6.79 (d, J = 7.07 Hz, 1H) 7.56 (t, J = 7.71 Hz, 1H) | ES+ 362.4 |

TABLE 2-continued

| Ex. No. | Structure | Name | Intermediate | Synthetic method | ¹H NMR | LCMS data |
|---|---|---|---|---|---|---|
| 73 | 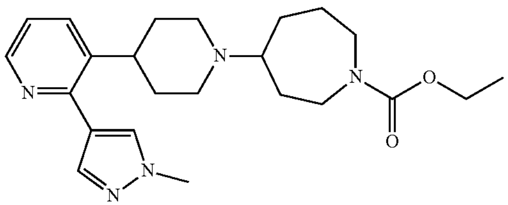 [SMILES: CCOC(=O)N1CCCC(N2CCC(c3cccnc3-c3cnn(C)c3)CC2)CC1] | ethyl 4-{2-(1-methyl-1H-pyrazol-4-yl)pyridin-3-yl]piperidin-1-yl}azepane-1-carboxylate | CAS: 847818-55-7 and Intermediate 10 | n | ¹H NMR (400 MHz, MeOD) δ 1.25 (t, 3H), 1.45-1.8 (m, 3H), 1.85 (m, 4H), 1.9-2.1 (m, 3H), 2.5(m, 2H), 2.7 (m, 1H), 3.0 (m, 3H), 3.4 (m, 2H), 3.6 (m, 2H), 4.0 (s, 3H), 4.15 (m, 2H), 7.35 (m, 1H), 7.7 (s, 1H), 7.85 (d, 1H), 7.9 (s, 1H), 8.4 (d, 1H) | ES+ 412.2 |
| 74 | 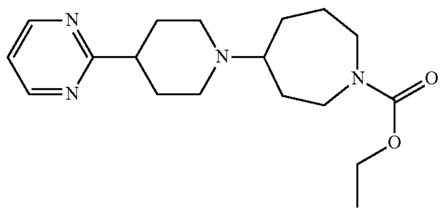 [SMILES: CCOC(=O)N1CCCC(N2CCC(c3ncccn3)CC2)CC1] | ethyl 4-[4-(pyrimidin-2-yl)piperidin-1-yl]azepane-1-carboxylate | CAS: 1722-12-9 and Intermediate 3 | g | ¹H NMR (400 MHz, MeCNd3) δ ppm 1.24 (t, J = 6.32 Hz, 3H) 1.40-1.92 (m, 8H) 2.10-2.21 (m, 2H) 2.29-2.61 (m, 3H) 2.69-3.00 (m, 3H) 3.29 (m, J = 13.90, 9.50, 4.20 Hz, 2H) 3.52 (m, 3H) 4.09 (q, J = 6.60 Hz, 2H) 7.21 (m, J = 13.40 Hz, 2H) 4.09 (q, J = 6.60 Hz, 2H) 7.21 (m, J = 4.90, 4.90 Hz, 1H) 8.68 (m, J = 4.80 Hz, 2H) | ES+ 333.4 |
| 75 | 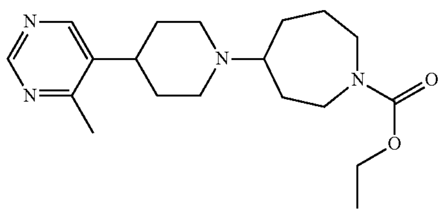 [SMILES: CCOC(=O)N1CCCC(N2CCC(c3cncnc3C)CC2)CC1] | ethyl 4-[4-(4-methylpyrimidin-5-yl)piperidin-1-yl]azepane-1-carboxylate | CAS: 1439-09-4 and Intermediate 3 | g | ¹H NMR (400 MHz, ACETONITRILE-d3) δ ppm 1.24 (t, J = 6.06 Hz, 3H) 1.41-1.93 (m, 10H) 2.29-2.47 (m, 2H) 2.48-2.57 (m, 4H) 2.62-2.78 (m, 1H) 2.84-2.98 (m, 2H) 3.20-3.37 (m, 2H) 3.44-3.63 (m, 2H) 4.10 (q, J = 6.30 Hz, 2H) 8.53 (s, 1H) 8.83 (s, 1H) | ES+ 347.4 |
| 76 | 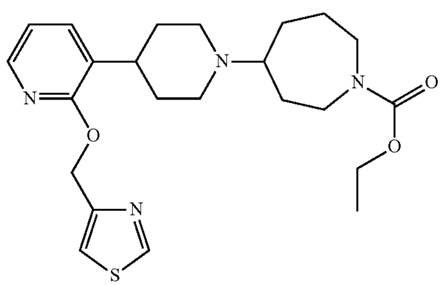 [SMILES: CCOC(=O)N1CCCC(N2CCC(c3cccnc3OCc3cscn3)CC2)CC1] | ethyl 4-{4-[2-(1,3-thiazol-4-ylmethoxy)pyridin-3-yl]piperidin-1-yl}azepane-1-carboxylate | Intermediate 12 and Intermediate 3 | a | ¹H NMR (400 MHz, MeCN-d3) δ 1.24 (t, J = 1.00 Hz, 3H) 1.55 (m, 2H) 1.6-1.9 (m, 8H) 2.4-3.2 (m, 6H) 3.3 (m, 2H) 3.55 (m, 2H) 4.1 (q, J = 1.00 Hz, 2H) 5.55 (s, 2H) 6.95 (m, 1H) 7.55 (s, 1H) 7.6 (m, 1H) 8.05 (m, 1H) 8.9 (s, 1H) | ES+ 445.4 |

TABLE 2-continued

| Ex. No. | Structure | Name | Intermediate | Synthetic method | 1H NMR | LCMS data |
|---|---|---|---|---|---|---|
| 77 | 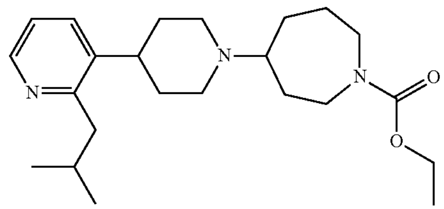 [SMILES: CCOC(=O)N1CCCC(N2CCC(c3cccnc3CC(C)C)CC2)CC1] | ethyl 4-{4-[2-(2-methylpropyl)pyridin-3-yl]piperidin-1-yl}azepane-1-carboxylate | CAS : 926-62-5 and Intermediate 10 | s | 1H NMR (400 MHz, MeCN-d3) δ ppm 0.94 (d, J = 6.57 Hz, 6H) 1.18-1.29 (m, 3H) 1.42-1.94 (m, 7H) 2.08-2.12 (m, 2H) 2.38-3.06 (m, 8H) 3.19-3.37 (m, 3H) 3.44-3.67 (m, 2H) 3.97-4.18 (m, 2H) 7.08-7.20 (m, 1H) 7.58-7.67 (m, 1H) 8.22-8.39 (m, 1H) | ES+ 388.5 |
| 78 | 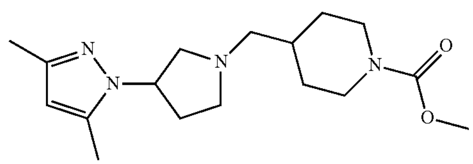 | methyl 4-{[3-(3,5-dimethyl-1H-pyrazol-1-yl)pyrrolidin-1-yl]methyl}piperidine-1-carboxylate | CAS: 1177347-39-5, CAS: 137076-22-3 and CAS: 79-22-1 | i | 1H NMR (400 MHz, MeCN-d3) δ ppm 1.05 (qd, J = 12.04, 3.79 Hz, 2H) 1.53-1.83 (m, 3H) 2.15-2.41 (m, 10H) 2.54-2.87 (m, 5H) 3.01 (m, J = 8.60, 8.60 Hz, 1H) 3.63 (s, 3H) 4.05 (m, J = 11.10 Hz, 2H) 4.63-4.86 (m, 1H) 5.78 (s, 1H) | ES+ 321.4 |
| 79 | 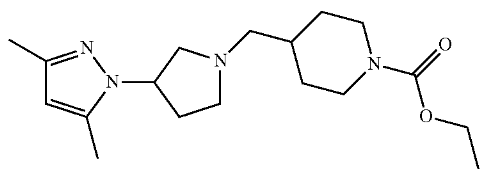 [SMILES: CCOC(=O)N1CCC(CN2CCC(n3nc(C)cc3C)C2)CC1] | ethyl 4-{[3-(3,5-dimethyl-1H-pyrazol-1-yl)pyrrolidin-1-yl]methyl}piperidine-1-carboxylate | CAS: 1177347-39-5, CAS: 137076-22-3 and CAS: 541-41-3 | i | 1H NMR (400 MHz, MeCN-d3) δ ppm 1.05 (qd, J = 12.00, 3.92 Hz, 2H) 1.23 (t, J = 7.07 Hz, 3H) 1.57-1.86 (m, 3H) 1.98-2.00 (m, 2H) 2.15-2.43 (m, 8H) 2.52-2.85 (m, 5H) 3.01 (m, J = 8.60, 8.60 Hz, 1H) 4.08 (m, J = 7.10, 7.10, 7.10 Hz, 4H) 4.60-4.83 (m, 1H) 5.78 (s, 1H) | ES+ 335.5 |
| 80 | 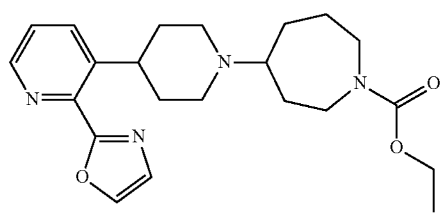 [SMILES: CCOC(=O)N1CCCC(N2CCC(c3cccnc3-c3ncco3)CC2)CC1] | ethyl 4-{4-[2-(1,3-oxazol-2-yl)pyridin-3-yl]piperidin-1-yl}azepane-1-carboxylate | CAS : 145214-05-7 and Intermediate 10 | t | 1H NMR (300 MHz, MeCN-d3) δ ppm 1.21 (t, J = 6.99 Hz, 3H) 1.39-1.55 (m, 1H) 1.58-1.73 (m, 2H) 1.73-1.90 (m, 5H) 2.24-2.39 (m, 2H) 2.43-2.54 (m, 1H) 2.86 (br. s., 2H) 3.18-3.33 (m, 2H) 3.41-3.66 (m, 2H) 4.07 (q, J = 6.99 Hz, 2H) 7.32 (s, 1H) 7.42 (dd, J = 7.93, 4.53 Hz, 1H) 7.89 (d, J = 8.12 Hz, 1H) 7.96 (s, 1H) 8.52 (dd, J = 4.53, 1.51 Hz, 1H) | ES+ 399.4 |
| 81 | 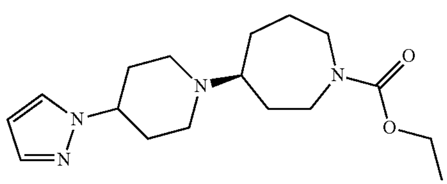 [SMILES: CCOC(=O)N1CCC[C@H](N2CCC(n3cccn3)CC2)CC1] | ethyl (4S)-4-[4-(1H-pyrazol-1-yl)piperidin-1-yl]azepane-1-carboxylate | CAS : 69026l-87-1 and (R)-ethyl 4-(tosyloxy)azepane-1-carboxylate | | 1H NMR (400 MHz, DMSO-d6) δ 1.15 (t, J = 7.3, 3H), 1.33-1.45 (m, 2H), 1.50-1.62 (m, 1H), 1.77-1.89 (m, 4H), 1.91-1.96 (m, 2H), 2.29-2.40 (m, 2H), 2.75-2.87 (m, 2H), 3.20 (m, 2H), 3.30-3.35 (m, 2H), 3.37-3.43 (m, 2H), 3.96-4.08 (m, 4H), 6.18 (m, 1H), 7.30-7.40 (m, 1H), 7.71 (m, 1H) | ES+ 321.1 |

TABLE 2-continued

| Ex. No. | Structure | Name | Intermediate | Synthetic method | $^1$H NMR | LCMS data |
|---|---|---|---|---|---|---|
| 82 | 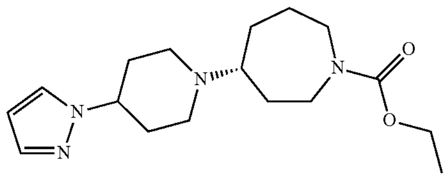 | ethyl (4R)-4-[4-(1H-pyrazol-1-yl)piperidin-1-yl]azepane-1-carboxylate | CAS: 69026l-87-1 and (S)-ethyl 4-(tosyloxy)azepane-1-carboxylate | | $^1$H NMR (400 MHz, DMSO-d6) δ 1.15 (t, J = 7.3, 3H), 1.33-1.45 (m, 2H), 1.50-1.62 (m, 1H), 1.77-1.89 (m, 4H), 1.91-1.96 (m, 2H), 2.29-2.40 (m, 2H), 2.75-2.87 (m, 2H), 3.20 (m, 2H), 3.30-3.35 (m, 2H), 3.37-3.43 (m, 2H), 3.96-4.08 (m, 4H), 6.18 (m, 1H), 7.30-7.40 (m, 1H), 7.71 (m, 1H) | ES+ 321.1 |
| 83 | 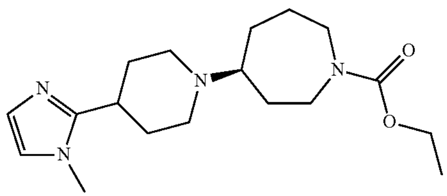 [SMILES: CCOC(=O)N1CCC[C@H](N2CCC(c3nccn3C)CC2)CC1] | ethyl (4S)-4-[4-(1-methyl-1H-imidazol-2-yl)piperidin-1-yl]azepane-1-carboxylate | CAS: 1084976-68-0 and (R)-ethyl 4-(tosyloxy)azepane-1-carboxylate | | $^1$H NMR (400 MHz, DMSO-d6) δ 1.15 (t, J = 7.3, 3H), 1.32-1.45 (m, 2H), 1.61 (m, 1H), 1.66-1.78 (m, 3H), 2.18-2.31 (m, 2H), 2.33-2.45 (m, 1H), 2.60 (m, 1H), 2.67-2.79 (m, 2H), 3.11-3.23 (m, 3H), 3.41 (m, 2H), 3.47-3.55 (m, 3H), 4.02 (q, J = 7.3, 2H), 6.67 (s, 1H), 6.91 (s, 1H) | ES+ 335.2 |
| 84 | 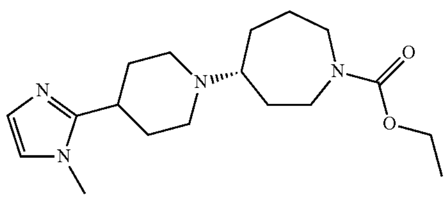 [SMILES: CCOC(=O)N1CCC[C@@H](N2CCC(c3nccn3C)CC2)CC1] | ethyl (4R)-4-[4-(1-methyl-1H-imidazol-2-yl)piperidin-1-yl]azepane-1-carboxylate | CAS: 1084976-68-0 and (S)-ethyl 4-(tosyloxy)azepane-1-carboxylate | | $^1$H NMR (400 MHz, DMSO-d6) δ 1.15 (t, J = 7.3, 3H), 1.32-1.45 (m, 2H), 1.61 (m, 1H), 1.66-1.78 (m, 3H), 2.18-2.31 (m, 2H), 2.33-2.45 (m, 1H), 2.60 (m, 1H), 2.67-2.79 (m, 2H), 3.11-3.23 (m, 3H), 3.41 (m, 2H), 3.47-3.55 (m, 3H), 4.02 (q, J = 7.3, 2H), 6.67 (s, 1H), 6.91 (s, 1H) | ES+ 335.2 |
| 85 | 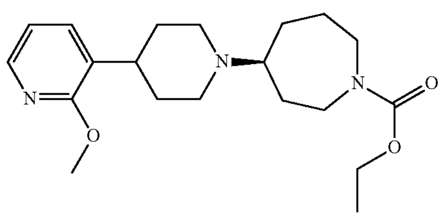 [SMILES: CCOC(=O)N1CCC[C@H](N2CCC(c3cccnc3OC)CC2)CC1] | ethyl (4S)-4-[4-(2-methoxypyridin-3-yl)piperidin-1-yl]azepane-1-carboxylate | CAS: 171425-45-9 and (R)-ethyl 4-(tosyloxy)azepane-1-carboxylate | | $^1$H NMR (400 MHz, CD2Cl2) δ 1.24 (t, J = 6.8 Hz, 3H), 1.41-1.71 (m, 6H), 1.77-2.01 (m, 4H), 2.33-2.55 (m, 3H), 2.71-2.93 (m, 3H), 3.26 (m, 2H), 3.54 (m, 2H), 3.91 (s, 3H), 4.09 (q, J = 6.8 Hz, 2H), 6.83 (dd, J = 7.2, 4.9 Hz, 1H), 7.45 (d, J = 7.2 Hz, 1H), 7.96 (dd, J = 4.9, 1.6 Hz, 1H) | ES+ 362 |
| 86 | 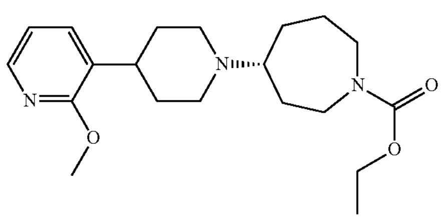 [SMILES: CCOC(=O)N1CCC[C@@H](N2CCC(c3cccnc3OC)CC2)CC1] | ethyl (4R)-4-[4-(2-methoxypyridin-3-yl)piperidin-1-yl]azepane-1-carboxylate | CAS: 171425-45-9 and (S)-ethyl 4-(tosyloxy)azepane-1-carboxylate | | $^1$H NMR (400 MHz, CD2Cl2) δ 1.24 (t, J = 6.8 Hz, 3H), 1.41-1.71 (m, 6H), 1.77-2.01 (m, 4H), 2.33-2.55 (m, 3H), 2.71-2.93 (m, 3H), 3.26 (m, 2H), 3.54 (m, 2H), 3.91 (s, 3H), 4.09 (q, J = 6.8 Hz, 2H), 6.83 (dd, J = 7.2, 4.9 Hz, 1H), 7.45 (d, J = 7.2 Hz, 1H), 7.96 (dd, J = 4.9, 1.6 Hz, 1H) | ES+ 362 |

Biological Efficacy of Compounds of the Invention
In Vitro M4 &M2 Functional Assay The functional activity of compounds at the M4 and M2 receptors was determined by measuring changes in the level of intracellular calcium ions caused by signalling cascades mediated by the receptor. Intracellular Calcium levels were measured using a calcium sensitive fluorescent dye, calcium 5 (Molecular Devices) The changes in fluorescence were monitored by a fluorescent imager, FLiPR Tetra (Molecular devices). Increases in intracellular calcium were readily detected upon activation of both receptors by the muscarinic receptor agonist Acetylcholine.

CHOK1 cells stably expressing human M4 or M2 receptor and co-expressing the accessory g-protein $G\alpha16$ were routinely grown as monolayers in Hams-F12 medium (Invitrogen) supplemented with 10% foetal bovine serum (FBS) (Hyclone), 500 ug/mL Geneticin and 250 ug/mL zeocin (both invitrogen) in 5% $CO_2$ at 37° C. Once confluent cells cryopreserved by freezing at −186° C. in freezing solution (90% FBS 10% DMSO) (Sigma-Aldrich Co.). Twenty-four hours prior to testing cells resuscitated and freezing media removed via centrifugation, cells then seeded in a black walled clear bottom 384 well plates (Corning) at a density of 15,000 cells/well in Hams F12 media supplemented with 10% FBS. On the day of assay, growth media was removed and replaced with 63 µl of Calcium 5 dye solution (Molecular Devices) in assay buffer (HBSS, 20 mM HEPES, 0.1% BSA, 1 mM Probenecid pH7.4 (Sigma-Aldrich Co.)) per well (each vial of Calcium 5 resuspended in 27 mL of assay buffer). Cells were then incubated for 45 minutes at 37° C., 5% $CO_2$. Compound was serially diluted in DMSO (log/half log) before being diluted 1:20 with assay buffer. 7 µl of compound diluted in assay buffer was then added to cells on FLiPR tetra and fluorescence intensity measured for 5 minutes. $EC_{50}$ values for compounds were determined from ten point half log scale dose-response studies and represent the concentration of compound required to prevent 50% inhibition of its own maximal response. Curves were generated using the average of duplicate wells for each data point and analyzed using non-linear regression of four parameter dose response. Percentage Relative efficacy (RE) to an $EC_{100}$ concentration of acetylcholine was reported for all compounds. The results are set out in Table 3 below in which the term "No Response" means that there was no significant response of calcium flux in the assay indicative of agonism.

TABLE 3

| Example no. | M4 $EC_{50}$ (µM)/ M4 % RE | M2 $EC_{50}$ (µM)/ M2 % RE |
|---|---|---|
| 1 | 2.36/49 | >10 µM/34% @ 10 µM |
| 2 | 1.87/51 | No Response |
| 3 | 0.33/59 | 1.54/38 |
| 4 | 0.14/74 | No Response |
| 5 | 0.25/49 | >10 µM/25% @ 10 µM |
| 6 | 0.19/53 | No Response |
| 7 | 0.26/75 | >10 µM/26% @ 10 µM |
| 8 | 0.32/59 | No Response |
| 9 | 1.05/62 | No Response |
| 10 | 1.74/44 | No Response |
| 11 | 0.96/41 | No Response |
| 12 | 0.52/82 | >10 µM/28% @ 10 µM |
| 13 | 2.88/24 | No Response |
| 14 | 0.75/55 | No Response |
| 15 | 1.28/44 | No Response |
| 16 | 0.40/72 | >10 µM/24% @ 10 µM |
| 17 | 0.81/50 | No Response |
| 18 | 0.41/45 | No Response |

TABLE 3-continued

| Example no. | M4 $EC_{50}$ (µM)/ M4 % RE | M2 $EC_{50}$ (µM)/ M2 % RE |
|---|---|---|
| 19 | 1.51/64 | No Response |
| 20 | 0.19/77 | 2.26/37 |
| 21 | 2.68/45 | No Response |
| 22 | 0.20/68 | 0.68/38 |
| 23 | 0.75/67 | No Response |
| 24 | 1.37/45 | No Response |
| 25 | 0.27/46 | No Response |
| 26 | 0.13/51 | No Response |
| 27 | 0.32/55 | No Response |
| 28 | 1.48/59 | No Response |
| 29 | 1.83/29 | No Response |
| 30 | 1.66/27 | No Response |
| 31 | 2.26/30 | No Response |
| 32 | 0.22/73 | No Response |
| 33 | 0.18/61 | No Response |
| 34 | 0.09/90 | No Response |
| 35 | 0.03/102 | No Response |
| 36 | 6.73/25 | No Response |
| 37 | 3.34/39 | No Response |
| 38 | 0.03/92 | 0.16/75 |
| 39 | 0.74/41 | No Response |
| 40 | 0.14/62 | No Response |
| 41 | 0.26/54 | No Response |
| 42 | 0.02/82 | No Response |
| 43 | 0.02/94 | 0.18/62 |
| 44 | 0.37/52 | No Response |
| 45 | 0.46/25 | No Response |
| 46 | 1.55/31 | No Response |
| 47 | 0.16/72 | No Response |
| 48 | 0.25/63 | No Response |
| 49 | 0.21/53 | No Response |
| 50 | 0.46/50 | No Response |
| 51 | 0.31/69 | No Response |
| 52 | 0.01/96 | >10 µM/25% @ 10 µM |
| 53 | 0.06/80 | No Response |
| 54 | 0.02/94 | No Response |
| 55 | 0.13/67 | >10 µM/26% @ 10 µM |
| 56 | 2.35/24 | No Response |
| 57 | 0.89/37 | No Response |
| 58 | 0.002/95 | No Response |
| 59 | 0.53/30 | No Response |
| 60 | 0.18/68 | No Response |
| 61 | 0.15/66 | No Response |
| 62 | 0.36/53 | No Response |
| 63 | 0.56/43 | No Response |
| 64 | 3.14/35 | No Response |
| 65 | 0.19/87 | No Response |
| 66 | 0.12/84 | No Response |
| 67 | 0.99/37 | No Response |
| 68 | 0.54/45 | No Response |
| 69 | 0.63/63 | >10 µM/21% @ 10 µM |
| 70 | 0.21/64 | No Response |
| 71 | 1.05/45 | No Response |
| 72 | 0.27/63 | 2.02/20 |
| 73 | 0.65/53 | No Response |
| 74 | 1.05/61 | >10 µM/20% @ 10 µM |
| 75 | 1.01/52 | No Response |
| 76 | 0.022/84 | No Response |
| 77 | 0.67/58 | No Response |
| 78 | 2.68/36 | No Response |
| 79 | 0.34/50 | No Response |
| 80 | 0.85/43 | No Response |
| 81 | 0.085/83 | No response |
| 82 | 0.46/80 | Not tested |
| 83 | 1.5/55 | No response |
| 84 | No response | Not tested |
| 85 | 0.026/91 | No response |
| 86 | 0.31/67 | No response |

These results indicate that compounds of the invention are potent M4 receptor agonists and possess a greater than 5-fold selectivity for the M4 receptor compared to the M2 receptor. Accordingly, the compounds of the invention are expected to have usefulness in the prevention or treatment of conditions, such as those discussed above, in which M4 receptor agonism is considered to be beneficial, and moreover are particularly advantageous in view of their lower risk profile with respect to unwanted cardiovascular side-effects associated with M2 receptor agonism.

The invention claimed is:

1. A compound of formula (I) or a pharmaceutically acceptable salt thereof

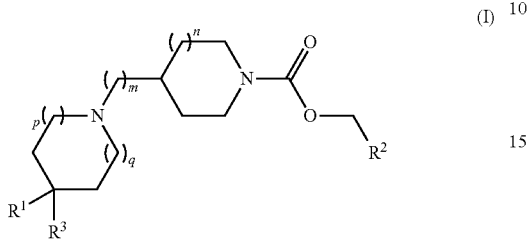

(I)

wherein
m, p and q each independently represent 0 or 1;
n represents an integer 2;
$R^1$ is selected from hydrogen, fluorine, cyano, hydroxyl, amino, and a $C_1$-$C_9$ non-aromatic hydrocarbon group which is optionally substituted with from one to six fluorine atoms and wherein one, two or three carbon atoms of the hydrocarbon group may optionally be replaced by one, two or three heteroatoms independently selected from nitrogen, oxygen and sulphur;
$R^2$ is hydrogen or a $C_1$-$C_6$ non-aromatic hydrocarbon group which is optionally substituted with from one to six fluorine atoms and wherein one, two or three carbon atoms of the hydrocarbon group may optionally be replaced by one, two or three heteroatoms independently selected from nitrogen, oxygen and sulphur;
$R^3$ represents a 5-or 6-membered monocyclic aromatic heterocyclic group containing 1, 2, 3or 4 ring heteroatoms independently selected from nitrogen, oxygen and sulphur, which heterocyclic group may be optionally substituted by at least one substituent selected from halogen, cyano, oxo, —$NR^4R^5$, —$C(O)NR^6R^7$, $C_1$-$C_6$ haloalkyl, $C_1$-$C_6$ haloalkoxy, —$R^8$, —$OCH_2R^8$, $C_1$-$C_6$ alkoxy, $C_3$-$C_8$ cycloalkyl and $C_1$-$C_6$ alkyl, the alkyl substituent itself being optionally substituted by at least one substituent selected from cyano, —$C(O)NR^9R^{10}$, $C_1$-$C_6$ alkoxy and —$NHC(O)R^{11}$, or
$R^3$ represents a group of formula (II)

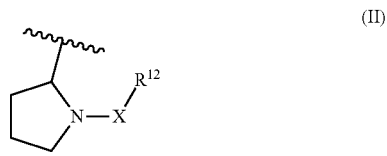

(II)

in which X represents a bond, C(O), C(O)O, $C(O)NR^{13}$ or $SO_2$, and $R^{12}$ represents a $C_1$-$C_6$ alkyl group or a 3-to 10-membered saturated or unsaturated carbocyclic or heterocyclic ring system, each of which may be optionally substituted by at least one substituent selected from halogen, hydroxyl, cyano, oxo, $C_1$-$C_6$ alkyl, $C_2$-$C_6$ alkenyl, $C_1$-$C_6$ haloalkyl, $C_1$-$C_6$ hydroxyalkyl, $C_1$-$C_6$ alkoxy, $C_1$-$C_6$ haloalkoxy, $C_1$-$C_6$ alkylthio, $C_1$-$C_6$ alkylsulphinyl, $C_1$-$C_6$ alkylsulphonyl, $C_1$-$C_6$ alkylcarbonyl, $C_1$-$C_6$ alkylcarbonyloxy, $C_1$-$C_6$ alkoxycarbonyl, —$N(R^{14})_2$, —$CON(R^{15})_2$, $C_3$-$C_6$ cycloalkyl, $C_3$-$C_6$ cycloalkyloxy and $C_3$-$C_6$ cycloalkylmethyl;
$R^4$, $R^5$, $R^6$ and $R^7$ each independently represent a hydrogen atom, $C_1$-$C_6$ alkyl, $C_3$-$C_6$ cycloalkyl or $C_3$-$C_6$ cycloalkylmethyl;
$R^8$ represents a 5-or 6-membered monocyclic aromatic group optionally containing 1, 2, 3 or 4 ring heteroatoms independently selected from nitrogen, oxygen and sulphur, the aromatic group being optionally substituted by at least one substituent selected from halogen and $C_1$-$C_6$ alkyl;
$R^9$, $R^{10}$ and $R^{11}$ each independently represent a hydrogen atom, $C_1$-$C_6$ alkyl or $C_3$-$C_6$ cycloalkyl; and
each $R^{13}$, $R^{14}$ and $R^{15}$ independently represents a hydrogen atom or $C_1$-$C_6$ alkyl group.

2. A compound according to claim 1, wherein, in $R^3$, the 5-or 6-membered monocyclic aromatic heterocyclic group contains from 1 to 3 ring heteroatoms independently selected from nitrogen, oxygen and sulphur.

3. A compound according to claim 1, wherein, in $R^3$, the 5-or 6-membered monocyclic aromatic heterocyclic group contains 1 or 2 nitrogen ring atoms and optionally one further ring heteroatom selected from oxygen and sulphur.

4. A compound according to claim 3, wherein the 5-or 6-membered monocyclic aromatic heterocyclic group is selected from pyrrolyl, imidazolyl, pyrazolyl, oxadiazolyl, thiazolyl, oxazolyl, pyridinyl, pyrimidinyl and pyrazinyl.

5. A compound according to claim 1, wherein, in $R^3$, the 5-or 6-membered monocyclic aromatic heterocyclic group is optionally substituted by one, two, three or four substituents independently selected from fluorine, chlorine, cyano, oxo, —$NR^4R^5$, —$C(O)NR^6R^7$, $C_1$-$C_2$ haloalkyl, $C_1$-$C_2$ haloalkoxy, —$R^8$, —$OCH_2R^8$, $C_1$-$C_2$ alkoxy, $C_3$-$C_6$ cycloalkyl and $C_1$-$C_4$ alkyl, the alkyl substituent itself being optionally substituted by one, two or three substituents independently selected from cyano, —$C(O)NR^9R^{10}$, $C_1$-$C_2$ alkoxy and —$NHC(O)R^{11}$.

6. A compound according to claim 1, wherein $R^1$ is selected from hydrogen and methoxy.

7. A compound according to claim 1, wherein $R^2$ is ethyl.

8. A compound according to claim 1, wherein p and q are each 1.

9. A compound according to claim 1, wherein m is 0.

10. A compound of formula (I) as defined in claim 1 selected from the group consisting of:
Ethyl 4-(4-{1-[(cyclohexylcarbamoyl)methyl]-1H-imidazol-2-yl}piperidin-1-yl)azepane-1-carboxylate,
Ethyl 4-[4-(1H-pyrrol-1-yl)piperidin-1 yl]azepane-1-carboxylate,
Ethyl 4-[4-(1H-pyrazol-1-yl)piperidin-1 yl]azepane-1-carboxylate,
Ethyl 4-{4-[5-(4-chlorophenyl)-1H-pyrazol-1-yl]piperidin-1-yl}azepane-1-carboxylate,
Ethyl 4-[4-(1H-pyrazol-3-yl)piperidin-1 yl]azepane-1-carboxylate,
Ethyl 4-{4-[5-(1-methyl-1H-pyrazol-5-yl)-1H-pyrazol-1-yl]piperidin-1-yl}azepane-1-carboxylate,
Ethyl 4-{4-[4-(4-chlorophenyl)-1H-pyrazol-1-yl]piperidin-1-yl}azepane-1-carboxylate,
Ethyl 4-[4-(1-methyl-1H-imidazol-2-yl)piperidin-1-yl] azepane-1-carboxylate,
Ethyl 4-[4-(1-ethyl-1H-imidazol-2-yl)piperidin-1-yl] azepane-1-carboxylate,
Ethyl 4-[4-(1-prop yl-1H-imidazol-2-yl)piperidin-1-yl] azepane-1-carboxylate, Ethyl 4-[4-(5-methyl-1H-pyrazol-1-yl)piperidin-1-yl]azepane-1-carboxylate,
Ethyl 4-[4-methoxy-4-(1-methyl-1H-imidazol-2-yl)piperidin-1-yl]azepane-1-carboxylate,
Ethyl 4-[4-(1-methyl-1H-pyrazol-5-yl)piperidin-1-yl]azepane-1-carboxylate,
Ethyl 4-(4-(5-isopropyl-1,3,4-oxadiazol-2-yl)piperidin-1-yl)azepane-1-carboxylate,
Ethyl 4-[4-(3-methyl-1H-pyrazol-1-yl)piperidin-1-yl]azepane-1-carboxylate,
Ethyl 4-{4-[3-(thiophen-2-yl)-1H-pyrazol-5-yl]piperidin-1-yl}azepane-1-carboxylate,
Ethyl 4-{4-[4-(4-fluorophenyl)-1H-pyrazol-1-yl]piperidin-1-yl}azepane-1-carboxylate,
Ethyl 4-(4-{1-[(cyclopropylcarbamoyl)methyl]-1H-imidazol-2-yl}piperidin-1-yl)azepane-1-carboxylate,
Ethyl 4-[4-(5-cyclopropyl-1H-pyrazol-1-yl)piperidin-1-yl]azepane-1-carboxylate,
Ethyl 4-{4-[5-(dimethylcarbamoyl)-1H-pyrazol-1-yl]piperidin-1-yl}azepane-1-carboxylate,
Ethyl 4-(4-{5-[1-(propan-2-yl)-1H-pyrazol-4-yl]-1H-pyrazol-1-yl}piperidin-1-yl)azepane-1-carboxylate,
Ethyl 4-{4-[5-(methoxymethyl)-1H-pyrazol-1-yl]piperidin-1-yl}azepane-1-carboxylate,
Ethyl 4-(4-{5-[(cyclopropylmethyl)carbamoyl]-1H-pyrazol-1-yl}piperidin-1-yl)azepane-1-carboxylate,
Ethyl 4-{4-[5-(dimethyl-1,3-thiazol-5-yl)-1H-pyrazol-1-yl]piperidin-1-yl}azepane-1-carboxylate,
Ethyl 4-[4-(1,3-thiazol-2-yl)piperidin-1-yl]azepane-1-carboxylate,
Ethyl 4-[4-(5-cyano-1H-pyrazol-1-yl)piperidin-1-yl]azepane-1-carboxylate,
Ethyl 4-{4-[5-(acetamidomethyl)-1H-pyrazol-1-yl]piperidin-1-yl}azepane-1-carboxylate,
Ethyl 4-[4-(pyridin-4-yl)piperidin-1-yl]azepane-1-carboxylate,
Ethyl 4-[4-(6-methoxypyridin-2-yl)piperidin-1-yl]azepane-1-carboxylate,
Ethyl 4-[4-(2-methoxypyridin-3-yl)piperidin-1-yl]azepane-1-carboxylate,
Ethyl 4-[4-(3-methoxypyridin-2-yl)piperidin-1-yl]azepane-1-carboxylate,
Ethyl 4-[4-(1-methyl-2-oxo-1,2-dihydropyridin-3-yl)piperidin-1-yl]azepane-1-carboxylate,
Ethyl 4-[4-(3-methoxypyrazin-2-yl)piperidin-1-yl]azepane-1-carboxylate,
Ethyl 4-[4-(2-methylpyridin-3-yl)piperidin-1-yl]azepane-1-carboxylate,
Ethyl 4-[4-(2-ethoxy-5-methylpyridin-3-yl)piperidin-1-yl]azepane-1-carboxylate,
Ethyl 4-{4-[2-methoxy-5-(trifluoromethyl)pyridin-3-yl]piperidin-1-yl}azepane-1-carboxylate,
Ethyl 4-[4-(3-methoxypyridin-4-yl)piperidin-1-yl]azepane-1-carboxylate,
Ethyl 4-[4-(5-methoxypyridin-3-yl)piperidin-1-yl]azepane-1-carboxylate,
Ethyl 4-[4-(4-methoxypyridin-3-yl)piperidin-1-yl]azepane-1-carboxylate,
Ethyl 4-{4-[3-(dimethylamino)pyrazin-2-yl]piperidin-1-yl}azepane-1-carboxylate,
Ethyl 4-{4-[6-(dimethylamino)pyrazin-2-yl]piperidin-1-yl}azepane-1-carboxylate,
Ethyl 4-[4-(4-methoxypyrimidin-5-yl)piperidin-1-yl]azepane-1-carboxylate,
Ethyl 4-{4-[2-(difluoromethoxy)pyridin-3-yl]piperidin-1-yl}azepane-1-carboxylate,
Ethyl 4-[4-(2-ethoxypyridin-3-yl)piperidin-1-yl]azepane-1-carboxylate,
Ethyl 4-(4-{2-[(3-methyl-1,2-oxazol-5-yl)methoxy]pyridin-3-yl}piperidin-1-yl)azepane-1-carboxylate,
Ethyl 4-{4-[2-(propan-2-yloxy)pyridin-3-yl]piperidin-1-yl}azepane-1-carboxylate,
Ethyl 4-{4-[1-(cyanomethyl)-2-oxo-1,2-dihydropyridin-3-yl]piperidin-1-yl}azepane-1-carboxylate,
Ethyl 4-[4-(1-ethyl-2-oxo-1,2-dihydropyridin-3-yl)piperidin-1-yl]azepane-1-carboxylate,
Ethyl 4-[4-(5-chloro-2-methoxypyridin-3-yl)piperidin-1-yl]azepane-1-carboxylate,
Ethyl 4-[4-(3,6-dimethylpyrazin-2-yl)piperidin-1-yl]azepane-1-carboxylate,
Ethyl 4-{4-[5-methoxy-2-(trifluoromethyl)pyrimidin-4-yl]piperidin-1-yl}azepane-1-carboxylate,
Ethyl 4-(4-{2-[1-(propan-2-yl)-1H-pyrazol-4-yl]pyridin-3-yl}piperidin-1-yl)azepane-1-carboxylate,
Ethyl 4-{4-[2-(methylamino)pyridin-3-yl]piperidin-1-yl}azepane-1-carboxylate,
Ethyl 4-[4-(5-methoxy-2-methylpyrimidin-4-yl)piperidin-1-yl]azepane-1-carboxylate,
Ethyl 4-{4-[2-(1-methyl-1H-pyrazol-5-yl)pyridin-3-yl]piperidin-1-yl}azepane-1-carboxylate,
Ethyl 4-{4-[2-(dimethylamino)pyridin-3-yl]piperidin-1-yl}azepane-1-carboxylate,
Ethyl 4-[4-(2-cyclopropylpyridin-3-yl)piperidin-1-yl]azepane-1-carboxylate,
Ethyl 4-(4-{2-[(cyclopropylmethyl)amino]pyridin-3-yl}piperidin-1-yl)azepane-1-carboxylate,
Ethyl 4-{4-[5-(trifluoromethyl)-1H-pyrazol-1-yl]piperidin-1-yl}azepane-1-carboxylate,
Ethyl 4-[4-(2-ethylpyridin-3-yl)piperidin-1-yl]azepane-1-carboxylate,
Ethyl 4-[4-(4-methoxypyridazin-3-yl)piperidin-1-yl]azepane-1-carboxylate,
Ethyl 4-{4-[2-(1-methyl-1H-pyrazol-4-yl)pyridin-3-yl]piperidin-1-yl}azepane-1-carboxylate,
Ethyl 4-[4-(pyrimidin-2-yl)piperidin-1-yl]azepane-1-carboxylate,
Ethyl 4-[4-(4-methylpyrimidin-5-yl)piperidin-1-yl]azepane-1-carboxylate,
Ethyl 4-{4-[2-(1,3-thiazol-4-ylmethoxy)pyridin-3-yl]piperidin-1-yl}azepane-1-carboxylate,
Ethyl 4-{4-[2-(2-methylpropyl)pyridin-3-yl]piperidin-1-yl}azepane-1-carboxylate,
Ethyl 4-{4-[2-(1,3-oxazol-2-yl)pyridin-3-yl]piperidin-1-yl}azepane-1-carboxylate,
Ethyl (4S)-4-[4-(1H-pyrazol-1-yl)piperidin-1-yl]azepane-1-carboxylate,
Ethyl (4R)-4-[4-(1H-pyrazol-1-yl)piperidin-1-yl]azepane-1-carboxylate,
Ethyl (4S)-4-[4-(1-methyl-1H-imidazol-2-yl)piperidin-1-yl]azepane-1-carboxylate,
Ethyl (4R)-4-[4-(1-methyl-1H-imidazol-2-yl)piperidin-1-yl]azepane-1-carboxylate,
Ethyl (4S)-4-[4-(2-methoxypyridin-3-yl)piperidin-1-yl]azepane-1-carboxylate,
Ethyl (4R)-4-[4-(2-methoxypyridin-3-yl)piperidin-1-yl]azepane-1-carboxylate,
and pharmaceutically acceptable salts thereof.

11. A process for the preparation of a compound of formula (I) or a pharmaceutically acceptable salt thereof as defined in claim 1 which comprises (i) reacting a compound of formula (X),

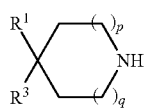
(X)

wherein p, q, R¹ and R³ are as defined in formula (I), with a compound of formula (XIa) or (XIb),

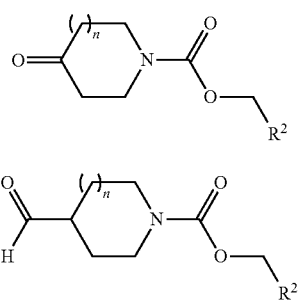

wherein n and R² are as defined in formula (I), under reductive amination conditions; or (ii) when R³ represents a 1,3,4-oxadiazolyl-2-yl group, reacting a compound of formula (XII),

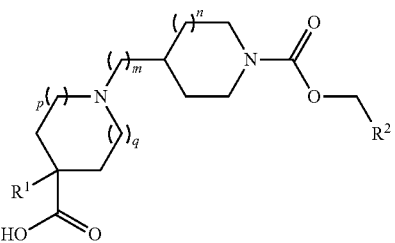
(XII)

wherein m, n, p, q, R¹ and R² are as defined in formula (I), with a compound of formula (XIII), R—C(O)—NH—NH$_2$, wherein R represents hydrogen or an R³ substituent as defined in formula (I), in the presence of a base followed by reaction with a dehydrating agent; and optionally thereafter carrying out one or more of the following procedures:
  converting a compound of formula (I) into another compound of formula (I)
  removing any protecting groups and
  forming a pharmaceutically acceptable salt.

12. A pharmaceutical composition comprising a compound of formula (I) or a pharmaceutically acceptable salt thereof as claimed in claim 1, in association with a pharmaceutically acceptable adjuvant, diluent or carrier.

* * * * *